United States Patent
Robinson et al.

(10) Patent No.: US 11,566,272 B2
(45) Date of Patent: Jan. 31, 2023

(54) AMINO ACID-SENSING DIGUANYLATE CYCLASE AND METHODS OF USE

(71) Applicant: University of Oregon, Eugene, OR (US)

(72) Inventors: Catherine Robinson, Eugene, OR (US); Emily Sweeney, Eugene, OR (US); Karen Guillemin, Eugene, OR (US)

(73) Assignee: University of Oregon, Eugene, OR (US)

( * ) Notice: Subject to any disclaimer, the term of this patent is extended or adjusted under 35 U.S.C. 154(b) by 3 days.

(21) Appl. No.: 16/923,816

(22) Filed: Jul. 8, 2020

(65) Prior Publication Data
US 2021/0010057 A1    Jan. 14, 2021

Related U.S. Application Data

(60) Provisional application No. 62/871,547, filed on Jul. 8, 2019.

(51) Int. Cl.
| | | |
|---|---|---|
| *C12Q 1/48* | (2006.01) | |
| *C12N 9/12* | (2006.01) | |
| *C07K 14/195* | (2006.01) | |
| *G01N 33/68* | (2006.01) | |
| *A61K 35/74* | (2015.01) | |

(52) U.S. Cl.
CPC ............. *C12Q 1/485* (2013.01); *A61K 35/74* (2013.01); *C07K 14/195* (2013.01); *C12N 9/1241* (2013.01); *C12Y 207/07065* (2013.01); *G01N 33/6806* (2013.01); *C07K 2319/60* (2013.01); *G01N 2333/9125* (2013.01)

(58) Field of Classification Search
None
See application file for complete search history.

(56) References Cited

PUBLICATIONS

Giacalone et al., "Ligand-mediated biofilm formation via enhanced physical interaction between a diguanylate cyclase and its receptor," *mBio*, vol. 9, No. 4, e01254-18, 2018 (13 pages).

Luu et al., "Hybrid two-component sensors for identification of bacterial chemoreceptor function," *Appl. Enivron. Microbiol.*, vol. 85, No. 22, e01626-19, 2019 (21 pages).

Moglich et al., "Structure and signaling mechanism of Per-ARNT-Sim domains," *Structure*, vol. 17, pp. 1282-1294, 2009.

Robinson et al., "Experimental bacterial adaptation to the zebrafish gut reveals a primary role for immigration," *PLoS Biology*, vol. 16, No. 12, e2006893, 2018 (26 pages).

Robinson, "Investigating Mechanisms of Bacterial-Host Adaptation," 7th Conference on Beneficial Microbes, Jul. 9, 2018 (29 pages).

Robinson, "SpdE, a novel amino acid-sensing diguanylate cyclase modulates bacterial motility to facilitate transmission within a host-microbe system," *Microbiome: Chemical Mechanisms and Biological Consequences*, Mar. 13, 2019 (29 pages).

Stelitano et al., "Probing the activity of diguanylate cyclases and c-di-GMP phosphodiesterases in real-time by CD spectroscopy," *Nucleic Acids Research*, vol. 41, No. 7, e79, 2013 (9 pages).

*Primary Examiner* — Oluwatosin A Ogunbiyi
(74) *Attorney, Agent, or Firm* — Klarquist Sparkman, LLP

(57) ABSTRACT

Provided are SpdE polypeptides and variants and nucleic acids encoding the SpdE polypeptides and variants. Also provided are vectors including one or more nucleic acids encoding a SpdE polypeptide or variant and cells including a nucleic acid encoding the SpdE polypeptide or variant, as well as cells expressing a SpdE polypeptide or variant and compositions including such cells and a pharmaceutically acceptable carrier. Finally, methods of detecting presence and/or amount of one or more amino acids in a sample are provided. The methods include contacting the sample with a SpdE protein, measuring diguanylate cyclase activity of the SpdE protein; and comparing the diguanylate cyclase activity of the SpdE protein to a control. The methods can utilize isolated SpdE protein or a cell expressing a SpdE protein.

15 Claims, 33 Drawing Sheets
(22 of 33 Drawing Sheet(s) Filed in Color)

Specification includes a Sequence Listing.

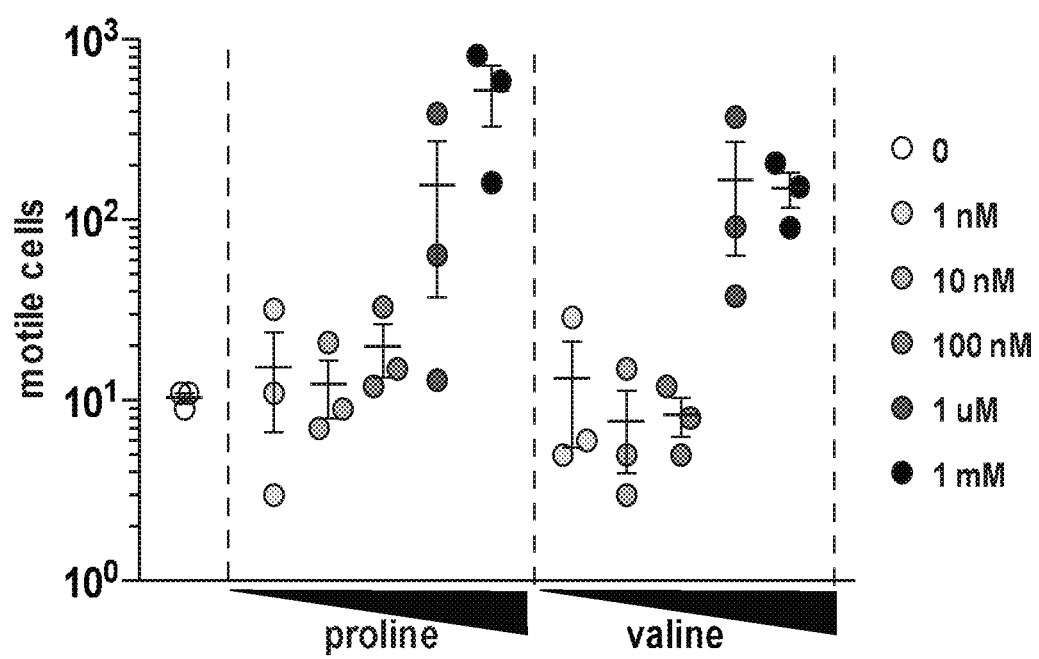

FIG. 19A
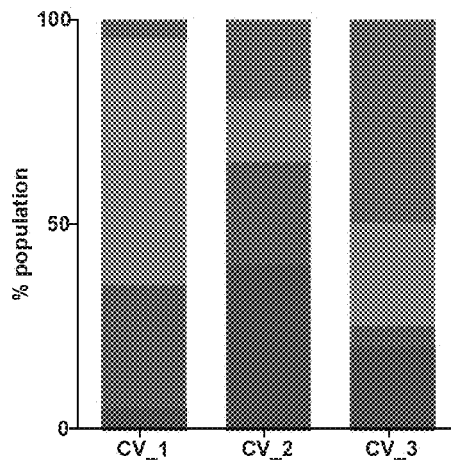
FIG. 19B
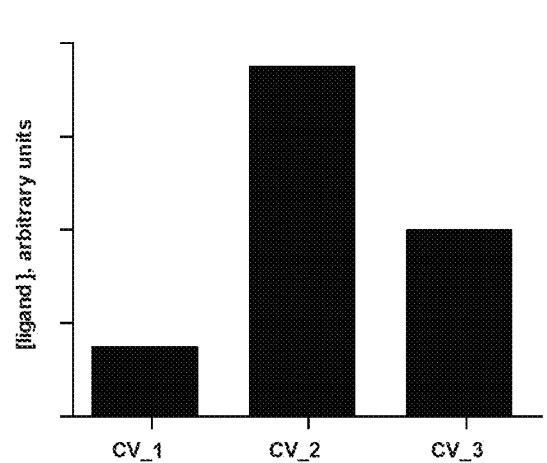
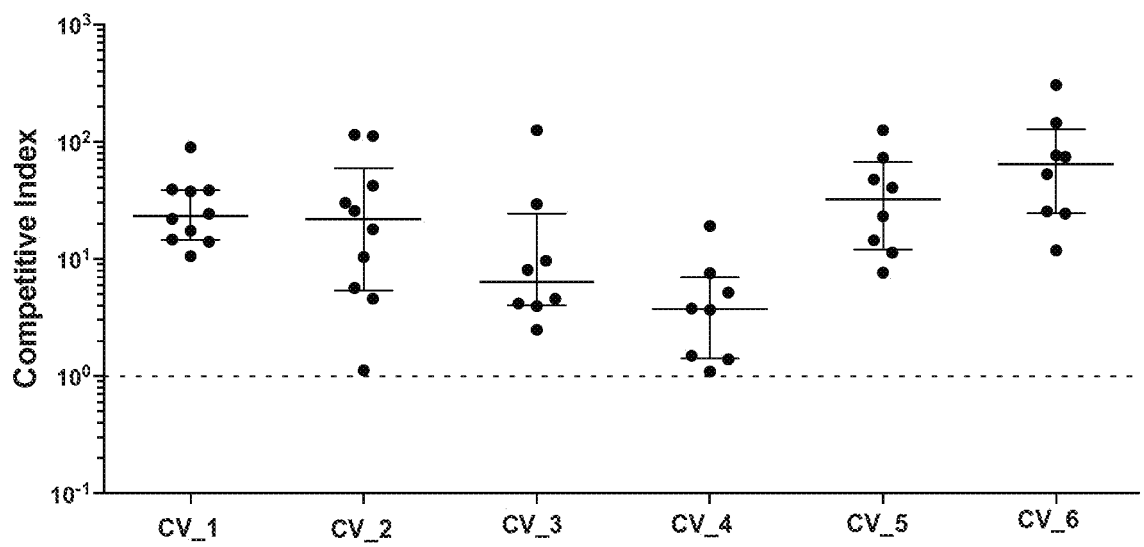
FIG. 19C

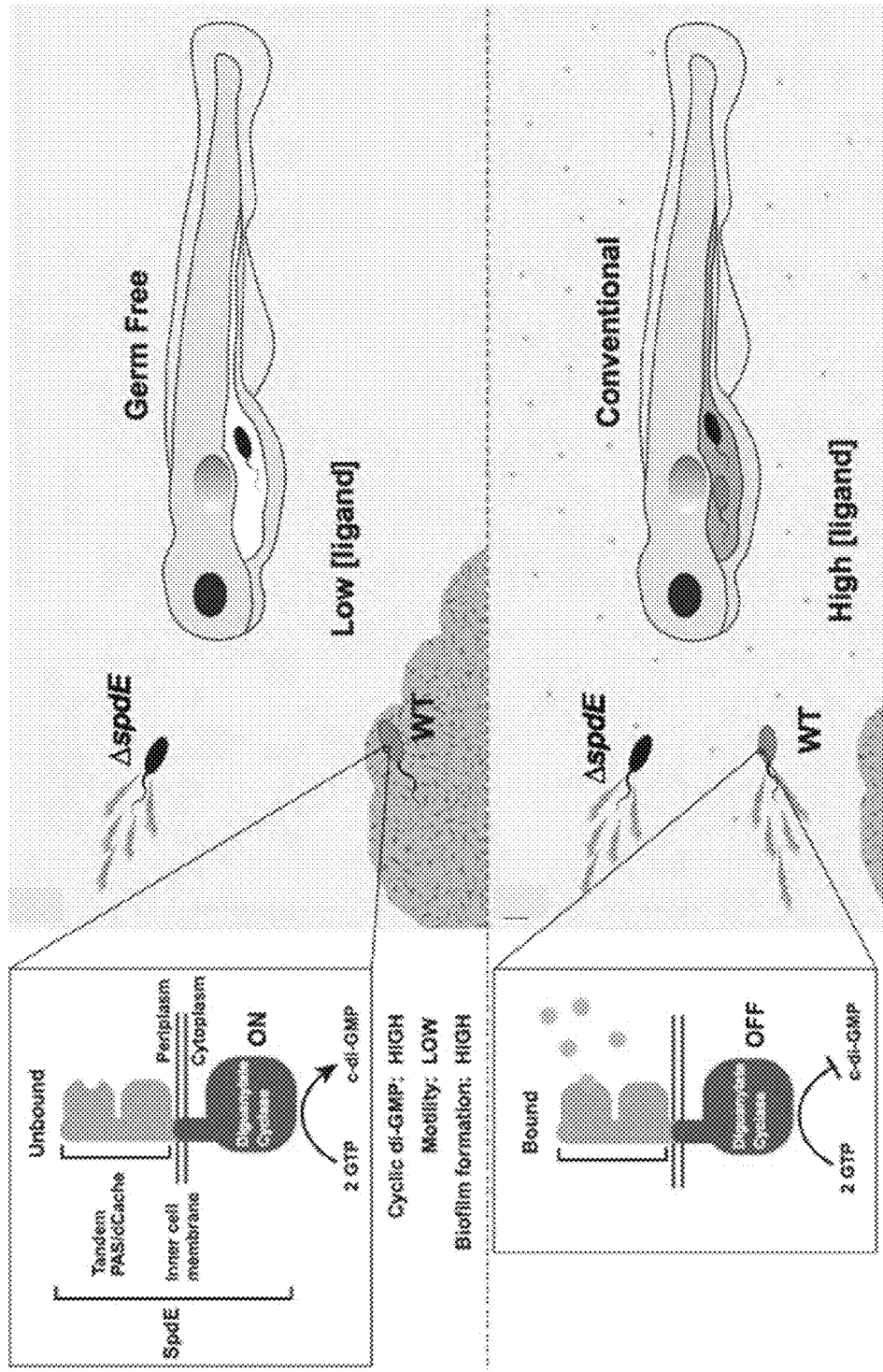

SEQUENCE LISTING

```
<160> NUMBER OF SEQ ID NOS: 8

<210> SEQ ID NO 1
<211> LENGTH: 544
<212> TYPE: PRT
<213> ORGANISM: Aeromonas veronii

<400> SEQUENCE: 1

Met Ser Pro Ala Lys Pro Lys Asn Thr Trp Ser Leu Ile Thr Arg Met
1               5                   10                  15

Arg Leu Gly Phe Leu Leu Leu Phe Ile Pro Val Leu Leu Leu Gly Ser
            20                  25                  30

Ile Tyr Tyr Leu His Met Glu Arg Thr Leu Arg His Glu Gln Gln Gln
        35                  40                  45
```

```
Tyr Leu Ile Ala Arg Asn Thr Gln Tyr Phe His Thr Leu Ile Glu Pro
    50                  55                  60

Tyr Leu Ala Thr Leu Lys Arg Gln Phe Thr Leu Ile Tyr Gln Gln Val
65                  70                  75                  80

Asn Tyr Arg Asp Phe Ser Gly Pro Glu Ile Arg Asn Gly Glu Arg Tyr
                85                  90                  95

Leu Gln Gln Trp Gln Ala Tyr His Lys Val Met Glu Leu Asp Tyr Val
                100                 105                 110

Tyr Val Gly Thr Glu His Arg Lys Met Leu Ile His Pro Ser Trp Gln
                115                 120                 125

Ala Asp Glu Lys Phe Asp Pro Arg Thr Arg Pro Trp Tyr Leu Leu Ala
130                 135                 140

Ala Ser His Pro Gly Gln Ile Val Trp Thr Asp Pro Tyr Tyr Asp Tyr
145                 150                 155                 160

Thr Leu Gly Thr Leu Thr Met Ala Leu Ala Arg Val Ile Lys Asp Pro
                165                 170                 175

Asp Gly Lys Arg Val Gly Val Leu Ser Leu Asp Thr Gln Leu Thr Pro
                180                 185                 190

Leu Ala Ser Trp Leu Asn Ser Arg His Ala Gln Ser His His Leu Gly
                195                 200                 205

Asn Gly Tyr Gln Leu Leu Asn His Asp Gly Leu Val Leu Ala His
    210                 215                 220

Pro Asp Arg Glu Arg Val Phe Lys Pro Leu Ala His Pro Asp Trp Leu
225                 230                 235                 240

Ala Arg Met Gln Gln Pro Gln Gly Phe Phe Leu Asp Asp Ala Ser Gly
                245                 250                 255

Leu Met Val Ser Tyr Tyr Arg Ile Pro Glu Gln Arg Trp Ile Leu Leu
                260                 265                 270

Ser Val Glu Pro Thr Ala Ser Met Gln Gln Val Ile Asp Ser Val Ser
                275                 280                 285

Ile Asn Val Gln Leu Met Ile Ala Val Ala Cys Phe Phe Tyr Leu Leu
    290                 295                 300

Leu Ala Leu Leu Trp Ala Arg Tyr Phe Arg Arg Met Leu Gly Glu Ile
305                 310                 315                 320

Thr Leu Leu Ile Arg Thr Ser Arg Ser Gly Gly Thr Ala Tyr His Gly
                325                 330                 335

Ser Arg Met Leu Glu Leu Ala Lys Val Tyr Glu Met Asp Ala Ala
                340                 345                 350

Ser Gln Asp Phe Ala Gln Ile Arg Gln Gln Ala Asn Gln Asp Lys Leu
                355                 360                 365

Thr Gly Leu Tyr Asn Arg Arg Phe Phe Asp Glu Cys Leu Gln Lys Gln
370                 375                 380

Leu Asn Ser Gly Ala Pro Phe Gly Val Val Met Phe Asp Leu Asp Asp
385                 390                 395                 400

Phe Lys Arg Val Asn Asp Thr His Gly His Gln Ala Gly Asp Val Val
                405                 410                 415

Leu Lys Arg Val Ser Lys Leu Gly Met Asn Leu Phe His Glu Trp Gly
                420                 425                 430

Trp Phe Cys Arg Tyr Gly Gly Glu Glu Leu Val Leu Ile Phe Arg Tyr
                435                 440                 445

Gly Glu Glu Gln Pro Met Leu Pro Ser Leu Leu Glu Ala Phe Arg Leu
450                 455                 460

Gly Val Glu Gln Leu Glu Trp Arg Glu Pro Asp Leu Thr Ile Thr Ile
```

```
                    465                 470                 475                 480
            Ser Gly Gly Val Ala Phe Ser Arg Ser Gly Leu Ser Ala Lys Glu Leu
                                485                 490                 495

Val Glu Leu Ala Asp Lys Gly Val Tyr Gln Ala Lys Arg Glu Gly Lys
                        500                 505                 510

Asn Arg Ile Cys Phe Pro Leu Arg His Thr Pro His Gln Ser Ala Glu
                            515                 520                 525

Glu Gly Val Pro Ala Phe Gly Glu Thr Gln Gln Gln Thr Asn Glu Gly
                        530                 535                 540

<210> SEQ ID NO 2
            <211> LENGTH: 1635
            <212> TYPE: DNA
            <213> ORGANISM: Aeromonas veronii

<400> SEQUENCE: 2
```

| | | | | | |
|---|---|---|---|---|---|
| atgtccccg | ccaagcccaa | gaacacttgg | tctttgatca | cccgcatgcg | gctgggcttc | 60 |
| ctcttgctct | ttatccctgt | gttgctgctc | ggcagcatct | actacctgca | tatggagcgc | 120 |
| accctgcgcc | acgagcagca | acaatatctg | attgctcgca | cacccagta | tttccatacc | 180 |
| ctgatagaac | cctatctggc | gaccctcaaa | cgccagttta | cgctcattta | tcagcaggta | 240 |
| aattatcggg | atttcagcgg | tccggagatc | cgcaacggcg | agcgctacct | gcaacagtgg | 300 |
| caggcctatc | acaaggtgat | ggagctcgat | tacgtctacg | tgggcaccga | gcatcgcaag | 360 |
| atgctgatcc | acccatcctg | gcaggccgac | gagaagttcg | atcccagaac | ccgcccctgg | 420 |
| tatctgctgg | ccgccagcca | tcccggacag | attgtctgga | ctgatcctta | ttacgactac | 480 |
| accttgggca | ctctcaccat | ggcgctggcc | cgggtaatta | agatcctga | cggcaagcgg | 540 |
| gttggcgtac | tctcgctgga | tacccagctc | accccctcg | ccagctggct | aaacagtcgg | 600 |
| catgctcaga | gtcaccatct | gggtaatggc | tatcagctcc | tgctcaacca | tgacgggctg | 660 |
| gtgctggccc | atccggatcg | cgaacgggta | ttcaaacccc | tcgcccaccc | cgactggctg | 720 |
| gcccggatgc | aacagccgca | gggcttttc | ctcgatgatg | ccagcggcct | gatggtctcc | 780 |
| tactaccgca | tccccgagca | gcgctggatc | ctgctcagcg | tcgagccgac | tgccagcatg | 840 |
| caacaggtga | tcgacagcgt | ctccatcaac | gtgcagctga | tgattgccgt | tgcctgctt | 900 |
| ttctatctgc | tgctagccct | gctttgggcc | cgctacttcc | gccgcatgct | ggggagatt | 960 |
| accctgctga | tccgcaccag | ccgctctggc | gggactgcct | atcatggcag | ccgcatgctg | 1020 |
| gagctggcca | aggtctatga | agagatggat | gccgccagtc | aggactttgc | ccagatccgc | 1080 |
| cagcaagcca | atcaggacaa | actcaccggt | ctctacaacc | gccgcttctt | cgacgagtgc | 1140 |
| ctgcagaagc | agctcaacag | tggcgccccc | ttcggggtgg | tgatgttcga | tctggatgat | 1200 |
| ttcaaacggg | tcaacgatac | ccacggccat | caggcggggg | atgtggtgct | caagcgggta | 1260 |
| agcaagctgg | gcatgaatct | gttccacgag | tggggctggt | tctgccgcta | tggcggcgag | 1320 |
| gagctggtgc | tcatcttccg | ttacggcgaa | gagcagccga | tgcttccctc | cctgctggaa | 1380 |
| gcgttccggc | tcggggtgga | gcagctggag | tggcgcgaac | ccgatctcac | catcaccatc | 1440 |
| agcggcgggg | tggctttcag | ccgctccggg | ctctcggcca | aagagctggt | ggagctggcc | 1500 |
| gacaagggg | tctatcaagc | caagcgggag | gggaaaaacc | gtatctgctt | cccactgcgc | 1560 |
| catacccctc | accagagtgc | cgaggagggc | gttcccgcct | tggcgagac | ccagcaacaa | 1620 |
| accaacgagg | ggtag | | | | | 1635 |

```
<210> SEQ ID NO 3
<211> LENGTH: 171
<212> TYPE: PRT
<213> ORGANISM: Artificial Sequence
<220> FEATURE:
<223> OTHER INFORMATION: SpdE frameshift mutation at amino acid 162
      sequence

<400> SEQUENCE: 3

Met Ser Pro Ala Lys Pro Lys Asn Thr Trp Ser Leu Ile Thr Arg Met
1               5                   10                  15

Arg Leu Gly Phe Leu Leu Leu Phe Ile Pro Val Leu Leu Leu Gly Ser
                20                  25                  30

Ile Tyr Tyr Leu His Met Glu Arg Thr Leu Arg His Glu Gln Gln Gln
        35                  40                  45

Tyr Leu Ile Ala Arg Asn Thr Gln Tyr Phe His Thr Leu Ile Glu Pro
    50                  55                  60

Tyr Leu Ala Thr Leu Lys Arg Gln Phe Thr Leu Ile Tyr Gln Gln Val
65                  70                  75                  80

Asn Tyr Arg Asp Phe Ser Gly Pro Glu Ile Arg Asn Gly Glu Arg Tyr
                85                  90                  95

Leu Gln Gln Trp Gln Ala Tyr His Lys Val Met Glu Leu Asp Tyr Val
            100                 105                 110

Tyr Val Gly Thr Glu His Arg Lys Met Leu Ile His Pro Ser Trp Gln
        115                 120                 125

Ala Asp Glu Lys Phe Asp Pro Arg Thr Arg Pro Trp Tyr Leu Leu Ala
    130                 135                 140

Ala Ser His Pro Gly Gln Ile Val Trp Thr Asp Pro Tyr Tyr Asp Tyr
145                 150                 155                 160

Thr Trp Ala Leu Ser Pro Trp Arg Trp Pro Gly
                165                 170

<210> SEQ ID NO 4
<211> LENGTH: 256
<212> TYPE: PRT
<213> ORGANISM: Artificial Sequence
<220> FEATURE:
<223> OTHER INFORMATION: SpdE protein amino acid sequence frameshift at
      amino acid 252

<400> SEQUENCE: 4

Met Ser Pro Ala Lys Pro Lys Asn Thr Trp Ser Leu Ile Thr Arg Met
1               5                   10                  15

Arg Leu Gly Phe Leu Leu Leu Phe Ile Pro Val Leu Leu Leu Gly Ser
                20                  25                  30

Ile Tyr Tyr Leu His Met Glu Arg Thr Leu Arg His Glu Gln Gln Gln
        35                  40                  45

Tyr Leu Ile Ala Arg Asn Thr Gln Tyr Phe His Thr Leu Ile Glu Pro
    50                  55                  60

Tyr Leu Ala Thr Leu Lys Arg Gln Phe Thr Leu Ile Tyr Gln Gln Val
65                  70                  75                  80

Asn Tyr Arg Asp Phe Ser Gly Pro Glu Ile Arg Asn Gly Glu Arg Tyr
                85                  90                  95

Leu Gln Gln Trp Gln Ala Tyr His Lys Val Met Glu Leu Asp Tyr Val
            100                 105                 110

Tyr Val Gly Thr Glu His Arg Lys Met Leu Ile His Pro Ser Trp Gln
        115                 120                 125

Ala Asp Glu Lys Phe Asp Pro Arg Thr Arg Pro Trp Tyr Leu Leu Ala
```

```
            130                 135                 140
Ala Ser His Pro Gly Gln Ile Val Trp Thr Asp Pro Tyr Tyr Asp Tyr
145                 150                 155                 160

Thr Leu Gly Thr Leu Thr Met Ala Leu Ala Arg Val Ile Lys Asp Pro
                165                 170                 175

Asp Gly Lys Arg Val Gly Val Leu Ser Leu Asp Thr Gln Leu Thr Pro
            180                 185                 190

Leu Ala Ser Trp Leu Asn Ser Arg His Ala Gln Ser His His Leu Gly
        195                 200                 205

Asn Gly Tyr Gln Leu Leu Leu Asn His Asp Gly Leu Val Leu Ala His
    210                 215                 220

Pro Asp Arg Glu Arg Val Phe Lys Pro Leu Ala His Pro Asp Trp Leu
225                 230                 235                 240

Ala Arg Met Gln Gln Pro Gln Gly Phe Phe Leu Val Met Pro Ala Ala
                245                 250                 255

<210> SEQ ID NO 5
<211> LENGTH: 538
<212> TYPE: PRT
<213> ORGANISM: Aeromonas caviae

<400> SEQUENCE: 5

Met Glu Ser Gly Leu Asp Lys Arg Ala Val Ser Lys Lys Thr Trp Ser
1               5                   10                  15

Leu Val Ala Arg Met Arg Leu Gly Leu Leu Leu Phe Ile Pro Val
                20                  25                  30

Leu Met Leu Gly Ala Ile Tyr Tyr Leu His Met Glu Arg Ser Leu Gln
            35                  40                  45

Arg Glu Leu Gln Gln Arg Leu Leu Ala Thr Asn His Gln Leu Arg His
        50                  55                  60

Val Phe Ile Glu Pro Tyr Leu Asn Glu Met Glu Arg Gln Phe Ser Leu
65                  70                  75                  80

Ile Tyr Asp Gln Ile Lys Val Glu Asp Ile Ser Gly Pro Arg Leu Arg
                85                  90                  95

Asn Thr Asp Ser Tyr Leu Arg Glu Trp Arg Leu Tyr Lys Gly Val Met
            100                 105                 110

Ala Asp Leu Ile Tyr Ile Tyr Val Gly Thr Ala Glu Arg Gln Met Leu
        115                 120                 125

Ile Tyr Pro Glu Trp Gln Ala Asp Ala Asp Phe Asp Pro Arg Val Arg
    130                 135                 140

Pro Trp Tyr Gln Leu Ala Ser Gln His Val Gly Lys Met Val Trp Thr
145                 150                 155                 160

Glu Pro Tyr Tyr Asp Tyr Thr Asn Gly Thr Leu Val Ile Ala Leu Ala
                165                 170                 175

Arg Ala Ile Thr Asp Lys Glu Gly Lys Val Arg Gly Val Phe Ala Val
            180                 185                 190

Asp Ala Ile Leu Ala Pro Phe Ser Ala Gln Leu Asn Arg Gln Trp Asn
        195                 200                 205

Ser Gly Tyr Gln Met Ile Val Asn Gln Ser Gly Lys Val Leu Ala His
    210                 215                 220

Pro Asp Pro Ser Gln Leu Leu Lys Pro Met Thr His Pro Thr Trp Leu
225                 230                 235                 240

Ser Arg Phe Ser Gly Glu Asp Gly Ile Phe Leu Asp Gln Ala Ser Arg
                245                 250                 255
```

```
Gln Phe Val Ala Tyr Ser Arg Leu Pro Asp His Asn Trp Val Leu Ile
            260                 265                 270

Ser Val Leu Pro Ala Ser Ser Ile Gln Ala Val Val Ala Ser Ala Ser
        275                 280                 285

Leu Asn Val Leu Gly Ile Ile Val Leu Ala Ser Val Leu Tyr Met Val
    290                 295                 300

Leu Ala Leu Ile Trp Ser Arg Tyr Phe Arg Arg Met Leu Asp Glu Ile
305                 310                 315                 320

Ser Thr Val Ile Arg Ala Ser Arg Thr Gln Pro Asp Glu Val His Gln
                325                 330                 335

Gly Gly Met Arg Glu Leu Arg His Val Tyr Ala Glu Leu Ala Glu Val
            340                 345                 350

Ser Lys Asp Tyr His Glu Val Arg Gln Gln Ala Asn Leu Asp Lys Leu
        355                 360                 365

Thr Gly Leu Tyr Asn Arg Arg Phe Phe Asp Glu Arg Leu Asn Arg Leu
    370                 375                 380

Leu Leu Asp Gln Asp Arg Phe Cys Leu Ala Met Ile Asp Leu Asp Gly
385                 390                 395                 400

Phe Lys Arg Ile Asn Asp Thr Tyr Gly His Gln Thr Gly Asp Val Val
                405                 410                 415

Leu Lys Arg Val Ala Ser Phe Gly Ala Lys Leu Leu Gly Asp His Gly
            420                 425                 430

Trp Val Cys Arg Tyr Gly Gly Glu Leu Val Val Leu Phe Ala Asn
            435                 440                 445

Pro Asp Ile His Phe Cys Gln Met Leu Leu Glu Gln Tyr Arg Ile Gly
450                 455                 460

Val Ala Ser Leu His Trp Arg Glu Pro Gly Leu Gly Ile Thr Phe Ser
465                 470                 475                 480

Gly Gly Leu Val Ala Ser Ala Pro Gly Leu Gly Ala Arg Ser Leu Leu
                485                 490                 495

Thr Met Val Asp Ala Glu Val Tyr Arg Ala Lys Gly Asp Gly Lys Asn
            500                 505                 510

Arg Ile Tyr Met Val Asp Pro Leu Ala Pro Arg Ala Asp Ser Pro Ser
        515                 520                 525

Gly Asp Gly Met Leu Ser Lys Glu Glu Ala
    530                 535

<210> SEQ ID NO 6
<211> LENGTH: 1617
<212> TYPE: DNA
<213> ORGANISM: Aeromonas caviae

<400> SEQUENCE: 6
atggagtcag ggttggataa gcgagcagtc tccaaaaaga cctggtccct ggtggcacgg      60
atgcgcctgg gcctgcttct gctcttcatt cccgtcctga tgctgggcgc catctactac     120
ctgcacatgg agcgcagcct gcagcgagag ctgaacagc gcctgctcgc caccaatcac     180
cagttgcgcc acgtcttcat cgagccctac ctgaacgaga tggagcgtca gttctctctc     240
atctacgacc agatcaaggt ggaggacatc agcggccccc gtctgcgcaa caccgactcc     300
tatctcaggg agtggcgtct ctacaagggg gtgatggcgg atctcatcta catctatgtg     360
ggcaccgccg agcgccagat gctgatctac cccgaatggc aggcggatgc ggacttcgat     420
cccagggtgc gccctggta tcagctggcc agccagcatg tgggcaagat ggtctggacc     480
gaaccctact acgactacac caacggcacg ctggtgatcg ccctggcgcg ggccatcacc     540
```

-continued

```
gacaaggagg gcaaggtgcg gggggtcttc gcggtggatg ccatcctggc cccctt ctcc      600 gcccagctga accggcagtg aacagcggc taccagatga tcgtcaacca gtcgggcaag       660
gtgctggccc accccgatcc ctcacaactg ctcaagccca tgacccaccc gacctggctc      720
tcccgcttca gcggggagga cggcatcttc ctggatcagg cgtctcgcca gttcgtggcc      780
tacagccgcc tgccggacca caactgggtg ctgatcagcg tgttgcccgc ctccagcatc      840
caggcggtgg tggcgagcgc ctccctcaac gtgctcggga tcatcgtgct ggccagcgtg      900
ctctacatgg tgctggcact gatctggtcc cgttatttca ggcggatgct ggacgagatc      960
tccaccgtga tccgggccag ccggacccag cctgacgagg tgcaccaggg ggggatgcgc     1020
gagctcaggc acgtctatgc cgagctggcg gaggtgagca aggattatca cgaggtgcgc     1080
cagcaggcga acctcgacaa gctgaccggc ctttacaacc ggcgcttttt cgacgagcgg     1140
ttgaatcggc tgctgctcga tcaggaccgc ttctgcctgg ccatgatcga tctggacggt     1200
ttcaagcgga tcaatgacac ctatggtcac cagaccgggg atgtggtgct caagcgggtg     1260
gccagttttg gcgccaagct gctgggggat catggctggg tatgccgcta tggcggggaa     1320
gagctggtgg tgctgttcgc caatccggac atccacttct gccagatgct gctggagcag     1380
tacaggattg gggtggcctc tctgcactgg cgtgaacccg gtcttgggat caccttcagc     1440
ggcggcctgg tggcgagtgc ccccgggctt ggggccagga gctgctgac catggtcgat      1500 gccgaggtct atcgcgccaa gggtgacggc aagaatcgca tctacatggt ggatcccctg     1560
gctccccggg ccgactcgcc ctcaggggat ggcatgttga gcaaagaaga ggcctga        1617
```

```
<210> SEQ ID NO 7
<211> LENGTH: 696
<212> TYPE: PRT
<213> ORGANISM: Artificial Sequence
<220> FEATURE:
<223> OTHER INFORMATION: SpdE-NarQ fusion protein

<400> SEQUENCE: 7
```

```
Met Ser Pro Ala Lys Pro Lys Asn Thr Trp Ser Leu Ile Thr Arg Met
1               5                   10                  15

Arg Leu Gly Phe Leu Leu Phe Ile Pro Val Leu Leu Leu Gly Ser
            20                  25                  30

Ile Tyr Tyr Leu His Met Glu Arg Thr Leu Arg His Glu Gln Gln Gln
        35                  40                  45

Tyr Leu Ile Ala Arg Asn Thr Gln Tyr Phe His Thr Leu Ile Glu Pro
    50                  55                  60

Tyr Leu Ala Thr Leu Lys Arg Gln Phe Thr Leu Ile Tyr Gln Gln Val
65                  70                  75                  80

Asn Tyr Arg Asp Phe Ser Gly Pro Glu Ile Arg Asn Gly Glu Arg Tyr
                85                  90                  95

Leu Gln Gln Trp Gln Ala Tyr His Lys Val Met Glu Leu Asp Tyr Val
            100                 105                 110

Tyr Val Gly Thr Glu His Arg Lys Met Leu Ile His Pro Ser Trp Gln
        115                 120                 125

Ala Asp Glu Lys Phe Asp Pro Arg Thr Arg Pro Trp Tyr Leu Leu Ala
    130                 135                 140

Ala Ser His Pro Gly Gln Ile Val Trp Thr Asp Pro Tyr Tyr Asp Tyr
145                 150                 155                 160

Thr Leu Gly Thr Leu Thr Met Ala Leu Ala Arg Val Ile Lys Asp Pro
                165                 170                 175
```

```
Asp Gly Lys Arg Val Gly Val Leu Ser Leu Asp Thr Gln Leu Thr Pro
            180                 185                 190

Leu Ala Ser Trp Leu Asn Ser Arg His Ala Gln Ser His His Leu Gly
        195                 200                 205

Asn Gly Tyr Gln Leu Leu Leu Asn His Asp Gly Leu Val Leu Ala His
    210                 215                 220

Pro Asp Arg Glu Arg Val Phe Lys Pro Leu Ala His Pro Asp Trp Leu
225                 230                 235                 240

Ala Arg Met Gln Gln Pro Gln Gly Phe Phe Leu Asp Asp Ala Ser Gly
                245                 250                 255

Leu Met Val Ser Tyr Tyr Arg Ile Pro Glu Gln Arg Trp Ile Leu Leu
            260                 265                 270

Ser Val Glu Pro Thr Ala Ser Met Gln Gln Val Ile Asp Ser Val Ser
        275                 280                 285

Ile Asn Val Gln Leu Met Ile Ala Val Ala Cys Phe Phe Tyr Leu Leu
    290                 295                 300

Leu Ala Leu Leu Trp Leu Asn Gln Leu Val Thr Ala Ser Gln Arg Ile
305                 310                 315                 320

Glu His Gly Gln Phe Asp Ser Pro Pro Leu Asp Thr Asn Leu Pro Asn
                325                 330                 335

Glu Leu Gly Leu Leu Ala Lys Thr Phe Asn Gln Met Ser Ser Glu Leu
            340                 345                 350

His Lys Leu Tyr Arg Ser Leu Glu Ala Ser Val Glu Glu Lys Thr Arg
        355                 360                 365

Asp Leu His Glu Ala Lys Arg Arg Leu Glu Val Leu Tyr Gln Cys Ser
    370                 375                 380

Gln Ala Leu Asn Thr Ser Gln Ile Asp Val His Cys Phe Arg His Ile
385                 390                 395                 400

Leu Gln Ile Val Arg Asp Asn Glu Ala Ala Glu Tyr Leu Glu Leu Asn
                405                 410                 415

Val Gly Glu Asn Trp Arg Ile Ser Glu Gly Gln Pro Asn Pro Glu Leu
            420                 425                 430

Pro Met Gln Ile Leu Pro Val Thr Met Gln Glu Thr Val Tyr Gly Glu
        435                 440                 445

Leu His Trp Gln Asn Ser His Val Ser Ser Ser Glu Pro Leu Leu Asn
    450                 455                 460

Ser Val Ser Ser Met Leu Gly Arg Gly Leu Tyr Phe Asn Gln Ala Gln
465                 470                 475                 480

Lys His Phe Gln Gln Leu Leu Leu Met Glu Glu Arg Ala Thr Ile Ala
                485                 490                 495

Arg Glu Leu His Asp Ser Leu Ala Gln Val Leu Ser Tyr Leu Arg Ile
            500                 505                 510

Gln Leu Thr Leu Leu Lys Arg Ser Ile Pro Glu Asp Asn Ala Thr Ala
        515                 520                 525

Gln Ser Ile Met Ala Asp Phe Ser Gln Ala Leu Asn Asp Ala Tyr Arg
    530                 535                 540

Gln Leu Arg Glu Leu Leu Thr Thr Phe Arg Leu Thr Leu Gln Gln Ala
545                 550                 555                 560

Asp Leu Pro Ser Ala Leu Arg Glu Met Leu Asp Thr Leu Gln Asn Gln
                565                 570                 575

Thr Ser Ala Lys Leu Thr Leu Asp Cys Arg Leu Pro Thr Leu Ala Leu
            580                 585                 590
```

```
Asp Ala Gln Met Gln Val His Leu Leu Gln Ile Ile Arg Glu Ala Val
            595                 600                 605

Leu Asn Ala Met Lys His Ala Asn Ala Ser Glu Ile Ala Val Ser Cys
    610                 615                 620

Val Thr Ala Pro Asp Gly Asn His Thr Val Tyr Ile Arg Asp Asn Gly
625                 630                 635                 640

Ile Gly Ile Gly Glu Pro Lys Glu Pro Glu Gly His Tyr Gly Leu Asn
                645                 650                 655

Ile Met Arg Glu Arg Ala Glu Arg Leu Gly Gly Thr Leu Thr Phe Ser
            660                 665                 670

Gln Pro Ser Gly Gly Gly Thr Leu Val Ser Ile Ser Phe Arg Ser Ala
        675                 680                 685

Glu Gly Glu Glu Ser Gln Leu Met
    690                 695

<210> SEQ ID NO 8
<211> LENGTH: 2091
<212> TYPE: DNA
<213> ORGANISM: Artificial Sequence
<220> FEATURE:
<223> OTHER INFORMATION: SpdE-NarQ fusion nucleic acid

<400> SEQUENCE: 8 atgtccccg ccaagcccaa gaacacttgg tctttgatca cccgcatgcg gctgggcttc      60
ctcttgctct ttatccctgt gttgctgctc ggcagcatct actacctgca tatggagcgc    120
accctgcgcc acgagcagca caatatctg attgctcgca cacccagta tttccatacc      180 ctgatagaac cctatctggc gaccctcaaa cgccagttta cgctcattta tcagcaggta    240
aattatcggg atttcagcgg tccggagatc cgcaacggcg agcgctacct gcaacagtgg    300
caggcctatc acaaggtgat ggagctcgat tacgtctacg tgggcaccga gcatcgcaag    360
atgctgatcc acccatcctg gcaggccgac gagaagttcg atcccagaac cgcccctgg    420 tatctgctgg ccgccagcca tcccggacag attgtctgga ctgatcctta ttacgactac    480
accttgggca ctctcaccat ggcgctggcc cgggtaatta agatcctga cggcaagcgg    540 gttggcgtac tctcgctgga tacccagctc accccctcg ccagctggct aaacagtcgg    600
catgctcaga gtcaccatct gggtaatggc tatcagctcc tgctcaacca tgacgggctg    660
gtgctggccc atccggatcg cgaacgggta ttcaaacccc tcgcccaccc cgactggctg    720
gcccggatgc aacagccgca gggctttttc ctcgatgatg ccagcggcct gatggtctcc    780
tactaccgca tccccgagca cgctggatc ctgctcagcg tcgagccgac tgccagcatg    840
caacaggtga tcgacagcgt ctccatcaac gtgcagctga tgattgccgt gcctgctt     900 ttctatctgc tgctagccct gctttggctg aatcagctgg ttaccgccag tcagcgtatt    960
gaacacgggc agttcgactc gccgccgctg ataccaacc tgccgaatga gcttggtctg   1020
cttgcaaaaa cctttaacca gatgtcgagc gagctgcata aattgtaccg ttcgctggaa   1080
gcgtcagtag aagaaaagac ccgcgatctc cacgaggcca gcgtcgtct ggaggtgttg    1140 tatcagtgtt cgcaggcgct gaacactagc cagattgatg tgcattgttt ccgccatatt   1200
ttgcagattg ttcgcgacaa tgaagcggct gaatatctgg agttaaatgt cggtgaaaac   1260
tggcggatta gcgaagggca accaaaccog gaattgccga tgcagatttt accggtgaca   1320
atgcaagaga cggtttacgg cgaactgcac tggcaaaaata gtcacgttc atcatcagaa   1380 ccgctgctta acagcgtttc gtcgatgctg ggacgcggtt tgtactttaa tcaggcgcag   1440
```

```
aagcattttc agcaattatt gttgatggaa gaacgtgcga ccatcgcccg cgaattgcac    1500
gactcgctgg ctcaggtact ttcttactta cgtatccagt tgacgttact gaagcgttcg    1560
ataccggaag ataacgccac cgcacaaagt atcatggccg attttccca ggcgttgaat    1620 gatgcttatc ggcagttacg cgagctgttg actactttcc gcctgacgct gcagcaggcg    1680
gatctcccct ccgcattgag ggaaatgctg gatacgttac aaaatcaaac cagcgccaaa    1740
ctgaccctcg actgccgtct gccaaccctg gcactggatg cgcaaatgca ggtgcatttg    1800
ttgcaaatta ttcgcgaagc ggtgctgaat gcgatgaagc acgccaacgc cagcgaaatc    1860
gccgtcagtt gcgtcaccgc gccggacggc aatcacacgg tttatatccg tgataacggg    1920
attggtatcg gtgaaccgaa agaacccgaa ggtcattatg gtctgaatat catgcgcgaa    1980
cgcgcggaac ggctaggtgg gacgctgact ttttcacaac cttccggcgg cggcacgtta    2040
gtgagtatta gctttcgctc tgcggagggt gaggaaagtc agttaatgta a             2091
```

AMINO ACID-SENSING DIGUANYLATE CYCLASE AND METHODS OF USE

CROSS REFERENCE TO RELATED APPLICATION

This application claims the benefit of U.S. Provisional Application No. 62/871,547, filed Jul. 8, 2019, which is incorporated herein by reference in its entirety.

ACKNOWLEDGMENT OF GOVERNMENT SUPPORT

This invention was made with government support under Grant Nos. P01 GM125576, F32 DK108591, and P50 GM098911 awarded by the National Institutes of Health. The government has certain rights in the invention.

FIELD

This disclosure relates to amino acid-sensing diguanylate cyclases from *Aeromonas* and methods of use.

BACKGROUND

Host-associated microbial communities, especially those of the vertebrate gastrointestinal tract, are compositionally diverse and dynamic. These consortia perform a myriad of functions that are intimately tied to various aspects of host health and development. In zebrafish, resident bacteria play important roles in the maturation of the zebrafish intestine, including promoting intestinal epithelial cell proliferation and recruiting innate immune cells in the gut. Many of these effects of the microbiota are conserved across animal species.

Host colonization is typically envisaged at the scale of the individual host, where it is generally believed that microbial success is determined by capacities for growth and persistence within the host, impacted by interactions with both the host and co-colonizing microbes. Indeed, these within-host interactions are important for selection of microbial traits that enable host colonization. However, several lines of evidence demonstrate that extra-host aspects of host-microbe systems are also potential sites of selection for traits that contribute to colonization success. Considering that animals initiate life essentially devoid of microbes, microbiome constituents must first migrate, either actively or passively, into the host from external sources in order to constitute the microbiome. Furthermore, microbes are continually introduced into the microbiome, albeit at various rates, throughout the host's life, for example, via processes of ecological succession early in host development, after perturbations such as antibiotic treatment, and continual flux of strains over time. The specific origins of these microbes are not entirely understood but include environmental sources, across-body sites, diet, and transmission among hosts.

SUMMARY

Disclosed herein is a family of genes and cognate proteins from the bacterial genus *Aeromonas* (designated Sensing proline diguanylate cyclase Enzyme or SpdE) that mediates host colonization and has amino acid-sensing activity. Methods of use of the SpdE genes and proteins are also provided.

In some embodiments, provided is an isolated SpdE polypeptide from *Aeromonas veronii* (isolate ZOR0001; Aer01) including or consisting of the amino acid sequence of SEQ ID NO: 1, or a SpdE polypeptide with at least 75%, 85%, 90%, 95%, 96%, 97%, 98%, or 99% sequence identity to the amino acid sequence of SEQ ID NO: 1. Also provided are variant SpdE polypeptides, including, but not limited to one or more of W127*, Q362*, a frameshift mutation starting at amino acid 162 (e.g., SEQ ID NO: 3), a frameshift mutation starting at amino acid 252 (e.g., SEQ ID NO: 4), A298D, T321S, A363T, W140A, and Y157A.

In other embodiments, an isolated SpdE polypeptide from *Aeromonas caviae* (isolate ZOR0002; Aer02) including or consisting of the amino acid sequence of SEQ ID NO: 5 is provided. In some examples, the SpdE polypeptide has at least 75%, 85%, 90%, 95%, 96%, 97%, 98%, or 99% sequence identity to the amino acid sequence of SEQ ID NO: 5.

In additional embodiments, a SpdE polypeptide includes an amino acid sequence with at least 50% sequence identity (such as at least 50%, at least 53%, at least 55%, at least 60%, at least 65%, at least 70%, at least 75%, at least 85%, at least 90%, at least 95%, at least 96%, at least 97%, at least 98%, or at least 99% sequence identity) with a PAS/dCache domain of a SpdE polypeptide. In particular non-limiting examples, the PAS/dCache domain includes or consists of amino acids 38-286 of SEQ ID NO: 1 or amino acids 43-290 of SEQ ID NO: 5.

In further embodiments, amino acid sensors including a SpdE amino acid sensing domain linked to a heterologous signaling domain are provided. In some examples, the sensor includes a SpdE PAS/dCache domain linked to a bacterial signaling domain. In one example, a disclosed amino acid sensor includes at least one SpdE PAS/dCache domain (e.g., at least a SpdE N-terminal PAS/dCache domain) and SpdE transmembrane domains operably linked to an *E. coli* NarQ signaling domain. In particular examples, the sensor includes a polypeptide with an amino acid sequence with at least 85% sequence identity (such as at least 90%, at least 95%, at least 96%, at least 97%, at least 98%, or at least 99% sequence identity) with SEQ ID NO: 7.

Also provided are nucleic acids encoding the disclosed SpdE polypeptides. In some embodiments, provided is an isolated nucleic acid encoding an Aer01 SpdE polypeptide, wherein the nucleic acid includes or consists of the nucleic acid sequence of SEQ ID NO: 2, or a nucleic acid sequence with at least 75%, 85%, 90%, 95%, 96%, 97%, 98%, or 99% sequence identity to the nucleic acid sequence of SEQ ID NO: 2. In other embodiments, provided is an isolated nucleic acid encoding an Aer02 SpdE polypeptide, wherein the nucleic acid includes or consists of the nucleic acid sequence of SEQ ID NO: 6, or a nucleic acid sequence with at least 75%, 85%, 90%, 95%, 96%, 97%, 98%, or 99% sequence identity to the nucleic acid sequence of SEQ ID NO: 6. Further provided are nucleic acids encoding variant SpdE polypeptides, including nucleic acids encoding one or more of W127*, Q362*, a frameshift mutation starting at amino acid 162, a frameshift mutation starting at amino acid 252, A298D, T321S, A363T, W140A, and Y157A SpdE variants. In additional embodiments, the nucleic acid encodes a SpdE polypeptide with an amino acid sequence at least 50% sequence identity (such as at least 50%, at least 53%, at least 55%, at least 60%, at least 65%, at least 70%, at least 75%, at least 85%, at least 90%, at least 95%, at least 96%, at least 97%, at least 98%, or at least 99% sequence identity) with a PAS/dCache domain of a SpdE polypeptide (e.g., amino acids 38-286 of SEQ ID NO: 1 or amino acids 43-290 of SEQ ID NO: 5).

Further disclosed are vectors including the SpdE nucleic acids provided herein. In some embodiments, the vector includes a nucleic acid including or consisting of the nucleic acid sequence of SEQ ID NO: 2, or a nucleic acid sequence with at least 75%, 85%, 90%, 95%, 96%, 97%, 98%, or 99% sequence identity to the nucleic acid sequence of SEQ ID NO: 2. In further embodiments, the vector includes a nucleic acid including or consisting of the nucleic acid sequence of SEQ ID NO: 6, or a nucleic acid sequence with at least 75%, 85%, 90%, 95%, 96%, 97%, 98%, or 99% sequence identity to the nucleic acid sequence of SEQ ID NO: 6. In other embodiments, the vector includes a nucleic acid encoding a variant SpdE polypeptide, for example, a nucleic acid encoding one or more of W127*, Q362*, a frameshift mutation starting at amino acid 162 (e.g., SEQ ID NO: 3), a frameshift mutation starting at amino acid 252 (e.g., SEQ ID NO: 4), A298D, T321S, A363T, W140A, and Y157A SpdE variants. In some examples, the vector includes the nucleic acid operably linked to a promoter. In some examples, the vector is included in a cell (such as a bacterial cell).

Also disclosed are cells expressing a SpdE protein (such as a heterologous SpdE protein). In some examples, the SpdE protein includes the amino acid sequence of SEQ ID NO: 1 or an amino acid sequence with at least 75%, 85%, 90%, 95%, 96%, 97%, 98%, or 99% sequence identity to the amino acid sequence of SEQ ID NO: 1. In other examples, the SpdE protein includes the amino acid sequence of SEQ ID NO: 5 or an amino acid sequence with at least 75%, 85%, 90%, 95%, 96%, 97%, 98%, or 99% sequence identity to the amino acid sequence of SEQ ID NO: 5. In other examples, the SpdE protein is a variant SpdE protein, which may include one or more of one or more of W127*, Q362*, a frameshift mutation starting at amino acid 162, a frameshift mutation starting at amino acid 252, A298D, T321S, A363T, W140A, and Y157A. In some examples, the cell includes a nucleic acid encoding the SpdE protein, such as a nucleic acid including the nucleic acid sequence of SEQ ID NO: 2 or SEQ ID NO: 6, or a nucleic acid sequence with at least 75%, 85%, 90%, 95%, 96%, 97%, 98%, or 99% sequence identity to the nucleic acid sequence of SEQ ID NO: 2 or SEQ ID NO: 6. In other embodiments, the cell includes a nucleic acid encoding a variant SpdE polypeptide, such as those described herein. In other examples, the cell may include a SpdE protein with reduced activity compared to a wild type SpdE protein or may have a deletion or knockout of the gene encoding the SpdE protein. In some embodiments, the cell is a bacterial cell (e.g., *Escherichia coli*, *Aeromonas veronii*, *Lactobacillus* sp., *Lactococcus* sp., *Bifidobacterium* sp., or *Streptococcus* sp.).

Also described are compositions including a cell expressing a disclosed SpdE protein or a variant thereof and a pharmaceutically acceptable carrier. The composition may be administered to a subject.

Provided herein are methods of detecting presence and/or amount of one or more amino acids in a sample. The methods include contacting the sample with a SpdE protein (e.g., SEQ ID NO: 1, SEQ ID NO: 5, or a variant thereof), measuring diguanylate cyclase activity of the SpdE protein; and comparing the diguanylate cyclase activity of the SpdE protein to a control (e.g., diguanylate cyclase activity of the SpdE protein in the absence of the sample). A decrease in diguanylate cyclase activity compared to the control can indicate the presence and/or amount of the one or more amino acids in the sample. In some examples, the one or more amino acids include proline, valine, isoleucine, leucine, alanine, methionine, or threonine. Diguanylate cyclase activity can be measured by determining an amount of cyclic-di-GMP and/or pyrophosphate.

In other embodiments, the method includes contacting the sample with a cell expressing a disclosed SpdE protein and measuring motility of the cell compared to a control (e.g., a cell expressing the SpdE protein that is not contacted with the sample). An increase in the motility of the cell compared to the control can indicate the presence and/or amount of amino acids in the sample.

Also provided are methods of detecting presence and/or amount of one or more amino acids in a sample using a SpdE-signaling domain fusion protein provided herein. The methods include contacting a sample with a SpdE-signaling domain fusion protein (e.g., SEQ ID NO: 7), measuring activity of the signaling domain, and comparing the activity of the signaling domain to a control. In some examples, the method includes detecting the presence and/or amount of one or more of proline, valine, isoleucine, leucine, alanine, methionine, or threonine. The fusion protein is in an active state in the absence of ligand (as seen for the native SpdE), and activity of the signaling domain (e.g., a direct or indirect activity of the signaling domain) decreases with increasing ligand concentrations. Thus, in some examples, a decrease in activity compared to a control indicates presence or amount of the ligand, such as an amino acid. In one example, the signaling domain is a NarQ signaling domain and the activity is β-galactosidase activity indirectly regulated by the NarQ signaling domain.

In some examples, the sample is a biological sample (e.g., plasma, serum, or urine) from a subject having or suspected to have a disorder associated with alterations in amino acid levels. In some examples, the subject has or is suspected to have insulin resistance, prediabetes, type II diabetes, obesity, maple syrup disease, hyperprolinemia, or Crohn's disease. If an increase in amount or presence of one or more amino acids compared to a control (e.g., a subject without the disorder), the subject is identified as having the disorder. In some examples, the subject is then administered one or more treatments for the disorder.

The foregoing and other features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A shows competitive indices of the WTanc, and evolved isolate (containing only a predicted SpdE mutation), the ΔSpdE, the SpdE over-expressor, and the SpdE complemented strain; all in competition against a differentially-tagged WT reference strain. FIG. 6B shows competitive indices from gavage experiments with the evolved isolate and ΔSpdE showing for both the competitive advantage was dependent on water inoculation (no difference in gavaged competitions), which suggests an increased immigration phenotype. FIG. 6C is a graph showing immigration experiment data. FIG. 6D shows fish-to-fish transmission.

FIG. 8A illustrates SpdE protein secondary structure (with specific sites of mutation in evolved isolates). FIG. 8B are representative thermofluor assay curves showing where the Tm is, which is used to determine ΔTm. FIG. 8C is a graph of thermofluor assay results with A01 spdE, showing number of degrees shifted compared to the control for different amino acids. FIG. 8D is an alignment of A01 and A02 spdE amino acid sequences (Tandem PAS/dCache domains). SpdE_A01: amino acids 38-286 of SEQ ID NO: 1; SpdE_A02: amino acids 43-290 of SEQ ID NO: 5. FIG. 8E is a graph of thermofluor assay results with A02 spdE, showing number of degrees shifted compared to the control for different amino acids.

FIGS. 12A-12G show that Aer01 SpdE regulates motility and biofilm formation via modulation of intracellular c-di-GMP. FIG. 12A is a graph of intracellular quantification of c-di-GMP in the presence/absence of ligands. FIG. 12B shows representative growth curves from exploration assay showing how the "exploration response" is determined (presented in FIG. 12C) by finding the difference in time to OD 0.5 between different conditions (black double arrow). FIG. 12C is a graph of quantified exploration assay summary data for multiple ligands. FIG. 12D shows cellular level motility: swimming tracks. FIG. 12E is a graph of number of motile cells detected per movie across conditions. FIG. 12F shows violin plots of WT and ΔSpdE swim speeds for all tracks in EM+/−proline as measured directly on the light sheet (numbers below each plot is the number of tracks included). FIG. 12G is a graph of combined biofilm data.

FIG. 14A is a standard curve of inoculum and FIG. 14B shows correlation between inoculum and OD 0.5.

FIG. 18A shows that in competition experiments between the WT and ΔSpdE, in the absence of ligand the CIs were very high. In the presence of ligands, the CIs were significantly lower. FIG. 18B is a graph of immigration rate experiments: WT+/−valine, spdE_KO. In the presence of ligand, WT migrated into the fish faster (similar to the KO). FIG. 18C is a graph of competitive indices comparing GF and CV competitions. FIG. 18D shows GF vs CV exploration assays. FIG. 18E shows GF vs CV biofilm assays.

FIGS. 19A-19C illustrate that CV microbiota varies across fish experiments. FIG. 19A is a hypothetical schematic of variation in conventional communities. FIG. 19B shows hypothetical variation in pools of spdE ligands across experiments due to differences in community memberships, and therefore metabolic function, leading to differences in free amino acids. FIG. 19C shows competitive index (CI) data for competitions in independent experiments in CV fish.

FIGS. 20A-20D illustrate a model for SpdE-dependent modulation of Aer01 motility and host colonization. FIGS. 20A and 20B show state where SpdE ligands are absent or low in the system, therefore SpdE diguanylate cyclase is active ("ON") resulting in low motility of WT Aer01 and decreased host colonization. FIGS. 20C and 20D show state where SpdE ligand concentrations are high, therefore SpdE diguanylate cyclase activity is reduced ("OFF"), resulting in high motility and increased host colonization.

SEQUENCE LISTING

Figure 1:
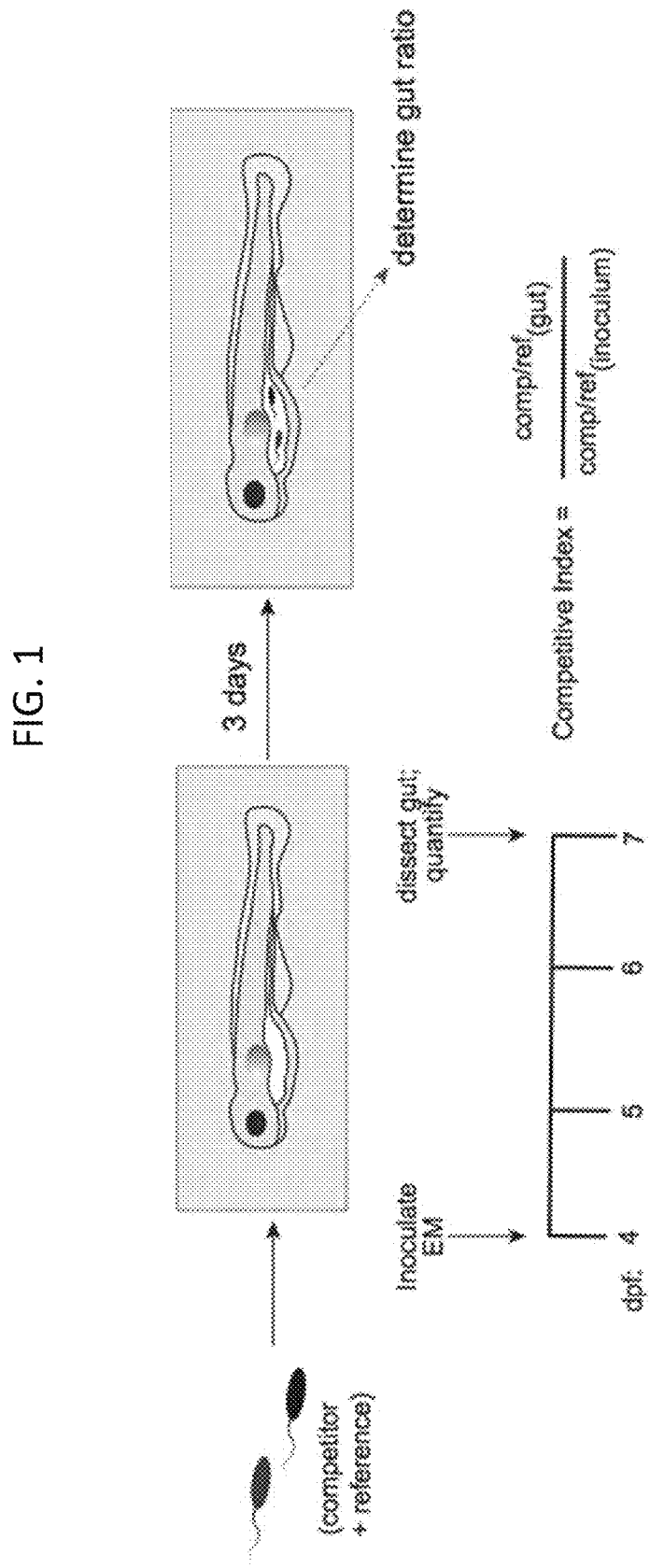
FIG. 1 is a schematic diagram of a competition assay.

Any nucleic acid and amino acid sequences listed herein and in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Jul. 7, 2020, and is ~26 kilobytes, which is incorporated by reference herein.

SEQ ID NO: 1 is an exemplary Aer01 SpdE amino acid sequence.

SEQ ID NO: 2 is an exemplary Aer01 spdE nucleic acid sequence.

SEQ ID NO: 3 is an Aer01 SpdE amino acid sequence resulting from a frameshift mutation starting at amino acid 162.

SEQ ID NO: 4 is an Aer01SpdE amino acid sequence resulting from a frameshift mutation starting at amino acid 252.

SEQ ID NO: 5 is an exemplary Aer02 SpdE amino acid sequence.

SEQ ID NO: 6 is an exemplary Aer02 spdE nucleic acid sequence.

SEQ ID NO: 7 is the amino acid sequence of an exemplary SpdE-NarQ fusion protein.

SEQ ID NO: 8 is a nucleic acid sequence encoding a SpdE-NarQ fusion protein.

DETAILED DESCRIPTION

The inventors have developed a tractable experimental evolution system to investigate the bacterial traits that contribute to host colonization. Using this model, a zebrafish gut isolate, *Aeromonas* (ZOR0001), was adapted to optimize its ability to colonize the larval zebrafish gut. The first adaptation to evolve was increased immigration into the host from the environment. Genomic sequencing of evolved isolates showed that all replicate evolved lines had mutations in the same gene, indicating strong selection for loss-of-function of its encoded protein. This gene, spdE, codes for a previously uncharacterized novel transmembrane protein that contains a diguanylate cyclase domain, and a small molecule-binding tandem PAS domain.

Several ligands of the PAS domain were identified, a subset of hydrophobic amino acids. Moreover, the outer PAS domain was responsible for ligand binding. To further demonstrate that these amino acids bind and impact SpdE function, the inventors showed that intracellular cyclic-di-GMP, the synthetic product of diguanylate cyclase activity, was modulated in the presence of ligand in a SpdE-dependent manner. Likewise, it was demonstrated that *Aeromonas* has a SpdE-dependent hyper-motility phenotype modulated by amino acid ligands. Finally, SpdE ligands increased *Aeromonas* immigration into larval zebrafish, therefore increasing their competitive fitness for gut colonization.

I. Terms

Unless otherwise noted, technical terms are used according to conventional usage. Definitions of common terms in molecular biology may be found in *Lewin's Genes* X, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, $3^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank Accession numbers (for the sequences present on Jul. 8, 2019). In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Control: A sample or standard used for comparison with an experimental sample. In some embodiments, the control is SpdE activity (e.g., diguanylate cyclase activity or cell motility) in the absence of a ligand or sample. In other embodiments, the control is activity (e.g., diguanylate cyclase activity or cell motility) of a wild type SpdE protein. In other embodiments, the control is a historical control or standard reference value or range of values (such as a previously tested control sample, such as a wild type SpdE protein or SpdE protein in the absence of ligand).

Expression: "Expression" refers to transcription and/or translation of a nucleic acid sequence. For example, a gene can be expressed when its DNA is transcribed into an RNA or RNA fragment, which in some examples is processed to become mRNA. A gene may also be expressed when its mRNA is translated into an amino acid sequence, such as a protein or a protein fragment. Regulation of expression can include controls on transcription, translation, RNA transport and processing, degradation of intermediary molecules such as mRNA, or through activation, inactivation, compartmentalization or degradation of specific protein molecules after they are produced.

Germ-free: An animal born and reared in aseptic conditions having substantially no microorganisms living on or in it (for example, substantially no bacteria in the gut of the animal).

Gnotobiotic: An animal in which only known strains of microorganisms are present. For example, a germ-free animal exposed to (e.g., intentionally inoculated with) one or more known bacterial strains is gnotobiotic. Germ-free animals are also gnotobiotic, as their microbial status is known. In contrast, conventionally reared animals (born and raised without absolute control of microorganism exposure) have a microbiota of many, and in most cases hundreds or thousands of organisms, which population will vary from animal to animal.

Heterologous: Originating from a different genetic source or species. For example, a nucleic acid that is heterologous to a cell originates from an organism or species other than the cell in which it is expressed. In one specific, non-limiting example, a heterologous nucleic acid includes an *Aeromonas veronii* nucleic acid that is present or expressed in a different bacterial cell (such as an *E. coli* cell) or in an algal, plant, or mammalian cell. In other examples, a heterologous nucleic acid or protein is one that has a nucleic acid or amino acid sequence that does not naturally occur in the organism (e.g., is a sequence variant compared to that naturally occurring in the organism). Methods for introducing a heterologous nucleic acid into bacterial, algal, plant, and mammalian cells are well known in the art, for example transformation with a nucleic acid, including electroporation, lipofection, and particle gun acceleration.

In another example of use of the term heterologous, a nucleic acid is operably linked to a heterologous promoter from an organism or species other than that of the promoter. For example, an *Aeromonas veronii* nucleic acid may be linked to a heterologous bacterial, viral, or mammalian promoter. In other examples of the use of the term heterologous, a nucleic acid encoding a polypeptide or portion thereof is operably linked to a heterologous nucleic acid encoding a second polypeptide or portion thereof, for example to form a non-naturally occurring fusion protein.

Isolated: An "isolated" or "purified" biological component (such as a nucleic acid, peptide, protein, protein complex, or cell) has been substantially separated, produced apart from, or purified away from other biological components e.g., other chromosomal and extrachromosomal DNA and RNA, proteins, or cells. Nucleic acids, peptides, and proteins that have been "isolated" or "purified" thus include nucleic acids and proteins purified by standard purification methods. The term also embraces nucleic acids, peptides, and proteins prepared by recombinant expression in a host cell, as well as chemically synthesized nucleic acids or proteins.

The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total content of the preparation.

Motility: Motility refers to the ability of an organism or a cell, such as a bacterial cell, to move on its own by expending energy. For example, Aeromonas isolates most commonly achieve motility through a single polar, unsheathed flagellum, although under environmental circumstances that prevent motility using such flagella, some isolates may produce peritrichous lateral flagella that mediate swarming motility. Motility is an important aspect of host colonization by flagellated bacteria, and enhanced motility may lead to increase host colonization. Motility of bacterial cells may be regulated by the presence and/or amount of signaling molecules (e.g., amino acids) in the cellular environment.

Operably linked: A first nucleic acid is operably linked to a second nucleic acid when the first nucleic acid is placed in a functional relationship with the second nucleic acid. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: Remington: The Science and Practice of Pharmacy, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic agents, such as those disclosed herein. In general, the nature of the carrier will depend on the particular mode of administration employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate.

Recombinant: A nucleic acid or protein that is not naturally occurring or has a sequence that is made by an artificial combination of two otherwise separated segments of nucleotides or amino acids. This artificial combination is often accomplished by chemical synthesis or, more commonly, by the artificial manipulation of isolated segments of nucleic acids, e.g., by genetic engineering techniques such as those described in Sambrook et al. Molecular Cloning: A Laboratory Manual, 3$^{rd}$ ed., Cold Spring Harbor Laboratory Press, N.Y., 2001. The term recombinant includes nucleic acids or proteins that have been altered solely by addition, substitution, or deletion of a portion of the nucleic acid sequence or amino acid sequence, respectively.

Sample: As used herein, a sample (for example a biological sample) includes but is not limited to, cells, tissues, and bodily fluids, such as: blood; derivatives and fractions of blood, such as serum; extracted galls; biopsied or surgically removed tissue, including tissues that are, for example, unfixed, frozen, fixed in formalin, and/or embedded in paraffin; autopsy material; tears; milk; skin scrapes; surface washings; urine; sputum; cerebrospinal fluid; prostate fluid; pus; bone marrow aspirates; middle ear fluids; bronchoalveolar lavage; tracheal aspirates; nasopharyngeal aspirates or swabs; oropharyngeal aspirates or swabs; or saliva. A sample may also include environmental samples, for example, soil or water (such as water from ocean or fresh bodies of water) or laboratory samples (such as experimental samples).

Sensor domain-containing diguanylate cyclase (SpdE): SpdE is a previously-uncharacterized transmembrane protein that contains a diguanylate cyclase domain and a small molecule-binding tandem Per-Arnt-Sim (PAS) domain. PAS domains function as signal sensors, and, in SpdE, bind particular amino acids. Intracellular cyclic-di-GMP, the product of diguanylate cyclase activity, is modulated in the presence of particular amino acids in a SpdE-dependent manner. Aeromonas has a SpdE-dependent hyper-motility phenotype modulated by such ligands, and the presence of SpdE ligands increases Aeromonas migration into larval zebrafish gut.

Exemplary SpdE amino acid sequences include SEQ ID NOs: 1 and 5 provided herein and GenBank Accession Nos. AXV21510, ATY79620, and AEB48271, all of which are incorporated herein by reference. Exemplary spdE nucleic acid sequences include SEQ ID NOs: 2 and 6 provided herein and GenBank Accession Nos. CP0288133 (3689243 . . . 3687609, reverse complement), CP024933 (284234 . . . 282600, reverse complement), and CP002607 (263670 . . . 262036, reverse complement), all of which are incorporated herein by reference. Additional SpdE amino acid and nucleic acid sequences can be identified, for example, by similarity searching.

Subject: A living multi-cellular vertebrate organism, a category that includes vertebrates, including human and non-human mammals. In some examples, a subject includes laboratory animals, including mice or zebrafish.

Transduced and Transformed: A virus or vector "transduces" a cell when it transfers nucleic acid into the cell. A cell is "transformed" by a nucleic acid transduced into the cell when the DNA becomes replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule that can be introduced into a host cell, thereby producing a transformed or transduced host cell. Recombinant DNA vectors are vectors including recombinant DNA. A vector can include nucleic acid sequences that permit it to replicate in a host cell, such as an origin of replication. A vector can also include one or more selectable marker genes, a cloning site for introduction of heterologous nucleic acids, a promoter (for example for expression of an operably linked nucleic acid), and/or other genetic elements known in the art. Vectors include plasmid vectors, including plasmids for expression in Gram-negative and Gram-positive bacterial cells. Exemplary vectors include those for use in *E. coli*. Vectors also include viral vectors and vectors for expression in yeast cells or mammalian cells.

II. SpdE Proteins and Nucleic Acids

Disclosed herein are SpdE proteins from the zebrafish microbiome. In one example, the SpdE protein is from *Aeromonas veronii* (e.g., *Aeromonas* ZOR0001). In another example, the SpdE protein is from *Aeromonas caviae* (e.g., *Aeromonas* ZOR0002). The SpdE protein has two domains, a tandem PAS domain and a diguanylate cyclase domain (e.g., FIG. 11A). The tandem PAS domain is in the periplasm and the diguanylate cyclase domain is in the cytoplasm of the cell. As disclosed herein, the tandem PAS domain binds amino acids (such as hydrophobic amino acids with short side chains, e.g., proline, valine, isoleucine, and leucine). As described in Example 4, the distal PAS domain appears to be more important in amino acid binding than the proximal PAS domain. In the absence of ligand, the diguanylate cyclase domain is active. Binding of an amino acid to the tandem PAS domain decreases diguanylate cyclase activity and increases cell motility (e.g., FIGS. 12A and 12E).

In some embodiments, the SpdE protein is a polypeptide the sequence of which includes or consists of the amino acid sequence of SEQ ID NO: 1. In additional embodiments, a SpdE polypeptide disclosed herein has at least 75%, 85%, 90%, 95%, 96%, 97%, 98%, or 99% sequence identity to the amino acid sequence set forth in SEQ ID NO: 1. In other embodiments, the SpdE protein is a polypeptide the sequence of which includes or consists of the amino acid sequence of SEQ ID NO: 5. In additional embodiments, a SpdE polypeptide disclosed herein has at least 75%, 85%, 90%, 95%, 96%, 97%, 98%, or 99% sequence identity to the amino acid sequence set forth in SEQ ID NO: 5. Exemplary sequences can be obtained using computer programs that are readily available on the internet and the amino acid sequences set forth herein. In some examples, the polypeptide retains a function of the SpdE protein, such as binding one or more amino acids or diguanylate cyclase activity.

In other embodiments, a SpdE polypeptide is a variant SpdE that has one or more sequence modifications and one or more changes in SpdE protein function, such as altered amino acid binding properties or altered modulation of diguanylate cyclase activity. Exemplary variants include a nonsense mutation at amino acid 127 (W127*), a nonsense mutation at amino acid 362 (Q362*), a frameshift mutation starting at amino acid 162, a frameshift mutation starting at amino acid 252, and amino acid substitutions A298D, T321S, A363T, W140A, and Y157A (numbering relative to SEQ ID NO: 1). In some examples, the SpdE protein resulting from the frameshift mutation starting at amino acid 162 has the amino acid sequence of SEQ ID NO: 3. In other examples, the SpdE protein resulting from the frameshift mutation starting at amino acid 252 has the amino acid sequence of SEQ ID NO: 4.

In additional embodiments, a SpdE polypeptide includes an amino acid sequence with at least 50% sequence identity (such as at least 50%, at least 53%, at least 55%, at least 60%, at least 65%, at least 70%, at least 75%, at least 85%, at least 90%, at least 95%, at least 96%, at least 97%, at least 98%, or at least 99% sequence identity) with a PAS/dCache domain of a SpdE polypeptide. In particular non-limiting examples, the PAS/dCache domain includes or consists of amino acids 38-286 of SEQ ID NO: 1 or amino acids 43-290 of SEQ ID NO: 5. In particular examples, the SpdE polypeptide retains at least one activity of the SpdE protein, including amino acid binding. Exemplary conserved residues, including predicted amino acid binding sites are shown in FIG. 8D.

In additional embodiments, a SpdE protein disclosed herein is encoded by a nucleic acid sequence which includes or consists of the nucleic acid sequence of SEQ ID NO: 2. In further embodiments, a nucleic acid encoding a SpdE polypeptide disclosed herein has at least 75%, 85%, 90%, 95%, 96%, 97%, 98%, or 99% sequence identity to the nucleic acid sequence set forth in SEQ ID NO: 2 or a fragment thereof. In other embodiments, a SpdE protein disclosed herein is encoded by a nucleic acid sequence which includes or consists of the nucleic acid sequence of SEQ ID NO: 6. In further embodiments, a nucleic acid encoding a SpdE polypeptide disclosed herein has at least 75%, 85%, 90%, 95%, 96%, 97%, 98%, or 99% sequence identity to the nucleic acid sequence set forth in SEQ ID NO: 6 or a fragment thereof. Exemplary sequences can be obtained using computer programs that are readily available on the internet and the amino acid and nucleic acid sequences set forth herein. In some examples, the nucleic acid encodes a polypeptide that retains a function of the SpdE protein, such as binding one or more amino acids, or diguanylate cyclase activity.

In other embodiments, a SpdE nucleic acid encodes a variant SpdE that has one or more sequence modifications and one or more changes in SpdE protein function, such as altered amino acid binding properties or altered modulation of diguanylate cyclase activity. Exemplary variants include deletion of nucleotide 485, deletion of nucleotide 755, G380A, C1084T, C893A, C962G, G1087A, T418G+G419C, and T469G+A470C (numbering relative to SEQ ID NO: 2).

In further embodiments, amino acid sensors including a SpdE amino acid sensing domain linked to a heterologous signaling domain are provided. The heterologous signaling domain in some examples, is a bacterial signaling domain from a bacterial two-component system. In some examples, the signaling includes a histidine kinase which can alter the activity of a bacterial response regulator (see, e.g., FIG. 21B). In one example, a disclosed amino acid sensor includes a SpdE tandem PAS/dCache domain and SpdE transmembrane domains operably linked to an *E. coli* NarQ signaling domain (e.g., HAMP and histidine kinase domains; see, e.g., FIG. 21A). In some examples, the sensor includes or consists of amino acids 1-309 of SEQ ID NO: 1 linked to a signaling domain. In particular examples, the signaling domain includes or consists of amino acids 310-696 of SEQ ID NO: 7. In particular examples, the sensor includes a polypeptide with an amino acid sequence with at least 85% sequence identity (such as at least 90%, at least 95%, at least 96%, at least 97%, at least 98%, or at least 99% sequence identity) with SEQ ID NO: 7 or includes or consists of SEQ ID NO: 7. Also provided are nucleic acids that encode the amino acid sensor. In some examples, the nucleic acid has at least 85% sequence identity (such as at least 90%, at least 95%, at least 96%, at least 97%, at least 98%, or at least 99% sequence identity) with SEQ ID NO: 8 or includes or consists of SEQ ID NO: 8. In other examples, the SpdE tandem PAS/dCache domain is operably linked to a detectable label, such as a fluorescent protein that is engineered to fluoresce only when a conformational change or dimerization is induced upon ligand binding.

In additional examples, the histidine kinase portion of the fusion protein is additionally fused to a first portion of a fluorescent protein (such as one portion of a split fluorescent protein) and the response regulator is fused to a second portion of a fluorescent protein (such as a complementary portion of a split fluorescent protein), such that activation of the histidine kinase recruits the response regulator, bringing together the first and second portions of the split fluorescent protein and generating a detectable fluorescent signal. In another example, the response regulator induces expression of a detectable protein (such as a fluorescent protein). In this example, a nucleic acid encoding the detectable protein would replace lacZ in the system shown in FIG. 21B. In these examples, presence of ligand (such as an amino acid) would result in decreased fluorescent signal compared to in the absence of ligand.

III. Vectors, Modified Cells, and Uses Thereof

Nucleic acid molecules encoding the SpdE protein, variants thereof, or amino acid sensors disclosed herein also include a recombinant DNA which is incorporated into a vector, into an autonomously replicating plasmid or virus, or into the genomic DNA of a prokaryote or eukaryote, or which exists as a separate molecule (such as a cDNA) independent of other sequences. A nucleic acid encoding a SpdE polypeptide (for example SEQ ID NO: 2 or SEQ ID NO: 6, or a variant thereof) is in some examples operably linked to heterologous expression control sequences. An expression control sequence operably linked to a coding sequence is ligated such that expression of the coding sequence is achieved under conditions compatible with the expression control sequences. The expression control sequences include, but are not limited to, appropriate promoters, enhancers, transcription terminators, a start codon (e.g., ATG) in front of a protein-encoding nucleic acid, splicing signal for introns, maintenance of the correct reading frame of that gene to permit proper translation of mRNA, and stop codons. The expression control sequence(s) in some examples are heterologous expression control sequence(s), for example from an organism or species other than the protein-encoding nucleic acid. Thus, the protein-encoding nucleic acid operably linked to a heterologous expression control sequence (such as a promoter) comprises a nucleic acid that is not naturally occurring. In other examples, the nucleic acid is operably linked to a tag sequence (such as 6×His, HA tag, or Myc tag) or another protein-coding sequence, such as glutathione S-transferase or maltose binding protein.

Vectors for cloning and replication of the disclosed nucleic acid molecules include bacterial plasmids, such as bacterial cloning or expression plasmids. Exemplary bacterial plasmids into which the nucleic acids can be cloned include *E. coli* plasmids, such as pBR322, pUC plasmids (such as pUC18 or pUC19), pBluescript, pACYC184, pCD1, pGEM® plasmids (such as pGEM®-3, pGEM®-4, pGEM-T® plasmids; Pomega, Madison, Wis.), TA-cloning vectors, such as pCR® plasmids (for example, pCR® II, pCR® 2.1, or pCR®4 plasmids; Life Technologies, Grand Island, N.Y.) or pcDNA plasmids (for example pcDNA™3.1 or pcDNA™3.3 plasmids; Life Technologies). In some examples, the vector includes a heterologous promoter which allows protein expression in bacteria. Exemplary vectors include pET vectors (for example, pET-21b), pDEST™ vectors (Life Technologies), pRSET vectors (Life Technologies), pBAD vectors, and pQE vectors (Qiagen). The disclosed nucleic acids can be also be cloned into *B. subtilis* plasmids, for example, pTA1060 and pHT plasmids (such as pHT01, pHT43, or pHT315 plasmids). Additional vectors suitable for cloning and/or bacterial expression can be selected.

DNA sequences encoding a SpdE polypeptide or variant can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Transformation of a host cell with recombinant DNA can be carried out by techniques known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

Disclosed herein are host cells that express a heterologous SpdE protein (such as a SpdE protein from another species) or a variant SpdE protein (such as a variant SpdE protein disclosed herein). Also disclosed are modified host cells that do not express a SpdE protein, such as host cells that are deleted for a spdE nucleic acid (e.g., spdE knockout or ΔspdE). Methods of producing spdE knockout strains include allelic exchange (e.g., Wiles et al., *mBio* 9:301877-18, 2018), homologous recombination, recombineering, and CRISPR techniques. In further examples, disclosed are host cells that overexpress a SpdE protein (e.g., host cells that express more SpdE protein than the corresponding wild type host cell).

Host cells can include microbial, yeast, insect and/or mammalian host cells. Non-limiting examples of suitable host cells include bacteria, archaea, insect, fungi (for example, yeast), mycobacterium, plant, and animal cells (for example, mammalian cells, such as human cells). In particular examples, disclosed are bacterial cells that express a SpdE protein or variant thereof, or do not express a SpdE protein (e.g., a spdE knockout strain). Exemplary bacterial cells include *E. coli, Aeromonas veronii, Lactobacillus* sp. (e.g., *Lactobacillus plantarum, Lactobacillus paracasei, Lactobacillus acidophilus, Lactobacillus casei, Lactobaillus rhamnosus, Lactobacillus crispatus, Lactobacillus gasseri, Lactobacillus reuteri, Lactobacillus bulgaricus), Lactococcus* sp. (e.g., *Lactococcus lactis), Bifidobacterium* sp. (e.g., *Bifidobacterium longum, Bifidobacterium catenulatum, Bifidobacterium breve, Bifidobacterium animalus, Bifidobacterium bifidum*), or *Streptococcus* sp. (e.g., *Streptococcus sanguis, Streptococcus oralis, Streptococcus mitis, Streptococcus thermophilus, Streptococcus satavarius*). In one example, the cell is *E. coli* Nissle strain.

In some embodiments, composition including a host cell expressing a heterologous SpdE protein or variant thereof and a pharmaceutically acceptable carrier is prepared. Pharmaceutically acceptable carriers are determined in part by the particular composition being administered, as well as by the particular method used to administer the composition. Accordingly, there is a wide variety of suitable formulations of pharmaceutical compositions of the present disclosure. *Remington: The Science and Practice of Pharmacy*, The University of the Sciences in Philadelphia, Editor, Lippincott, Williams, & Wilkins, Philadelphia, Pa., $21^{st}$ Edition (2005), describes compositions and formulations suitable for pharmaceutical delivery of one or more therapeutic agents Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Compositions for oral administration include powders or granules, suspensions or solutions in water or non-aqueous media, capsules, sachets, or tablets. Thickeners, flavorings, diluents, emulsifiers, dispersing aids or binders may be desirable.

In other examples, the pharmaceutically acceptable carrier can be a food product, including, but not limited to a dairy product, such as milk or yogurt. In some examples, a dried or lyophilized form of the host cell is mixed with the food product.

A pharmaceutical composition including a host cell expressing a heterologous SpdE protein or variant thereof can be administered to a subject. The amount of host cell expressing a heterologous SpdE protein or variant thereof to be administered to a subject can be selected by one of ordinary skill in the art, for example from about $10^6$ to $10^{12}$ cells (such as about $10^6$ to $10^9$ cells, about $10^7$ to $10^{10}$ cells, about $10^8$ to $10^{11}$ cells, or about $10^9$ to $10^{12}$ cells). In some examples, the amount of cells in the composition is about 10 million, about 50 million, about 100 million, about 500 million, about 1 billion, about 50 billion, or about 100 billion cells.

IV. Methods of Detecting Amino Acids

Disclosed herein are methods of detecting presence and/or amount of one or more amino acids in a sample. The methods include contacting a sample with a SpdE protein, measuring diguanylate cyclase activity of the SpdE protein, and comparing the diguanylate cyclase activity of the SpdE protein to a control. The disclosed methods may be performed in vitro or in vivo. In some examples, the method includes detecting the presence and/or amount of one or more of proline, valine, isoleucine, leucine, alanine, methionine, or threonine.

In some embodiments, the methods include contacting a sample with a SpdE protein disclosed herein (e.g., a purified or isolated SpdE protein, such as the SpdE protein of SEQ ID NO: 1 or SEQ ID NO: 5) and measuring diguanylate cyclase activity of the SpdE protein. The diguanylate cyclase activity of the SpdE protein is then compared to a control (including, but not limited to the SpdE protein in the absence of the sample). In some examples, a decrease in diguanylate cyclase activity compared to the control indicates presence of one or more amino acids in the sample. The assay may be qualitative, semi-quantitative, or quantitative. For example, amount of an amino acid could be determined by using standard curves. Similarly, the identity of an amino acid present could be determined based on degree of thermal shift (e.g., using the assay described in Example 4).

Methods of measuring diguanylate cyclase activity include methods for measuring one or more products of diguanylate cyclase activity, such as cyclic-di-GMP and/or pyrophosphate. Diguanylate cyclase produces cyclic-di-GMP by the following reaction:

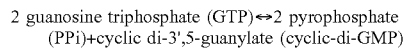

Methods of measuring cyclic-di-GMP include high pressure liquid chromatography (HPLC), thin layer chromatography (e.g., utilizing radiolabeled precursors), mass spectrometry, fluorescent detection (e.g., using thiazole orange, acriflavine, or proflavine), or circular dichroism. In other examples, cyclic di-GMP generation can be measured in vivo (e.g., in a bacterial cell) using a reporter construct with a cyclic di-GMP responsive promotor fused to a bioluminescent or fluorescent enzyme (see, e.g., Pawar et al., *J. Appl. Microbiol.* 120:205-217, 2016; Liu et al., *Bioprotocol*, DOI: 10.21769/BioProtoc.2753). Methods of measuring pyrophosphate include colorimetric assays (such as ENZCHEK® pyrophosphate assay (ThermoFisher Scientific) or malachite green assay), chromogenic or fluorogenic assays (such as PiPer™ pyrophosphate assay (ThermoFisher), Pyrophosphate Assay (Fluorometric) (Abcam), Pyrophosphate Assay (Sigma-Aldrich), or PhosphoWorks™ Fluorometric Pyrophosphate Assay (AAT Bioquest)), or luminescent assays (such as PPiLight™ inorganic pyrophosphate assay (Lonza)). Methods of detecting cyclic-di-GMP and pyrophosphate are reviewed in Stelitano et al. (*Nucleic Acids Research* 41:e79, 2013), incorporated herein by reference in its entirety.

In other embodiments, the methods include contacting a sample with a cell expressing a disclosed SpdE protein (e.g., a cell expressing the SpdE protein of SEQ ID NO: 1 or SEQ ID NO: 5, such as an *Aeromonas* cell) and measuring diguanylate cyclase activity of the SpdE protein. The diguanylate cyclase activity of the SpdE protein is then compared to a control (including, but not limited to the SpdE protein-expressing cell in the absence of the sample). In some examples, diguanylate cyclase activity may be measured as discussed above. In other examples, diguanylate cyclase activity is measured by measuring motility of the cell. In some examples, a decrease in cell motility compared to the control indicates presence of one or more amino acids in the sample.

In some examples, the cell is a bacterial cell expressing a SpdE protein. In particular examples, the cell is an *Aeromonas* cell, such as an *Aeromonas veronii* cell. The *Aeromonas* cell may be a wild type cell, for example, an *Aeromonas* cell expressing an endogenous SpdE protein. In other examples, the *Aeromonas* cell may be a modified cell, such as an *Aeromonas* cell overexpressing a SpdE protein. In other examples, the cell is an *E. coli* cell expressing a SpdE protein.

Methods of measuring cell motility include using semi-solid agar swim plates or tubes, recording and tracking bacterial cells directly via microscopy, and classical capillary assays or modifications thereof. Exemplary methods of measuring bacterial cell motility is described in Example 6.

Also provided are methods of detecting presence and/or amount of one or more amino acids in a sample using a SpdE-signaling domain fusion protein provided herein. The methods include contacting a sample with a SpdE-signaling domain fusion protein, measuring activity of the signaling domain, and comparing the activity of the signaling domain to a control. The disclosed methods may be performed in vitro or in vivo. In some examples, the method includes detecting the presence and/or amount of one or more of proline, valine, isoleucine, leucine, alanine, methionine, or threonine.

In some embodiments, the SpdE-signaling domain fusion protein includes a NarQ signaling domain (e.g., SEQ ID NO: 7). When activated, the NarQ signaling domain auto-phosphorylates, then transfers the phosphoryl group to NarL, a transcriptional activator that binds nitrate-responsive promotors such as narG. In this system a reporter (e.g., LacZ, a β-galactosidase or a fluorescent protein) is under the control of the narG promoter, therefore activation of NarL results in expression of the reporter. Thus, in some examples, the SpdE-NarQ fusion protein is co-expressed in a cell (such as a bacterial cell, for example, an *E. coli* cell) that also expresses NarL and a reporter under the control of NarL. In some examples, the reporter is LacZ and β-galactosidase activity is quantified, e.g., via a colorimetric assay. In other examples, the reporter is a fluorescent protein and fluorescence is quantified. This fusion protein is in an active state in the absence of ligand (as seen for the native SpdE), and reporter activity (e.g., β-galactosidase activity or fluorescence) decreases with increasing ligand concentrations. Thus, in some examples, a decrease in reporter activity compared to a control indicates presence or amount of the ligand, such as an amino acid.

In some embodiments, the SpdE-signaling domain fusion protein includes a signaling domain (e.g., a histidine kinase domain, such as NarQ) and a portion of a split fluorescent protein. When activated, the histidine domain auto-phosphorylates, then transfers the phosphoryl group to NarL, a transcriptional activator that binds nitrate-responsive promotors such as narG. In this system the second portion of the split fluorescent protein is fused to NarL, therefore interaction of NarQ and NarL results in complementation of the split fluorescent protein and fluorescence. Thus, in some examples, the SpdE-NarQ-split fluorescent protein fusion protein is co-expressed in a cell (such as a bacterial cell, for example, an *E. coli* cell) that also expresses a NarL-split fluorescent protein fusion protein. This split, fluorescent protein is in an active state in the absence of ligand (as seen for the native SpdE), and fluorescence decreases with increasing ligand concentrations. Thus, in some examples, a decrease in fluorescence compared to a control indicates presence or amount of the ligand, such as an amino acid.

Appropriate samples for use in the disclosed methods include biological samples, including clinical samples obtained from a human or veterinary subject, environmental samples, and laboratory samples. Suitable samples include biological samples from a subject, including, but not limited to, cells, tissues, autopsy samples, bone marrow aspirates, bodily fluids (for example, blood, plasma, serum, urine, cerebrospinal fluid, middle ear fluids, sputum, or saliva), eye swabs, cervical swabs, vaginal swabs, rectal swabs, stool, and stool suspensions. Suitable samples also include environmental samples, including, but not limited to, food, soil, or water (such as water from saltwater bodies (e.g., ocean or sea), freshwater bodies (e.g., river, lake, creeks, or ponds), or domestic water systems). Suitable samples also include laboratory samples, for example experimental assay samples.

In particular embodiments, the sample is from a subject known or suspected to have a disorder that includes alteration in one or more amino acid levels. In particular non-limiting examples, the sample is a plasma, serum, or urine sample. In some examples, the subject is known or suspected to have insulin resistance, prediabetes, Type 2 diabetes, obesity, maple syrup disease, hyperprolinemia, or irritable bowel disease (e.g., Crohn's disease). In other examples, the subject is known or suspected to have cancer (e.g., glioblastoma, colorectal cancer, non-small cell lung cancer, ovarian cancer, breast cancer, or pancreatic cancer). In still further examples, the subject has chronic obstructive pulmonary disease or liver fibrosis (e.g., liver cirrhosis). The subject is identified as having the disorder if a change in the presence or amount of one or more amino acids compared to a control is detected in the sample. Exemplary disorders and alterations in amino acids are provided in Table 1. If the subject is identified as having the disorder based on alterations in amino acid levels, they can be administered a treatment for the disorder. A skilled clinician can select appropriate treatments, including, but not limited to, dietary modifications (e.g., limiting intake of protein for metabolic disorders), dialysis and/or high glucose intake (e.g., in the case of metabolic crisis), anti-inflammatories, immunosuppressors, and/or antibiotics (e.g., for Crohn's disease), or diet/lifestyle changes, metformin, sulfonylureas, meglitinides, and/or insulin (e.g., for insulin resistance, prediabetes, or diabetes).

TABLE 1

Exemplary disorders with alterations in amino acid levels

| Disorder | Amino Acid Alteration(s) |
| --- | --- |
| Insulin Resistance/ Prediabetes/Type 2 Diabetes/Obesity | Increased valine, isoleucine, leucine, sulfur amino acids, tyrosine, and phenylalanine; decreased glycine |
| Maple Syrup Disease | Increased valine, isoleucine, leucine |
| Hyperprolinemia | Increased proline |
| Crohn's Disease | Depending on type: valine, methionine, leucine, histidine, tryptophan, alanine, tyrosine, glutamine, threonine, serine, glycine; total amino acids, nonessential amino acids, essential amino acids, and branched-chain amino acids. |
| Cancers | Most amino acids, including branched chain amino acids |
| Liver fibrosis | Decreased branched chain amino acids, increased aromatic amino acids |

EXAMPLES

The following examples are provided to illustrate certain particular features and/or embodiments. These examples should not be construed to limit the disclosure to the particular features or embodiments described.

Example 1

Materials and Methods

Ethics statement. All experiments using zebrafish were conducted in compliance with protocols approved by the University of Oregon Institutional Animal Care and Use Committee (IACUC).

Gnotobiotic Zebrafish Husbandry. All zebrafish experiments were conducted following standard protocols and procedures approved by the University of Oregon Institutional Care and Use Committee. Evolution passaging and bacterial competitions were performed using wild type (ABxTu strain) or myd88 mutant zebrafish. The myd88 mutant zebrafish line was previously generated via CRISPR-Cas9 system and verified to have the expected phenotype of an myd88 KO mutant (Burns et al., *Proc. Natl. Acad. Sci. USA* 8:201702511-6, 2017). Fish were maintained as previously described (Westerfield, *The Zebrafish book. A Guide for the Laboratory Use of Zebrafish (Danio rerio)*, Univ. of Oregon Press, 2000), and not fed in any of the experiments described here. Germ free derivation of fish embryos followed protocols previously described (Melancon et al., Meth. Cell Biol. 138:61-100, 2017). Generally, fish were inoculated with bacterial cultures at 4 days post fertilization (dpf). At 7 dpf, fish were euthanized with tricaine (Western Chemical, Inc.) following approved procedures, mounted in sterile 4% methylcellusose solution (Fisher), and the intestines removed by dissection (described in Milligan-Myhre et al., Meth. Cell Biol. 105:87-116, 2011) and used for enumeration of colonizing bacteria or as inoculum for GF fish. Conventional (CV) fish were generated by collecting unwashed embryos into crossing-tank water, sorting into flasks containing sterile EM, then inoculating each flask with about 500 µl of parental tank water.

Bacterial Strains. This study used the bacterial zebrafish isolates Aer01 (*Aeromonas veronii* ZOR0001; BioProject Accession PRJNA205571) and Aer02 (*Aeromonas caviae* ZOR0002; BioProject Accession PRJNA205572). Variants of Aer01 were generated. Briefly, markerless, in-frame deletion of spdE (ΔspdE) was generated by allelic exchange method, using the pAX1 allelic exchange vector (Wiles et al, *MBio* 9:e01877-18, 2018). Chromosomal insertions were used to generate fluorescently-tagged (dTomato or superfolder GFP) Aer01 strains, complement ΔspdE with wild-type spdE (ΔspdE_comp), spdE evolved allele (1 bp deletion at nt 485; ΔspdE_comp$^{evol}$), or Aer02 spdE (ΔspdE_comp$^{Aer02}$), and over-express wild-type spdE in wild type Aer01 (WT$^{anc}$_OE). For insertions, a cassette containing the insertion gene under the control of the native promotor (complemented strains) or CP25 constitutive promotor (WT$^{anc}$_OE, fluorescently-tagged strains) and a gentamycin resistance gene was integrated in the chromosome at a specific target location (attTn7). All genetically-modified strains were assayed for in vitro growth deficiencies in TSB broth; no overt fitness defects were detected.

Evolution Experiment. Evolution passaging was initiated using an equal mixture of dTomato- and sfGFP-tagged ancestral strains, as a means of detecting gain-of-fitness lineages throughout the experiment, an experimental evolution approach previously described by Reyes et al (*Front. Microbiol.* 3:198, 2012). Three replicate lines were passaged in WT (AB×Tu) zebrafish and two replicate lines were passaged in myd88 mutant zebrafish. In all replicate lines, the dTomato-tagged lineages became dominant in the evolving populations by the end of the experiment and all of the evolved isolates described herein descended from this ancestral strain. This could be suggestive of either a small fitness advantage in this genome, a small fitness defect in the sfGFP-tagged ancestral strain, or that the emergence of gain-of-fitness mutants arose in the dTomato lineage in all lines by chance.

The first passage was inoculated by pelleting 1 ml TSB overnight cultures of dTomato- and sfGFP-tagged strains, resuspending them in 1 ml sterile EM, mixing them 1:1, then adding them to replicate flasks of 4 dpf GF larval zebrafish (10-15 larval fish, 15 ml embryo medium) to a final concentration of about $10^6$ CFU/ml. Inoculated fish were incubated according to IACUC protocol. At 7 dpf, fish were euthanized with tricaine and the intestines removed by dissection. Whole intestines from all fish in a flask were combined into a single 1.6 ml tube containing 500 µl sterile embryo medium (EM) and ~100 µl 0.5 mm zirconium oxide beads (Next Advance, Averill Park, N.Y.), then homogenized using a bullet blender tissue homogenizer (Next Advance, Averill Park, N.Y.; 30 seconds, power 4). Evolving *Aeromonas* populations were monitored by dilution plating a small aliquot (20 µl) of the combined gut sample, and an aliquot of the flask medium, on TSA plates. These were incubated at 30° C. for 24 hrs, then the colonies counted and recorded. Half (~250) µl of each homogenate was mixed with 250 µl of sterile 50% glycerol, then stored at −80° C. The remaining homogenates were stored at 4° C. for 4 days, then used as inocula for the subsequent flasks of 4 pdf GF fish. For subsequent inoculations, all ~200 µl of the 4° C. sample was added to the next flask of fish (resulting in ~$10^4$ CFU/ml at the beginning of the passage). This passaging protocol was repeated for 20 passages total for all five lines.

Colony-purification of evolved isolates. Cryopreserved stocks of whole populations from selected evolution passages (5, 10, 15, and 20) were streaked for isolation on TSA plates, then incubated at 30° C. for 1 day. Isolated colonies were randomly picked from the plates into 5 ml TSB cultures, allowed to grow shaking at 30° C. for ~6 hrs, then cryopreserved in 25% and stored at −80° C.

Genomic sequencing and analysis. Genomic DNA was extracted from overnight cultures (TSB) of evolved isolates and the ancestral strain using a Promega Wizard® genomic DNA purification kit (Promega, Madison, Wis.). DNA samples were quantified using the Quant-iT™ dsDNA HS kit (Thermo Fisher) and normalized to 0.2 ng/µL Sequencing libraries were prepped using a Nextera™ XT Library Prep Kit (Illumina; FC-131-1096), according to the manufacturer's protocol. Pooled sample was made by combining 80 ng of prepped library for each sample, and sequenced on an Illumina HiSeq 4000 (single end, 150-bp). Each sample averaged 6.2M reads. Processed reads were aligned and analyzed against the Aer01 reference genome (*Aeromonas veronii* ZOR0001; BioProject Accession PRJNA205571) using breseq (Deatherage et al., *Meth. Mol. Biol.* 1151:165-188, 2014) with default settings; mean coverage of 102× per genome.

Bacterial competitions in vivo. For in vivo bacterial competitions, strains (purified evolved isolates, or Aer01 genetic variants) were grown overnight in TSB from freezer stocks. 1 ml of the overnight cultures were pelleted (8,700 rcf, 2 min), then resuspended in 1 ml sterile EM. Competing strains were mixed, then added to flasks of 4 dpf GF (or CV fish) WT fish at ~$10^6$ CFU/ml. For all competitions, sfGFP-tagged Aer01 was used as the "reference" strain. For competitions where SpdE ligands (amino acids) were added, a 100 mM stock solution of amino acid (proline, valine, glycine (BioUltra, Sigma-Aldrich)) was prepared in water (filter-sterilized; stored at 4° C. for up to a month), then added to the inoculum and fish flask to the desired final concentration (1 mM, 100 nM, 10 nM, as indicated in figure legends), and allowed to incubate at room temperature for 30 min to allow Aer01 to respond to ligand before inoculation of the flasks. At 7 dpf, fish intestines were dissected as described above, and each intestine transferred into a 1.6 ml tube containing 500 µl sterile EM and ~100 µl bullet beads, then bullet blended as described above. Homogenized samples were diluted appropriately in sterile EM, spread plated on TSA plates, incubated at 30° C. for 1-2 days, and the colonies counted. Strains were differentiated by fluorescence microscopy. Competitive index (CI) was calculated by dividing the strain ratio (test strain divided by reference strain) in the gut at the end of the competition by the strain ratio in the inoculum ((test/reference)$_{gut}$/(test/reference)$_{inoculum}$) (FIG. 1). The limit of detection is 5 CFU/gut; for samples were one strain was below the limit of detection, the abundance was set to 5 CFU in order to calculate a CI; this was the case for few of the samples.

Gavage experiments. A previously described gavage protocol (Cocchiaro et al., *J. Vis. Exp.* 72:e4434, 2013) was utilized, with the following modifications. Gavage needles were produced by pulling 3.5" capillaries (Drummond #3-000-203 GIX), then microforging them to an internal diameter of ~30 μm (DMF1000, World Precision Instruments), and polishing the ends. To prepare the gavaging inoculum 1 ml of TSB overnight cultures was pelleted (8,700 rcf, 2 min), then resuspended in 1 ml sterile EM, and competing strains were mixed ~1:4 (competitor:reference); Ancestor (dTomato-tagged) or evolved isolates were competed against the differentially-tagged non-mutator ancestral strain, sfGFP-tagged. Culture mixes were then diluted 1:10 in sterile EM for gavage. Prepared inocula were incubated at room temperature until gavaging and flask inoculation (~30-60 minutes), allowing time for acclimation to the EM. Anesthetized fish (GF, 5 or 6 dpf) were transferred to 3% methylcellulose-coated gavage mold (4% agar). Gavage needles were loaded with culture mix and 4.6 nL was gavaged directly into the lumen of the gut of individual fish using a Nanoject II (Drummond Scientific Company). Fish were rinsed post-gavage in sterile EM, then transferred into a flask containing sterile EM. Immediately after gavaging, flasks of GF fish were inoculated at $10^6$ CFU/ml with the same inocula used for gavaging. At ~5 hrs post-gavage fish were euthanized with tricaine, dissected, and the guts plated as described above to enumerate Aer01 competing strains (FIG. 2).

Figure 3:
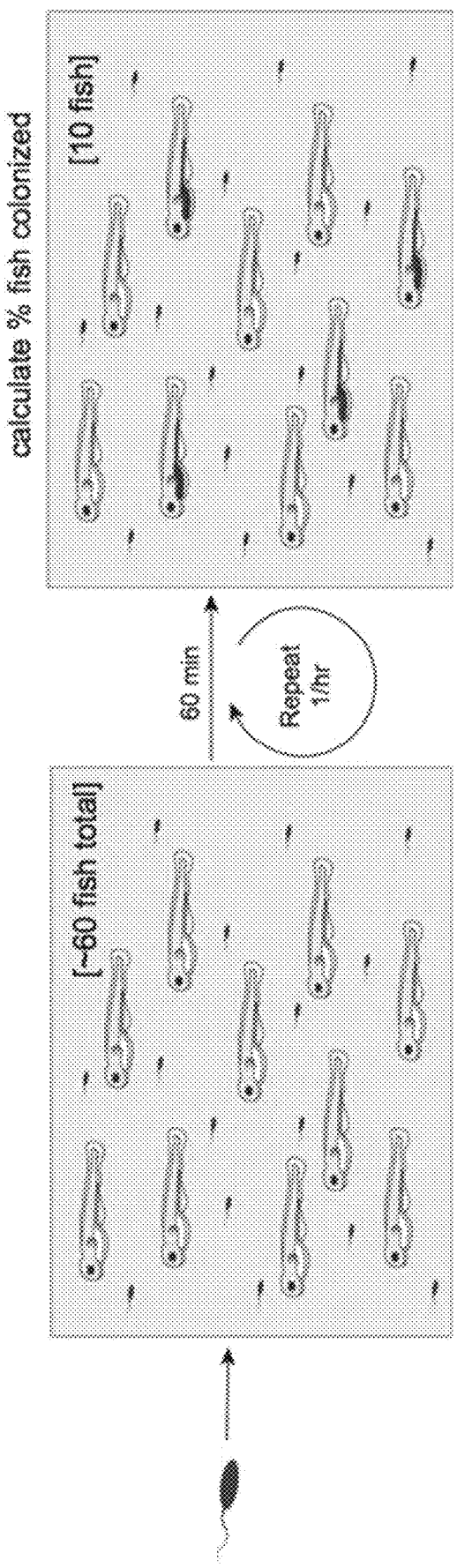
FIG. 3 is a schematic diagram of an immigration experiment.

Migration rate experiments. Strains were grown, shaking, overnight in TSB, at 30° C. Overnight cultures were pelleted and washed in sterile EM, then diluted to 1:100 in sterile EM, and incubated at room temperature for ~2 hrs. If amino acid SpdE ligands were tested, amino acids were added to the prepared inoculum and fish flasks before the 2 hr incubation. GF zebrafish (5 or 6 dpf) inoculated with the cultures to yield ~$10^5$ CFU/ml. The fish were then split into replicate flasks containing 10 fish and 10 ml inoculated flask EM. An EM sample was taken and plated immediately to quantify CFU/ml of the inoculating strain. Subsequently, a replicate flask of fish for each conditions was dissected every ~60 min (for four time points) and the guts individually homogenized as described above in 200 μl sterile EM, and all 200 μl was spread plated on TSA plates (FIG. 3). Flask EM samples were also plated to enumerate bacterial CFU/ml at each time point. After 24-48 hr incubation, colonies on plates were counted.

Fish-to-fish transmission assay. At 4 dpf, flasks of GF larval zebrafish were mono-associated with either WT or AspdE Aer01. At 5 dpf, two mono-associated fish ('donors') were washed 6 times with sterile EM, then transferred into flasks containing 10-15 5 dpf GF larval zebrafish ('recipients'). Fifteen hours later, all fish in the flasks were dissected and the guts homogenized and plated to enumerate Aer01 in the fish. Donor fish could not be distinguished from recipient fish, so these data are combined.

Thermofluor Assay. The periplasmic portion of SpdE was cloned, expressed and purified in *E. coli*. Thermofluor assays were performed using a Thermo Fisher Scientific StepOnePlus Real-time PCR instrument. Each 20 μL sample contained 0.1 mg/mL SpdE protein, 4×SYPRO Orange dye, 165 mM NaCl, 80 mM Tris pH 7.5 and 10 mM ligand (free amino acid dissolved in water). All samples were done in triplicate and repeated 2-3 times on different days. All reagents and steps were performed at 4° C. and placed in 96 well PCR plates. The PCR plate was slowly heated (~0.03° C./sec) from 4° C. to 80° C. in the StepOnePlus instrument and fluorescent measurements were taken every 8.5 sec. The resultant thermal shift curves were analyzed to find the inflexion points, which correspond to the melting temperature ($T_m$) of the protein (with or without ligand). Inflexion points were determined in Microsoft Excel by calculating the half way point between the minimum fluorescence value prior to fluorescence increase and the maximum fluorescence value. The $T_m$ difference between protein with and without ligand was calculated and plotted to determine the thermal stability shift as a proxy for ligand binding.

Aer02 SpdE tandem PAS/dCache crystallization and x-ray collection. SpdE tandem PAS/dCache was crystallized at 22° C. using the hanging drop method in 80 mM sodium acetate trihydrate pH 4.5 and 1.4-1.5 M sodium formate. The reservoir solution was mixed 1:1 with 1 μL of 5 mg/mL SpdE protein in 50 mM Tris pH 7.5 and 300 mM NaCl and suspended above 1 mL of reservoir solution. Crystals were briefly transferred to a cryoprotection solution including the reservoir solution, 10 mM proline and 20% glycerol and flash frozen in liquid nitrogen. Several native diffraction data sets of SpdE tandem PAS/dCache domain were collected using the Advanced Light Source at the Berkeley Center for Structural Biology. We use beamline 5.0.2. at 1 Å wavelength on a Pilatus detector.

Aer02 SpdE tandem PAS/dCache data processing and structure determination. Diffraction data for three frozen crystals (137_10, 137_13 and 137_14) were indexed and processed using the HKL2000 suite (Otwinoswki et al., *Meth. Enzymol.* 276:307-326, 1997). The resulting evaluation statistics are reported in Table 2. For crystals 137_10 and 137_13, systematic absence patterns were identified, leading to identification of the crystallographic space group as P4122 or P4322 with 97% confidence, but were less clear for 137_14. However, the merging statistics for crystal 137_14 were better, and intensities along the h and k axes were weak, so we could not be entirely confident in the identification. Data from crystal 137_14 were processed to 2.0 Å resolution in space group P422 and data were judged to be of reasonably high quality at a nominal resolution of 2.4 Å. The space group ambiguity was left for molecular replacement searches to resolve. Amino acid homology searches(Soding, *Bioinformatics* 21:951-960, 2005; Zimmermann et al., *J. Mol. Biol.* 430:2237-2243, 2018) identified 19 atomic models as structural homologs to the ligand binding domain of Aer02 SpdE in the Protein Data Bank, albeit with weak (15-20%) sequence identity, so molecular replacement was used in the structure solution. The Phenix crystallographic package (Adams et al., *Acta Crystallogr. D Boil. Crystallogr.* 66:213-221, 2010) was used to conduct molecular replacement (MR) searches. Search models included the top six hits identified using the HHPred server (Zimmermann et al., *J. Mol. Biol.* 430:2237-2243, 2018) with PDB ID codes (3C8C, 3LIF, 4XMR, SLTV, SLTX and 6IOU). Numerous initial experiments using unmodified models, and models modified in various ways (polyalanine backbone, loops truncated, etc.) failed to yield interpretable MR solutions. So, the Rosetta program package was utilized in concert with Phenix (mr_rosetta; DiMaio et al., *Nature* 473:540-543, 2011) to build a large number of hypothetical models based on the six homologs identified above. In a typical step of this procedure, 5,000 to 10,000 different models are constructed by the Rosetta package, based on the Aer02 SpdE target amino acid sequence and the provided atomic model, and each resulting model is subjected to a fast MR search by Phenix. The results are sorted and surviving models can be optionally rebuilt using an automated model building procedure. In total, approximately 70,000 models (20,000 CPU hours, using six nodes in parallel with 32 CPUs each) were constructed on the University of Oregon High Performance Talapas cluster. The effort resulted in a single viable solution, based on a single Rosetta derivative of the 3C8C model, which ultimately proved to be correct. This solution verified the space group assignment to be P4122, with Rwork/Rfree 0.44/0.55 at 2.0 Å resolution. Eleven other candidates were identified by the search procedure, but all had incorrect space group assignments and all had Rwork/Rfree of 0.48/0.55 or higher. Although the mr_rosetta search procedure did identify the correct MR solution, it is computationally extremely inefficient. It proved difficult to verify that the 3C8C solution was in fact correct, as initial automated model building and refinement met a dead end. Automated model building failed to lower the R-factor below 0.43, or to add missing segments to the model. The electron density maps were generally uninterpretable in terms of new features, however manual inspection of the model and map revealed that the Rosetta/Autobuild step had incorrectly reinterpreted several segments of the electron density map.

To correct the error, the Rosetta/Autobuild model was discarded in favor of the Rosetta-derived MR solution. That starting model was subjected to the Phenix morph_model procedure, then the map and model were inspected and the model truncated to remove incorrectly placed loops. Another round of morph_model, followed by a conventional autobuild cycle resulted in Rwork/Rfree of 0.417/0.529 and was clearly correct. Several additional cycles of model alterations by hand, using Coot (Emsley et al., *Acta Crystallogr. D Biol. Crystallogr.* 66:486-501, 2010; Emsley et al., *Acta Crystallogr. D Biol. Crystallogr.* 60:2126-2132, 2004), and conventional crystallographic refinement with Phenix led to a reasonable complete model with satisfactory R values at nominal resolution 2.4 Å. For the final steps of crystallographic model building and refinement, a better quality diffraction data set, 99.4% complete to 1.8 Å resolution, was obtained by merging the data from crystals 137_10 and 137_14 (Table 2). Final crystallographic model statistics were satisfactory and are summarized in Table 2. The final model of Aer02 SpdE comprises one continuous polypeptide chain, complete for residues 44-280. Weak electron density is apparent for addition residues at either end, but could not satisfactorily be interpreted either by hand or by automated model building, so these segments were assumed to be flexible. A single proline residue (not included in the crystallization mixture) was very clearly identified as bound to a tight pocket within the distal PAS/Cache domain, and a bound glycerol molecule was identified at the interface between the proximal and distal PAS/Cache domains.

TABLE 2

| Crystallography Data collection and refinement statistics | | | |
|---|---|---|---|
| Data Collection | | | |
| Crystal | 137_14 | 137_10 | 137_13 |
| Total observations | 959,280 | 2,435,866 | 2,162,183 |
| Unique reflections | 19,670 | 26,773 | 23,349 |
| Space Group | P4$_1$22 | P4$_1$22 | P4$_1$22 |
| Cell dimensions (a, b, c; Å) | 86.2, 86.2, 74.9 | 86.4, 86.4, 75.3 | 86.2, 86.2, 75.1 |
| Resolution (Å) | 50.0-2.00 | 50.0-1.80 | 50.0-1.80 |
| Highest resolution shell (Å) | 2.03-2.00 | 1.83-1.80 | 1.83-1.80 |
| Completeness$^a$ (%) | 97.3 (73.3) | 99.3 (64.1) | 87.4 (36.0) |
| Multiplicity$^a$ | 21.9 (9.8) | 22.7 (13.4) | 20.2 (7.0) |
| Average I/σ(I)$^a$ | 7.2 (2.3) | 35.3 (0.2) | 30.3 (0.1) |
| $R_{merge}^{a,b}$ | 0.054 (NR) | 0.081 (6.6) | 0.075 (2.2) |
| Rpim$^c$ | 0.018 (0.343) | 0.023 (2.6) | 0.016 (0.67) |
| CC1/2, CC* (highest shell)$^c$ | 0.458, 0.793 | 0.118, 0.459 | 0.289, 0.669 |
| Merged data 137_10 + 137_13 | 50.0-1.80 Å | (1.83-1.80) Å | |
| Cell dimensions used | 86.19, 86.19, 75.08 | | |
| Number of reflections | 26,663 | 1,332 | |
| $R_{merge}$, $R_{meas}$, $R_{pim}$ | 0.063, 0.089, 0.064 | 2.1, 3.0, 2.1 | |
| CC1/2, CC* | 0.990, 0.997 | 0.208, 0.586 | |
| Refinement (Model 68) | | | |
| Number of molecules/ASU | 1 | | |
| Number of protein atoms | 1903 | | |
| Number of solvent atoms | 31 | | |
| Resolution range (Å)$^d$ | 30.5-1.8 | | |
| Crystallographic $R_{work}$ (reflns)$^e$ | 0.235 (25,331) | | |
| $R_{free}$ (reflns)$^e$ | 0.265 (1201) | | |
| Real Space correlation (CC) | 0.747 | | |
| Average B-factors (Å$^2$) | | | |
| Protein atoms | 58.2 | | |
| Solvent | 58.1 | | |
| RMS deviations from ideality | | | |
| Bond lengths (Å) | 0.013 | | |
| Bond angles (°) | 1.3 | | |

$^a$Values in parentheses indicate statistics for the highest resolution shell.
$^b$R$_{merge}$ = Σ|I − <I>|/Σ<I>, where I is the observed intensity, and <I> is the average of intensities obtained from multiple observations of symmetry related reflections. NR = not reported by HKL2000
$^c$For definitions of R$_{pim}$, CC1/2, CC* (Karplus et al., *Curr. Opin. Struct. Biol.* 34: 60-68, 2015)
$^d$Resolution used in model refinement
$^e$R$_{work, free}$ = Σ||F$_o$| − |F$_c$||/Σ|F$_o$|, where F$_o$ and F$_c$ are the observed and calculated structure amplitudes, respectively.

Live imaging and quantification of Aer01 motility. To perform slide-based, wet mount live imaging of Aer01, sfGFP-tagged Aer01 was grown overnight in 5 ml of TB at 30° C. Cells were centrifuged at 1500 rcf and washed twice with sterile EM. Washed cells were diluted to OD 0.2 and 100 µL of cells were dispensed into a sterile 96 well tray. EM containing proline or valine (pH adjusted to 7.8 with HCl/NaOH) was added to the wells to generate the desired final concentrations of amino acid (0.1 nM, 10 nM, 100 nM, 1 or 1 mM) and cell densities of OD 0.1, each performed in triplicate. The tray was covered by parafilm and incubated at 30° C. for 5 hours. Cells were imaged between hour 5-6. Prior to imaging, bacterial samples were moved to a temperature-controlled box housing the microscope, heated to 30° C. 2 ul of bacteria from treatments were applied to a well slide (MP Biomedicals 10-well multitest slides #096041805), covered with a coverslip, and imaged immediately. Videos of bacteria were captured using a Nikon Eclipse Ti inverted microscope on the GFP channel using 20× magnification at 39 frames per second. Videos of treated bacteria were analyzed with particle tracking software (Parthasarathy, *Nature Methods* 9:724-236, 2012) using these settings: "objects" were identified using bpfilter 3, nsize 7, and gradobjsize 0. A standard threshold of 3.99-6 was applied, depending on the degree of background. Motile bacteria were defined as objects tracked over at least 1 s (39 frames) with a standard deviation in position of pixels/frame of at least 1.

For light-sheet microscope-based imaging and determination of cellular swim speeds, overnight cultures (TSB) of strains (dTomato-tagged Aer01 and dTomato-tagged AspdE) were washed twice with sterile EM, as above. To 2 ml sterile FC-EM (fish-conditioned EM)±1 mM proline, 50 µL of the cultures was added and incubated at 30° C. for ~4 hours to recover and acclimate. FC-EM was generated by collecting the flask EM of GF 5 or 6 dpf zebrafish larvae, filter-sterilizing and storing at 4° C. A glass cuvette was filled with culture and imaged on a custom-built light sheet fluorescence microscope, as previously described (Taormina et al., *Biol. Bull.* 223:7-20, 2012). The light sheet optically sections bulk samples in the center of the cuvette, so as not to constrain the motility of the imaged bacteria by surfaces. Movies in a single optical plane were captured for a duration of 20 seconds (frame rate of 30 frames/sec) with excitation light provided by a 561 nm solid state laser (Coherent Sapphire 20 mW; all strains expressed dTomato fluorescent protein). For each strain and condition, four movies were recorded from randomly selected regions throughout the cuvette (three for WT+proline). As above, particle tracking software, which uses a radial-symmetry-based algorithm, was used to analyze images (Parthasarathy, *Nature Methods* 9:724-726, 2012). The following parameters were used: bpfiltsize=7, nsize=7, gradobjsize=7, 1/nhood=true. Tracks were culled using very stringent criteria in an effort to capture accurate cellular swim speeds. Only tracks with minimum length of 30 frames (tracked for 1 sec) were included, resulting in the number of included tracks in the range of 50-308.

Intracellular cyclic di-GMP quantification. Overnight cultures (TSB) of Aer01 strains were pelleted (2 mL), washed once with sterile EM, and resuspended sterile EM (±1 mM proline, valine, or glycine) to a final volume of 8 mL. Cultures were incubated, shaking, at 30° C. for 4 hours. Sample OD600 was measured and the entire volume pelleted. Sample pellets were resuspended in 300 µL ice cold extraction buffer (40/40/20 acetonitrile/methanol/water+0.1 N formic acid), iced for 30 min, then pelleted at maximum speed in tabletop microcentrifuge for 10 min. The supernatant was transferred to a new tube and stored at −80° until being vacuum concentrated until completely evaporated.

Dried samples were resuspended in 100 µL Ultra Performance liquid chromatography-grade water and centrifuged for two minutes at 18,000×g (Eppendorf® Centrifuge 5242R). The debris-free supernatants were moved to LCMS Certified Clear Glass 12×32 mm screw neck max recovery vials (Waters®). Ten microliters of each sample were analyzed using LC-MS/MS on a Quattro Premier XE mass spectrometer coupled with an Acquity Ultra Performance LC system (Waters®). Cyclic di-GMP was detected with electrospray ionization using multiple reaction monitoring in negative-ion mode at m/z 689.16→344.31. The mass spectrometer parameters were: capillary voltage, 3.5 kV; cone voltage, 50 V; collision energy, 34 V; source temperature, 110° C.; desolvation temperature, 350° C.; cone gas flow (nitrogen), 50 L/h; desolvation gas flow (nitrogen), 800 L/h; collision gas flow (nitrogen), 0.15 mL/min; and multiplier voltage, 650 V. Chromatography separation was done using a reverse phase Waters BEH C18 2.1×50 mm column with a flow rate of 0.3 mL/min with the following gradient of solvent A (10 mM tributylamine plus 15 mM acetic acid in 97:3 water:methanol) to solvent B (methanol): t=0 min; A-99%:B-1%, t=2.5 min; A-80%:B-20%, t=7.0 min; A-35%:B-65%, t=7.5 mM; A-5%:B-95%, t=9.01 min; A-99%:B-1%, t=10 min (end of gradient). Chemically synthesized c-di-GMP (Axxora) was dissolved UPLC-grade water at concentrations of 250, 125, 62.5, 31.25, 15.62, and 7.81 nM to generate a standard curve for calculating the c-di-GMP concentration in each extract. For normalization across samples, the c-di-GMP concentration for each sample was divided by the OD600 of the cultures.

Exploration Assay. Overnight cultures (TSB) of Aer01 Strains were pelleted (1 mL), and resuspended in 1 ml sterile EM. Two mL of the appropriate media (sterile EM (±1 mM proline, valine, or glycine), or FC-EM (collected from either GF or CV fish)) was added to small glass culture tubes and 100 µL of the washed culture was added. The cultures were incubated, shaking, at 30° C. for 3 hours. An aliquot of each culture was passed through a 0.2 µM filter (Corning® Costar® Spin-X® centrifuge tube filters) to generate cell-free supernatant. To a sterile 96-well plate round-bottom plate, 80 µL of unfiltered culture was added to each well to include five replicates for each condition. To another sterile 96-well plate round-bottom plate, 80 µL of the cell-free supernatant was added to each well to replicate the layout of the culture plate. Using a Rainin Liquidator™ 96-channel benchtop pipettor, 5 µL of the cell-free supernatant was pulled up into 20 µL Rainin pipette tips. These tips then were lowered down into the wells of the culture plate so the tips were submerged to half the depth of the culture volume in the wells. This set-up was incubated at room temperature for 30 min, during which time the cells in the culture can swim up into the supernatant in the pipette tips. After incubation, the contents of the tips were ejected into the wells of a sterile 96-well plate (Corning, flat-bottom, #3595) to which 195 µL of sterile TSB medium was added to each well. This plate was immediately placed in a FLUOstar Omega microplate reader (BMG Labtech, Offenburg, Germany) and growth curves monitored by measuring absorbance (600 nm) every 10 min for 12-16 hrs, with 30° C. incubation and constant shaking. The growth curves were plotted and the times at which the absorbance passed 0.5 was determined for each plot. The time difference between a particular condition and a reference condition (as indicated in FIG. 5C) represents the "exploration response" of Aer01 in that condition.

Biofilm Assay. Overnight cultures (TSB) of Aer01 Strains were pelleted (1 mL), and resuspended in 1 mL (equal volume) of the appropriate media (sterile EM±1 mM proline or valine). To the wells of a sterile 96-well plate (Corning, flat-bottom, #3595), 150 µL of each resuspended culture was added, in triplicate. A blank control well was added for each condition using the appropriate uninoculated media. This plate was incubated at 30° C., stationary, for 48 hours. After incubation, the biofilms were quantified using a standard crystal violet biofilm staining procedure. For Aer01, the majority of the biofilm forma at the air-liquid interface (pellicle biofilm). Briefly, the supernatant was removed from each well, then the wells gently rinsed three times with 150 μL sterile EM. Then, 150 μL 0.1% crystal violet was added to each well and the plate was incubated at room temperature for 10 minutes, followed by five rinses with 150 μL sterile EM. To destain, 150 μL 95% ethanol was added to each well and the plate was incubated at room temperature for 10 minutes. Each well was mixed well and the contents transferred to a clean 96-well plate and the absorbance (570 nm) was read on a FLUOstar Omega microplate reader (BMG Labtech, Offenburg, Germany).

Example 2

Evolution of Gut-Associated *Aeromonas* in Zebrafish

Previous studies defined many of the colonization parameters and growth dynamics of the zebrafish bacterial gut symbiont, *Aeromonas* ZOR0001, hereafter referred to as Aer01 (Robinson et al., *PLoS Biol.* 16:e2006893, 2018). For the current study, non-mutator (having the wild-type mutation rate) Aer01 populations were passaged through two genotypes of germ-free (GF) larval zebrafish—wild type (three replicate lines), and myd88$^{-/-}$ immunodeficient (two replicate lines). For each passage, clonal Aer01 populations were added to the flask medium (embryo medium; EM) of groups of 10-15 GF zebrafish larvae at 4 days post fertilization (dpf). At 7 dpf the gut-associated Aer01 populations in each flask of fish were collected via dissection and homogenization, and used as inoculum for the subsequent flask of GF fish. A portion of the homogenized samples was also cryopreserved for isolation and characterization of evolved isolates. Each replicate line was passaged 20 times.

Figure 4:
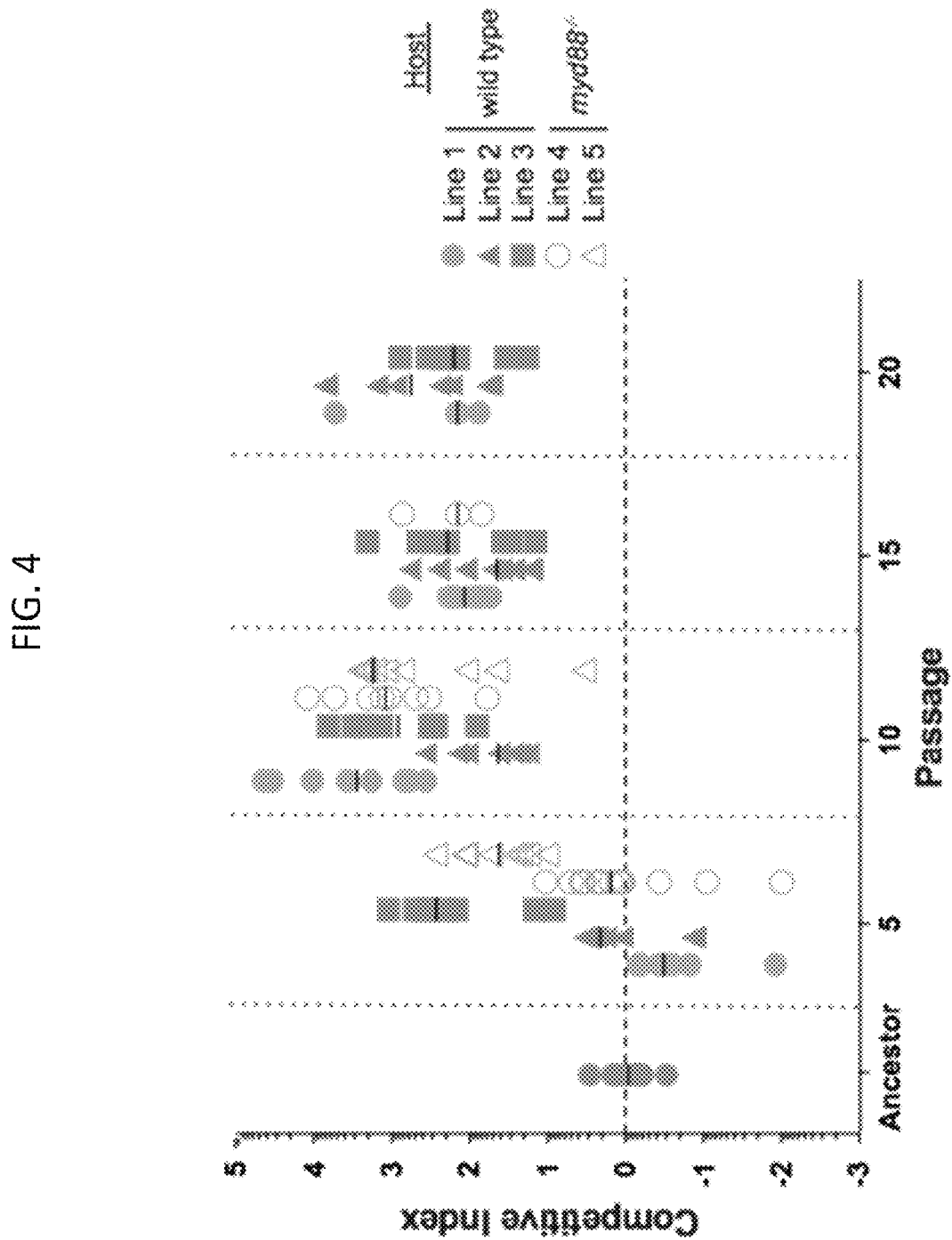
FIG. 4 is a graph showing competitive indices of ancestral and evolved isolates across evolutionary time.
Figure 5:
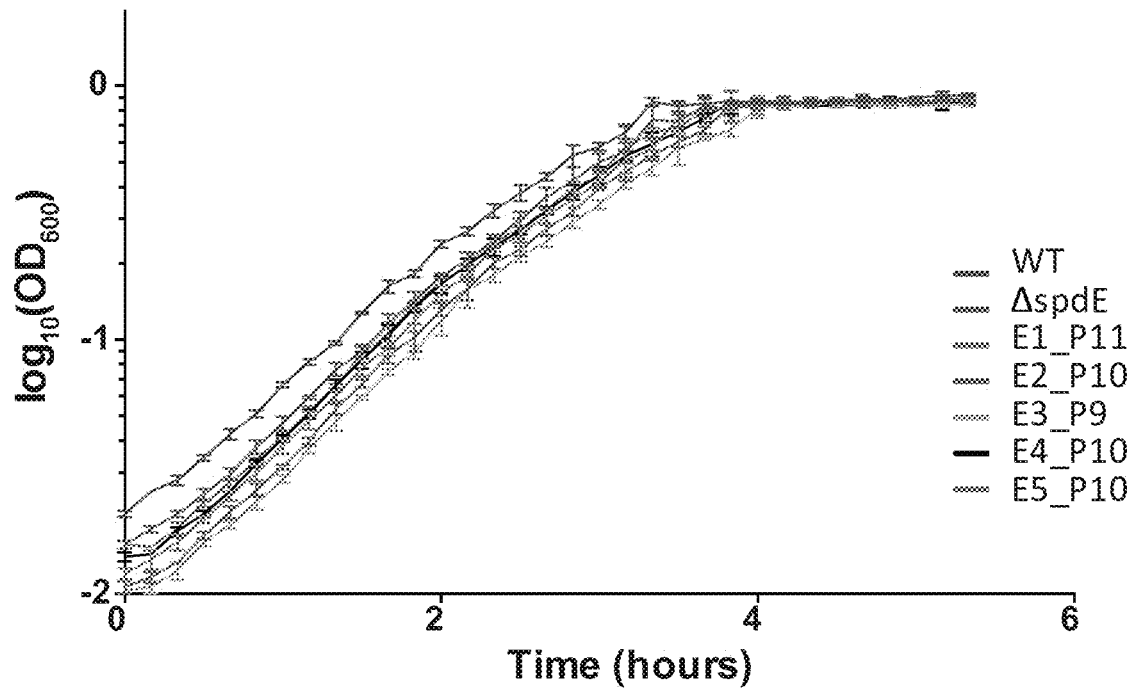
FIG. 5 is a graph showing control TSB growth curves. For the plots, E designates the evolved line from which the isolate is derived and P designates the passage number of the isolate.

In order to isolate and characterize Aer01 isolates from evolving populations in each replicate line, samples from passage 5, 10, 15, and 20 were streaked and grown on rich media. Colony-purified isolates from each population were randomly selected and cryopreserved. Adaptation was assayed for by competing these isolates against a differentially-tagged Aer01 reference strain. Competitions were conducted similar to an evolution passage, where the reference and competing strains (ancestor or evolved isolate) were mixed, inoculated into the flask EM, allowed to colonize for 3 days (4-7 dpf), then the guts were dissected and plated to enumerate abundances of each competitor (FIG. 1). A competitive index (CI) of the competing strain (relative to the reference strain) was calculated for each fish by dividing the strain ratio (competitor:reference) in the intestine by the strain ratio in the inoculum. Adaptation occurred quickly, as CIs were significantly higher than the ancestor by passage 5 in two lines (2 and 5), and in all replicate lines by passage 10 (FIG. 4). These CIs, which are in the range of 100-1000-fold higher than the ancestor, were comparable to the CIs of the evolved isolates from the previous study (Robinson et al., *PLoS Biol.* 16:e2006893, 2018). While the rate of adaptation observed in this study was relatively fast, it was slower than was previously observed for mutator Aer01 (adaptation in all lines by passage 4), as expected, because of differences in mutation rate. To assay for a general growth advantage of these isolates their growth in rich media was compared to the ancestor and no overt differences were observed (FIG. 5).

In order to investigate the mutations accumulated by the evolved isolates during passaging, with the goal of identifying adaptive mutations, the genomes of all of the isolates represented in FIG. 4 were sequenced (Lines 1-5; passages 5, 10, 15, and 20). By comparing the evolved genomes to the ancestral genome, a small set of mutations was identified within the isolates (Table 3). Only isolates predicted to have adapted, as indicated by increased CI (FIG. 4), had mutations. Of the adapted isolates, the majority accumulated only one or two mutations, and the isolates with the most (five) were in line 5. Surprisingly, of this small collection of mutations, all replicate lines carried mutations in the same gene, named herein spdE. Across all lines there were 7 different spdE mutations identified, and none of the lines shared the same specific spdE mutation. Furthermore, over half of the mutations were clear loss-of-function mutations; two were nonsense, two were frame-shift, and three were missense mutations. It is worth nothing that the genome resequencing analysis software (breseq;) also predicted potential genomic rearrangements in a subset of isolates (6/17); however, since there was no obvious indications of the adaptive potential of these mutations as would be indicated by rearrangements in similar genomic loci across lines, they were not pursued.

It could be hypothesized that selective pressures for host colonization within a host-microbe system are influenced by host genotype. However, previous results showed that early-evolved isolates had the same competitive fitness in the host genotype they were evolved in (WT) and a different genotype (myd88$^{-/-}$); host genotype-specific completive fitness was only observed in further-evolved isolates. Therefore, Aer01 was evolved in two different host genotypes (WT and myd88$^{-/-}$ immunodeficient) with the expectation that selection of mutations in the same genes or pathways for populations evolved in both host genotypes would be observed. The results here support that the initial adaption confers an advantage for host colonization independent of host genotype, and therefore is likely not specific to the intra-host environment.

TABLE 3

Mutations identified in evolved *Aeromonas* isolates

| Evolved in wild-type fish | | | | | | | | | | | | Evolved in myd88$^{-/-}$ fish | | | | | | | |
|---|---|---|---|---|---|---|---|---|---|---|---|---|---|---|---|---|---|---|---|
| Line 1 | | | | Line 2 | | | | Line 3 | | | | Line 4 | | | Line 5 | | | | |
| 5 | 10 | 15 | 20 | 5 | 10 | 15 | 20 | 5 | 10 | 15 | 20 | 5 | 10 | 15 | 5 | 10 | 15 | 20 | mutation | gene |
| X | | | | | | | | | | | | | | | | | | | C→T (Q362*) | spdE |
| | | | | | X | X | | | | | | | | | | | | | G→A (A363T) | spdE |
| | | | | | | | | X | | | | | | | | | | | C→G (T321S) | spdE |

TABLE 3-continued

Mutations identified in evolved *Aeromonas* isolates

| Evolved in wild-type fish | | | | | | | | | | | | Evolved in myd88⁻/⁻ fish | | | | | | | | |
|---|---|---|---|---|---|---|---|---|---|---|---|---|---|---|---|---|---|---|---|---|
| Line 1 | | | | Line 2 | | | | Line 3 | | | | Line 4 | | | Line 5 | | | | | |
| 5 | 10 | 15 | 20 | 5 | 10 | 15 | 20 | 5 | 10 | 15 | 20 | 5 | 10 | 15 | 5 | 10 | 15 | 20 | mutation | gene |
| | | | | | X | | | | | | | | | | | | | | Δ1 bp (755/1635 nt) | spdE |
| | | | | | | | | X | X | X | X | | | | | | | | Δ1 bp (485/1635 nt) | spdE |
| | | | | | | | | | | | | X | X | | | | | | G→A (W127*) | spdE |
| | | | | | | | | | | | | | | | X | X | X | | C→A (A298D) | spdE |
| | X | | | | | | | | | | | | | | | | | | C→T (R22Q) | pepE ← |
| | | | | | | X | X | | | | | | | | | | | | C→T (A71T) | 00459 ← |
| | | | | | | X | X | | | | | | | | | | | | T→C (I247M) | prsE ← |
| | | | | | | X | X | | | | | | | | | | | | +1 bp (1015/1674 nt) | outD → |
| | | | | | | | | | | | | | | | X | X | X | X | C→T (intergenic) | 01342 ←/→ 01343 |
| | | | | | | | | | | | | | | | | X | X | X | A→T (A88A) | stpA_1 |
| | | | | | | | | | | | | | | | | X | | | G→T (intergenic) | glsA2 ←/← 02546 |
| | | | | | | | | | | | | | | | X | X | X | X | A→C (I86L) | kinB→ |

Example 3

Figure 6A:
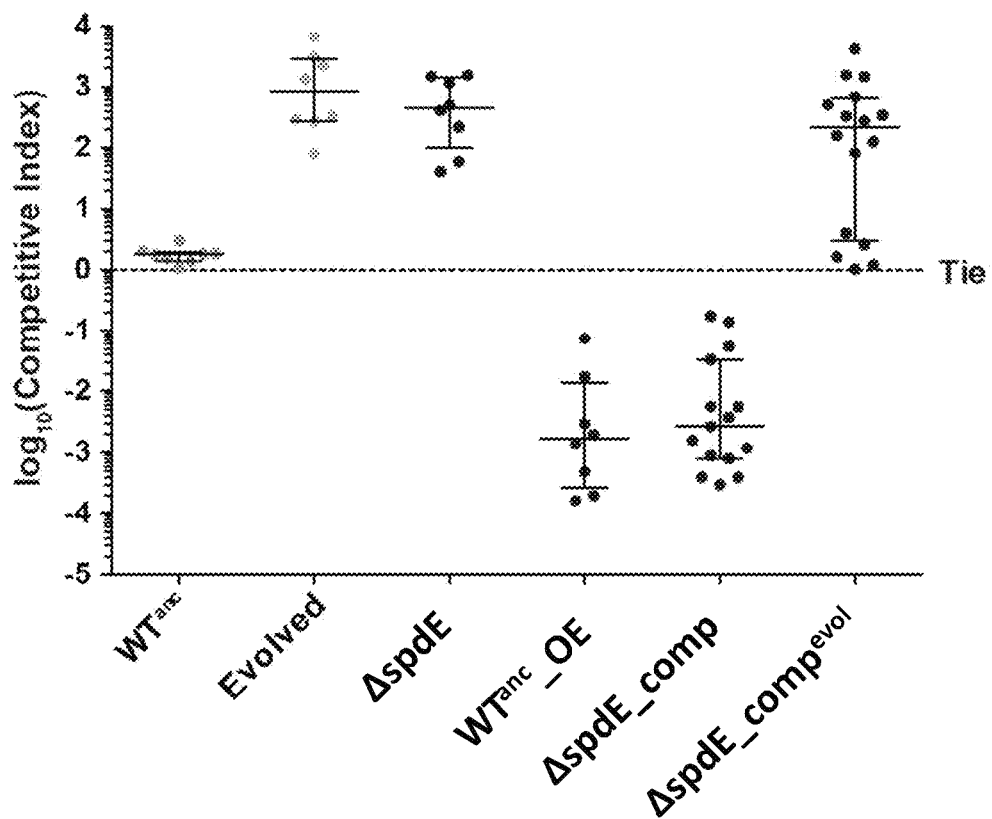
FIGS. 6A-6D show mutation of spdE is adaptive, enabling rapid immigration into the host and fish-to-fish transmission.

Mutation of spdE Enables Immigration into Host and Fish-to-Fish Transmission The finding that all evolved lines accumulated mutations in the same gene, spdE, most of which were loss-of-function, strongly suggested that those mutations are adaptive. To confirm this, spdE was deleted in the ancestral genome and its phenotype was assessed. The competitive index for ΔspdE was determined as described above, and it was compared to an evolved isolate which contains a loss-of-function mutation (1 bp deletion) in spdE. Deletion of spdE resulted in an average CI that recapitulated what was measured for the evolved isolate (FIG. 6A). Since deletion of spdE increases CI, a reduction in CI upon increased expression of spdE was predicted. Indeed, when spdE was over-expressed in the ancestor, a dramatic decrease in the average CI occurred (FIG. 6A; $WT_{anc\_OE}$). ΔspdE was complemented with both a WT copy of spdE, and the evolved allele (1 bp deletion), which complemented and did not complement, respectively (FIG. 6A; ΔspdE_comp, ΔspdE_comp, ΔspdE_comp$^{evol}$).

Figure 2:
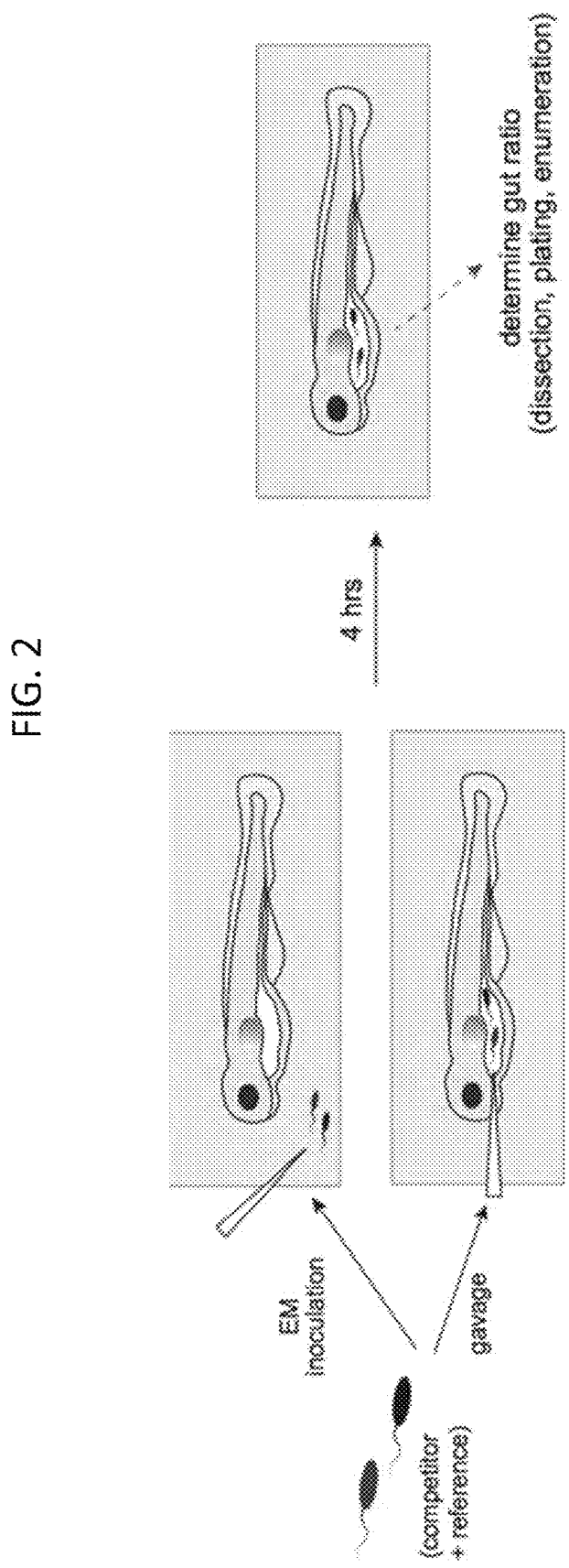
FIG. 2 is a schematic diagram of a gavage experiment.
Figure 6B:
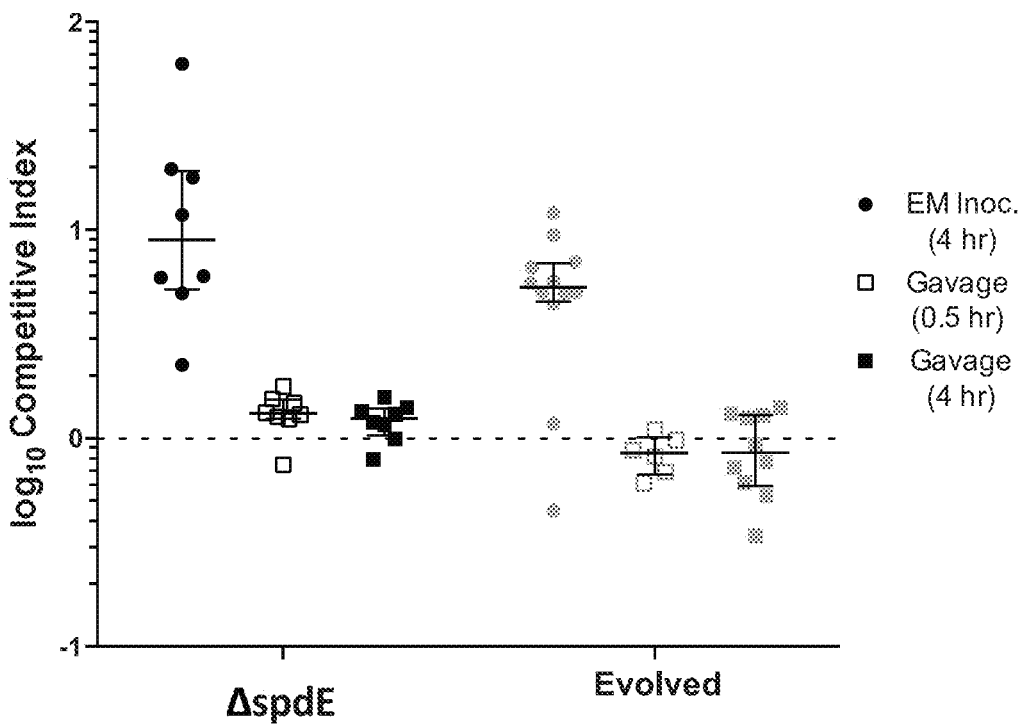
Figure 7:
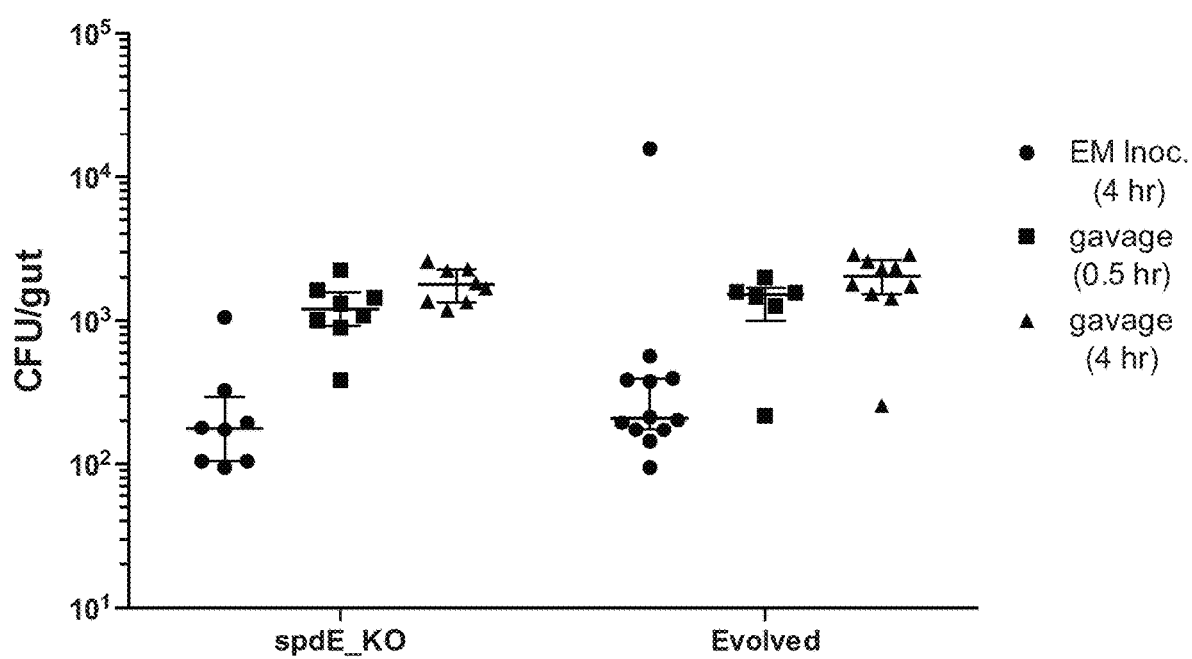
FIG. 7 is a graph showing CFU/gut for gavage experiment.

The competitive advantage seen in the evolved and ΔspdE strains was tested to determine if it was dependent on the mode of inoculation. If the colonization advantage is due to the ability to immigrate into the fish more quickly, then the relative competitive difference between the WT and competing stains would be expected to be reduced when the strains are administered directly to the host intestine, effectively bypassing the immigration step of colonization. Competitions were performed by inoculating the fish either via the standard route (adding the to the flask medium; EM), or microgavaging the competition mixtures directly into the fish intestine (FIG. 2). Fish were dissected and gut ratios of the strains were determined for the gavaged fish right after inoculation (~0.5 hrs), and for both conditions at 4 hrs post-inoculation. For both time points, CIs were calculated using the strain ratio in the starting inoculum. Both the ΔspdE and evolved isolates had significantly higher CIs when the fish were inoculated via the EM compared to when they were gavaged (FIG. 6B). Importantly, the fish were gavaged at an initial intestinal abundance (~$10^3$) well below the average carrying capacity of Aer01 (~$10^4$), and during the 4 hr competition they experienced some growth (FIG. 7).

Figure 6C:
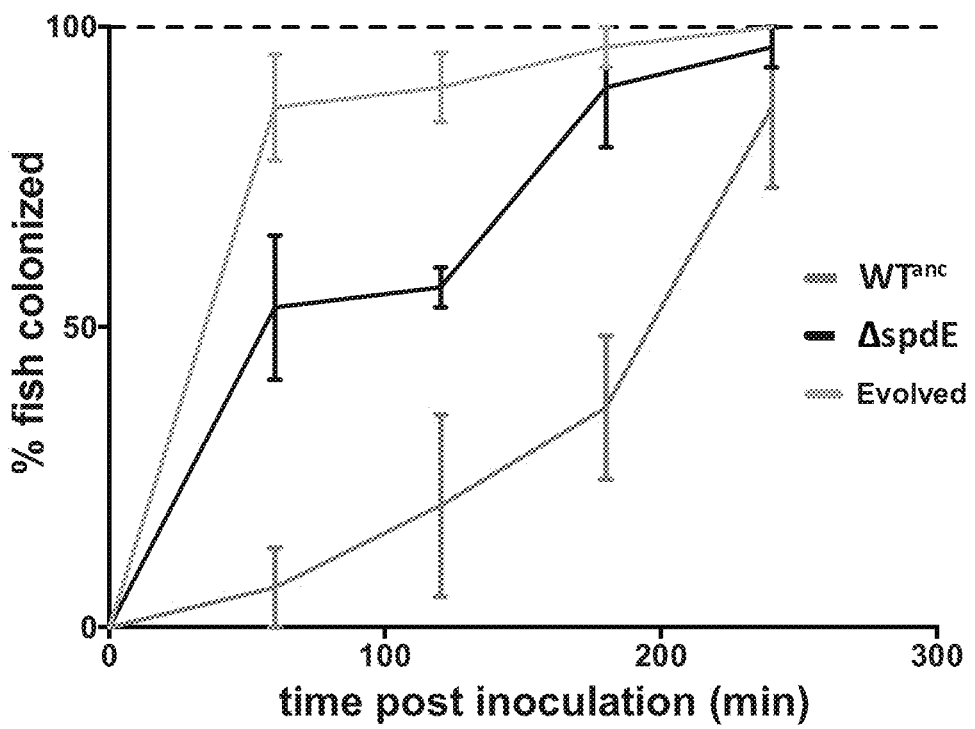
Figure 6D:
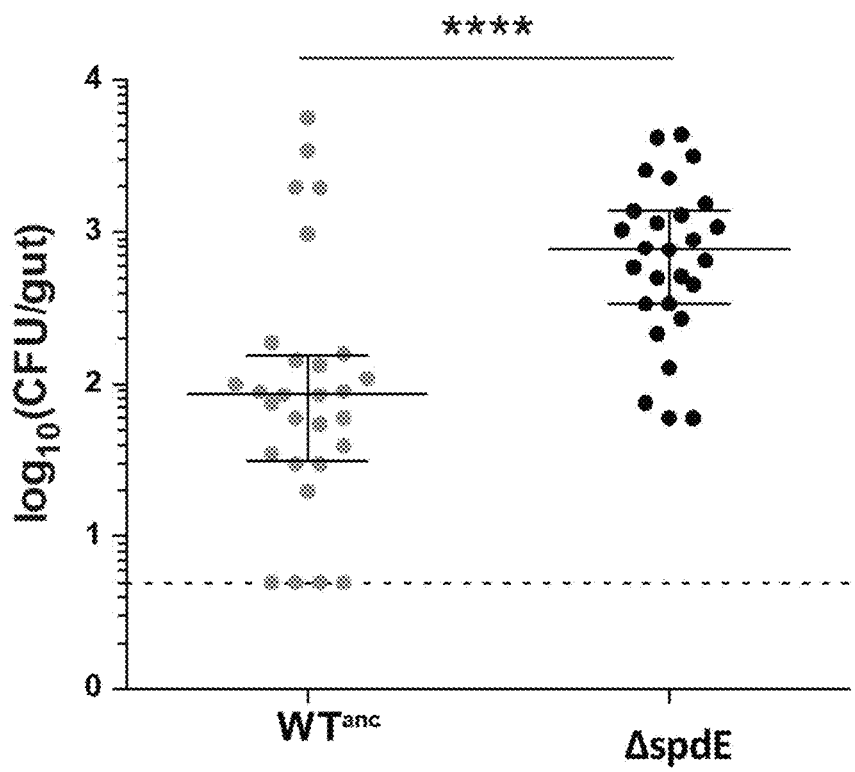

To more directly investigate differences in immigration rate, migration rate experiments were performed. Fish were mono-associated (inoculated with individual strains) via the EM, then 10 fish were dissected every 60 minutes, and the fraction of fish colonized at each time point was calculated (FIG. 3). Compared to the ancestor ($WT^{anc}$), both the evolved isolate and ΔspdE immigrated into fish more quickly (FIG. 6C). This experiment assessed the ability of Aer01 variants to migrate into GF fish from the environment during initial colonization. Next, whether spdE impacts Aer01 migration from one fish to another starting from a colonized fish was tested. To do this, fish mono-associated with individual strains for 24 hrs (donor fish; 2) were added to flasks of GF fish (recipient fish; 10-15). After allowing 15 hrs for Aer01 to migrate from donor to recipient fish, the fish were dissected and determined the abundance of Aer01 in all fish within each flask (FIG. 6D). Interestingly, the average Aer01 abundance in fish was higher for ΔspdE than for WT, demonstrating that mutation of spdE confers the ability to migrate into fish more quickly both from the aqueous environment, and also from other fish.

Example 4

SpdE Protein Architecture and Characterization of Ligand Binding

Figures 8A, 8B, 8C:
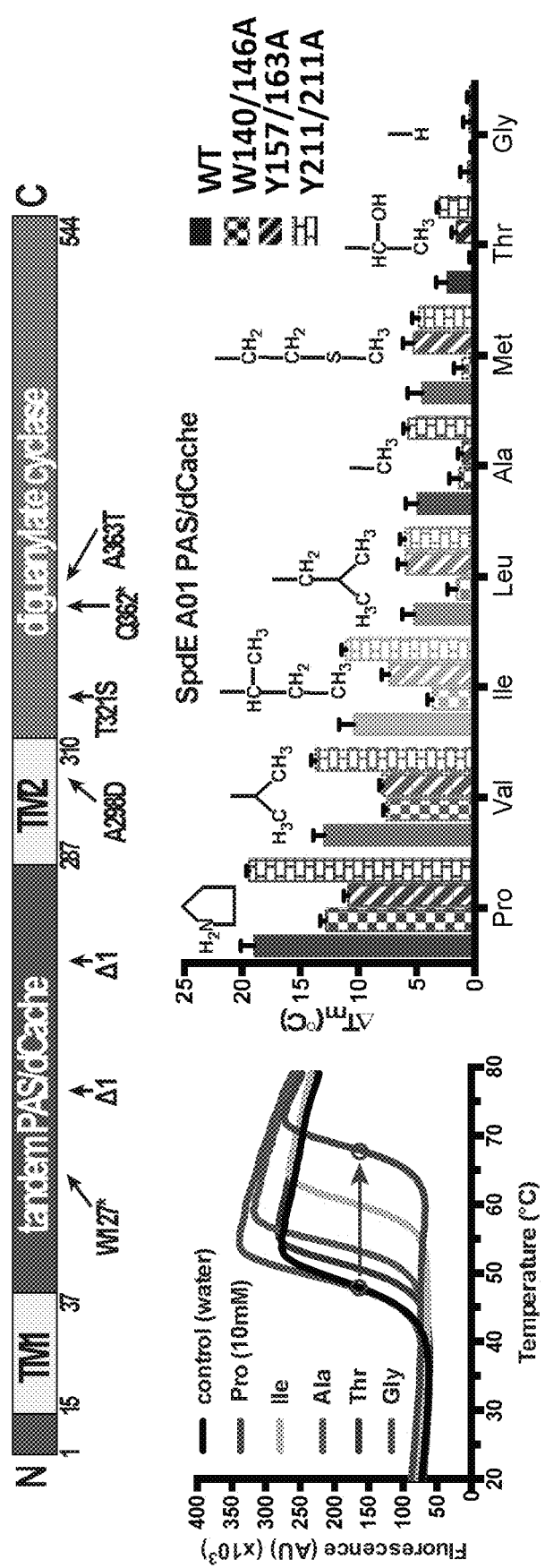
FIGS. 8A-8E show SpdE protein architecture and characterization of ligand binding.
Figure 8D:
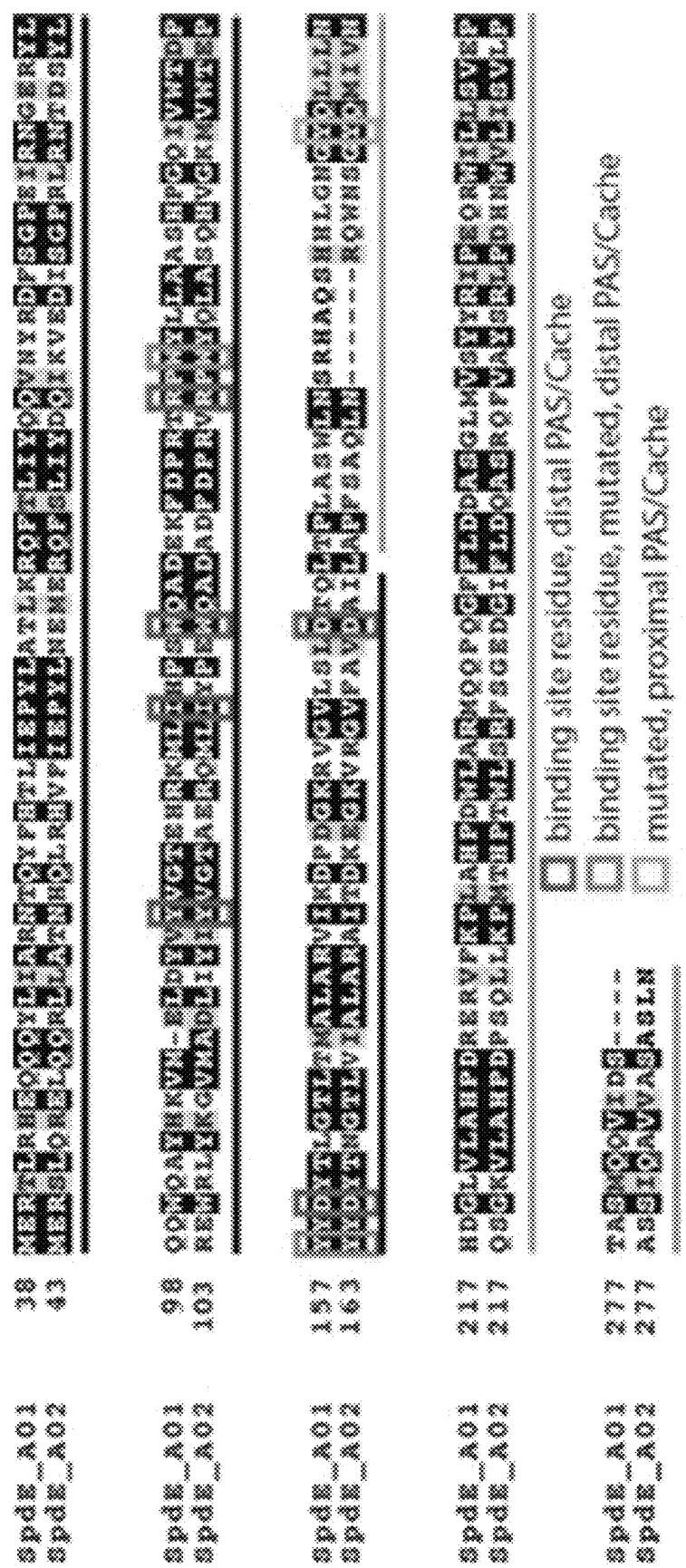

Sequence annotation of the spdE gene product revealed that it is a 544 amino acid transmembrane protein containing two functional domains—an N-terminal tandem PAS/dCache domain, and a C-terminal diguanylate cyclase domain (FIG. 8A). The mutations identified in the evolved genomes map to sites spread across the protein, suggesting that loss-of-function of either domain confers a selective advantage (FIG. 8A). Proteins with diguanylate cyclase activity are known to play a role in various aspects of bacterial physiology due to their ability to synthesize 3',5'-cyclic diguanylic acid (c-di-GMP), an intracellular signaling molecule unique to bacteria. PAS/Cache domains are small-molecule sensing domains, known to bind a variety of ligands, and regulate the activity of concomitant effector domains (Moglich et al., *Structure* 17:1282-1294, 2009). However, for the majority of PAS/Cache-containing proteins their specific ligands have not been identified and furthermore cannot be predicted by sequence. Proteins with similar protein architecture to SpdE have been identified, but few have been extensively characterized (Giacalone et al., *mBio* 9:e01254-18, 2018).

Figure 9:
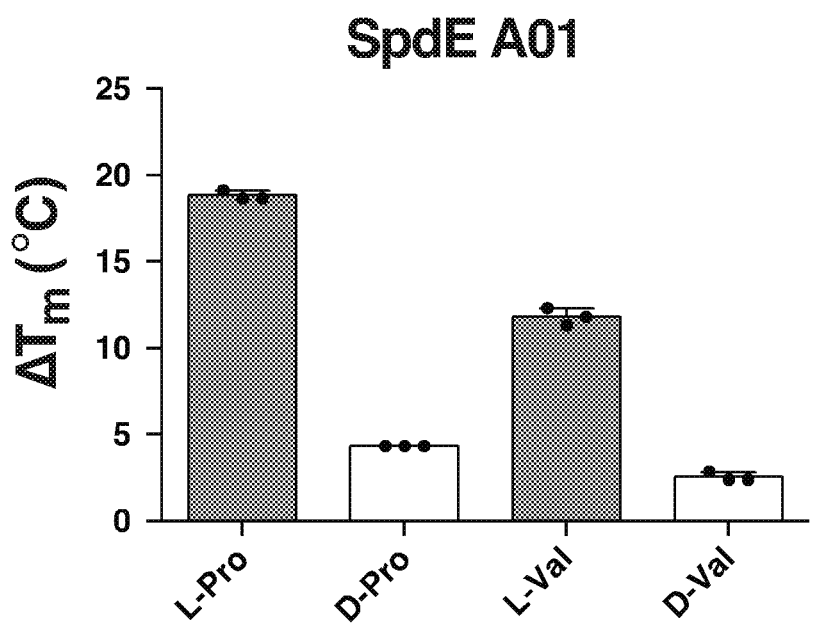
FIG. 9 is a graph of thermofluor data comprising L- and D-amino acid stabilization with SpdE A01.

In order to identify SpdE ligands, a thermal shift assay was conducted using 96-well Biolog Phenotype MicroArray plates as a high-throughput approach to screen compounds for ligand candidates. Using heterologously expressed and purified tandem PAS/dCache region of the protein (residues 37-287), ~200 compounds were screened for ones that conferred a significant shift in protein thermal stability (see Table 4). This resulted in identification of one polar and six hydrophobic amino acid ligand candidates. To confirm positive hits from the initial screen, the assay was repeated using known concentrations (10 mM) of pure amino acids. An example thermal shift plot is presented in FIG. 8B. For each curve, the melting temperature ($T_m$) was determined (brown circles), which corresponds to the midpoint of protein unfolding. The $\Delta T_m$ (difference between test $T_m$ and water control $T_m$) was calculated for each amino acid condition. The largest thermal shift was seen in the presence of proline, with an average temperature difference compared to the water control of ~20 degrees (FIG. 8B; arrow). Replicate $\Delta T_m$ data for each amino acid ligand showed that the amino acids that resulted in the largest shifts were proline, valine, and isoleucine, respectively, followed to a smaller degree by leucine, alanine, methionine, and threonine (FIG. 8C; solid bars). Glycine is included to show a negative amino acid control. Since D-isomers of some amino acids are known to be produced and sensed by bacteria, and thus could have biological relevance for SpdE, it was confirmed that SpdE binding was specific to the L-isomeric forms of these ligands (FIG. 9).

TABLE 4

Compounds included in Biolog plates (PM2A, PM3B)

| Well | PM2A | PM3B |
|---|---|---|
| A1 | Negative Control | Negative Control |
| A2 | Chondroitin Sulfate C | Ammonia |
| A3 | a-Cyclodextrin | Nitrite |
| A4 | b-Cyclodextrin | Nitrate |
| A5 | g-Cyclodextrin | Urea |
| A6 | Dextrin | Biuret |
| A7 | Gelatin | L-Alanine |
| A8 | Glycogen | L-Arginine |
| A9 | Inulin | L-Asparagine |
| A10 | Laminarin | L-Aspartic Acid |
| A11 | Mannan | L-Cystine |
| A12 | Pectin | L-Glutamic Acid |
| B1 | N-Acetyl-D- Galactosamine | L-Glutamine |
| B2 | N-Acetyl-Neuraminic Acid | Glycine |
| B3 | b-D-Allose | L-Histidine |
| B4 | Amygdalin | L-Isoleucine |
| B5 | D-Arabinose | L-Leucine |
| B6 | D-Arabitol | L-Lysine |
| B7 | L-Arabitol | L-Methionine |
| B8 | Arbutin | L-Phenylalanine |
| B9 | 2-Deoxy-D-Ribose | L-Proline |
| B10 | I-Erythritol | L-Serine |
| B11 | D-Fucose | L-Threonine |
| B12 | 3-0-b-D-Galactopyranosyl-D-Arabinose | L-Tryptophan |
| C1 | Gentiobiose | L-Tyrosine |
| C2 | L-Glucose | L-Valine |
| C3 | Lactitol | D-Alanine |
| C4 | D-Melezitose | D-Asparagine |
| C5 | Maltitol | D-Aspartic Acid |
| C6 | a-Methyl-D-Glucoside | D-Glutamic Acid |
| C7 | b-Methyl-D-Gactoside | D-Lysine |
| C8 | 3-Methyl-Glucose | D-Serine |
| C9 | b-Methyl-D-Glucuronic Acid | D-Valine |
| C10 | a-Methyl-D-Mannoside | L-Citruline |
| C11 | b-Methyl-D-Xyloside | L-Homoserine |
| C12 | Palatinose | L-Ornithine |
| D1 | D-Raffinose | N-Acetyl-L-Glutamic Acid |
| D2 | Salicin | N-Phenylethyl-amine |
| D3 | Sedoheptulosa | L-Pyroglutamic Acid |
| D4 | L-Sorbose | Hydroxylamine |
| D5 | Stachyose | Methylamine |
| D6 | D-Tagatose | N-Amylamine |
| D7 | Turanose | N-Butylamine |
| D8 | Xylitol | Ethylamine |
| D9 | N-Acetyl-D-Glucosaminatol | Ethanolamine |
| D10 | g-Amino Butyric Acid | Ethylenediamine |
| D11 | d-Amino Valeric Acid | Putrescine |
| D12 | Butyric Acid | Agmatine |
| E1 | Capric Acid | Histamine |
| E2 | Caproic Acid | β-Phynylehtyl-amine |
| E3 | Citraconic Acid | Tyramine |
| E4 | Citramalic Acid | Acetaminde |
| E5 | D-Glucosamine | Formamide |
| E6 | 2-Hydroxy Benzoic Acid | Glucuronamide |
| E7 | 4-Hydroxy Benzoic Acid | D,L-Lactamide |
| E8 | b-Hydroxy Butyric Acid | D-Glucosamine |
| E9 | g-Hydroxy Butyric Acid | D-Galactosamine |
| E10 | a-Keto Valeric Acid | Ethylenediamine |
| E11 | Itaconic Acid | Putrescine |
| E12 | 5-Keto-D-Gluconic Acid | Agmatine |
| F1 | D-Lactic Acid Methyl Ester | N-Acetyl-D-Mannosamine |
| F2 | Malonic Acid | Adenine |
| F3 | Melibionic Acid | Adenosine |
| F4 | Oxalic Acid | Cytidine |
| F5 | Oxalomalic Acid | Cytosine |
| F6 | Quinic Acid | Guanine |
| F7 | D-Ribono-1,4-Lactone | Guaniosine |
| F8 | Sebacic Acid | Thymine |
| F9 | Sorbic Acid | Thymidine |
| F10 | Succinamic Acid | Uracil |
| F11 | D-Tartaric Acid | Uridine |
| F12 | L-Tartaric Acid | Inosine |
| G1 | Acetamide | Xanthine |
| G2 | L-Alaninamide | Xanthosine |
| G3 | N-Acetyl-L-Glutamic Acid | Uric Acid |
| G4 | L-Arginine | Alloxan |
| G5 | Glycine | Allantoin |
| G6 | L-Histidine | Parabanic Acid |
| G7 | L-Homoserine | D,L-α-Amino-N-Butyric Acid |
| G8 | Hydroxy-L-Proline | γ-Amino-N-Butyric Acid |
| G9 | L-Isoleucine | ε-Amino-N-Caproic Acid |
| G10 | L-Leucine | D,L-α-Amino-Caprylic Acid |
| G11 | L-Lysine | δ-Amino-N-Valeric Acid |
| G12 | L-Methionine | α-Amnio-N-Valeric Acid |
| H1 | L-Ornithine | Ala-Asp |
| H2 | Phenylalanine | Ala-Gin |
| H3 | L-Pyroglutamic Acid | Ala-Glu |
| H4 | L-Valine | Ala-Gly |
| H5 | D,L-Carnitine | Ala-His |
| H6 | Sec-Butylamine | Ala-Leu |
| H7 | D,L-Octopamine | Ala-Thr |
| H8 | Putrescine | Gly-Asn |
| H9 | Dihydroxy Acetone | Gly-Gln |
| H10 | 2,3-Butanediol | Gly-Glu |
| H11 | 2,3-Butanone | Gly-Met |
| H12 | 3-Hydroxy 2-Butanone | Met-Ala |

To further investigate ligand binding, I-TASSER (Zhang, *BMC Bioinformatics* 9:40, 2008) was used to predict the structure of SpdE's tandem PAS/dCache domain, and compare it to a protein with a known structure and high identity (52%), a *Vibrio cholerae* chemoreceptor. This analysis revealed potential key binding pocket residues. To confirm, protein variants with single amino acid residue changes in this region were generated, two in the distal PAS/Cache (W140/146A and Y157/163A) and one in the proximal PAS/Cache (Y211/211A). For the majority of proteins that contain tandem PAS/dCache domains, it has been observed that ligand binding occurs in the distal PAS/Cache domain. This also was the case for SpdE, as there was a reduction in ligand binding for both residue changes in the distal PAS/Cache, but not for the corresponding tyrosine residue in the proximal PAS/Cache (FIG. 8C; checked, striped, and bricked bars, respectively). Furthermore, the W140/146A mutation in the distal PAS/Cache reduced thermal shift more than the Y157/163A mutation, suggesting it is more important for stabile ligand binding.

Figure 8E:
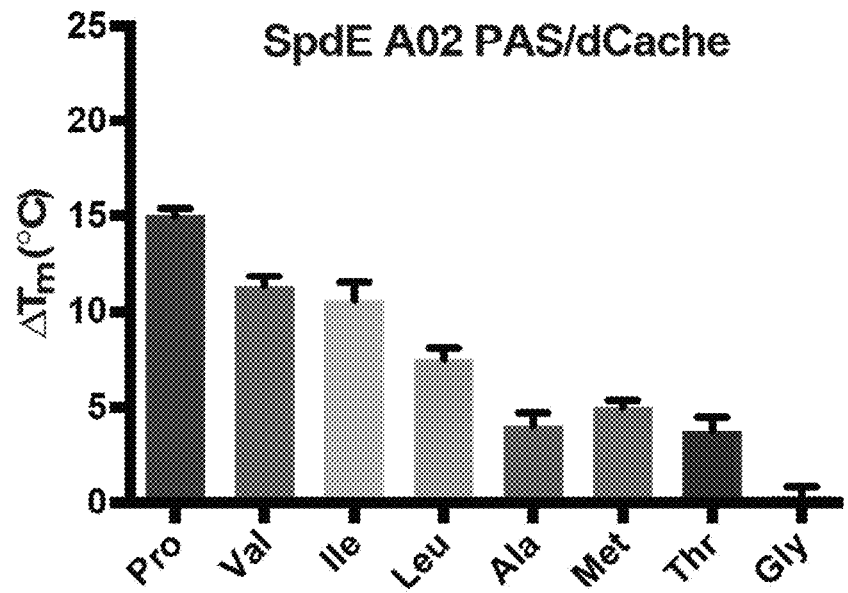
Figure 10:
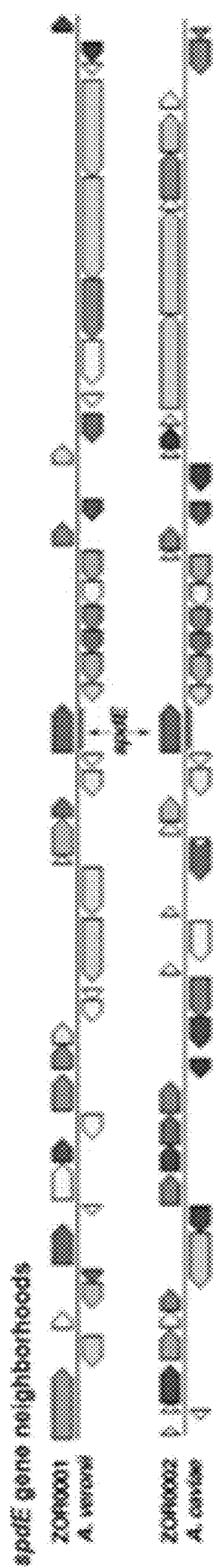
FIG. 10 is a schematic diagram of gene neighborhoods for A01 and A02 spdE showing genomic synteny.

Sequence conservation of spdE in a closely related *Aeromonas* species within a zebrafish gut isolate culture collection, *A. caviae* (isolate ZOR0002, hereafter referred to as Aer02) was examined. Comparison of the gene neighborhoods surrounding spdE within the genomes of these two *Aeromonas* species demonstrated a high level of gene synteny, supporting that they are homologs (FIG. 10). Alignment of amino acid sequences showed 53% identity across the SpdE tandem PAS/dCache region of the protein (FIG. 8D), and 53.4% identity across the entire protein. Importantly, the key binding residues identified and tested above were conserved in Aer02 SpdE (blue boxed residues), as were additional key binding residues identified and described below (pink boxes). Finally, to confirm the functional conservation of Aer02 SpdE ligand binding, the same thermal shift assay as in FIG. 3C was carried out and the same pattern in the $\Delta T_m$ data across the tested amino acid ligands was observed as for Aer01 SpdE (FIG. 8E).

Example 5

SpdE Tandem PAS/dCache Crystal Structure

Figure 11A:
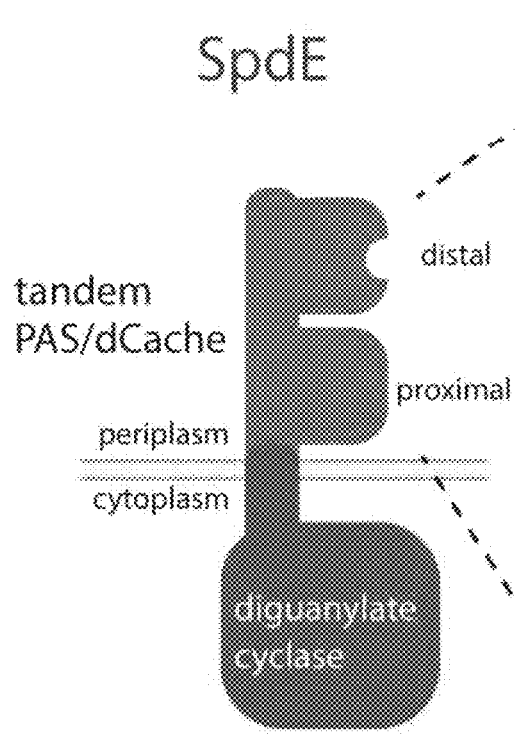
FIGS. 11A-11D show a schematic of SpdE protein domains relative to bacterial inner membrane (FIG. 11A) and the molecular structure of SpdE A02 with proline (pink) bound in distal PAS/Cache domain at 1.8 Å resolution (FIG. 11B). A model of SpdE A01 (teal) was produced using I-TASSER and overlaid with the SpdE A02 structure (gray) (FIG. 11C). Proline binding pocket with SpdE A02 residues are displayed in FIG. 11D. The residues are labeled with both the SpdE A01 and A02 numbering. The two residues underlined were mutated in SpdE A01 protein and shown to have decreased binding ability to ligands.
Figure 11B:
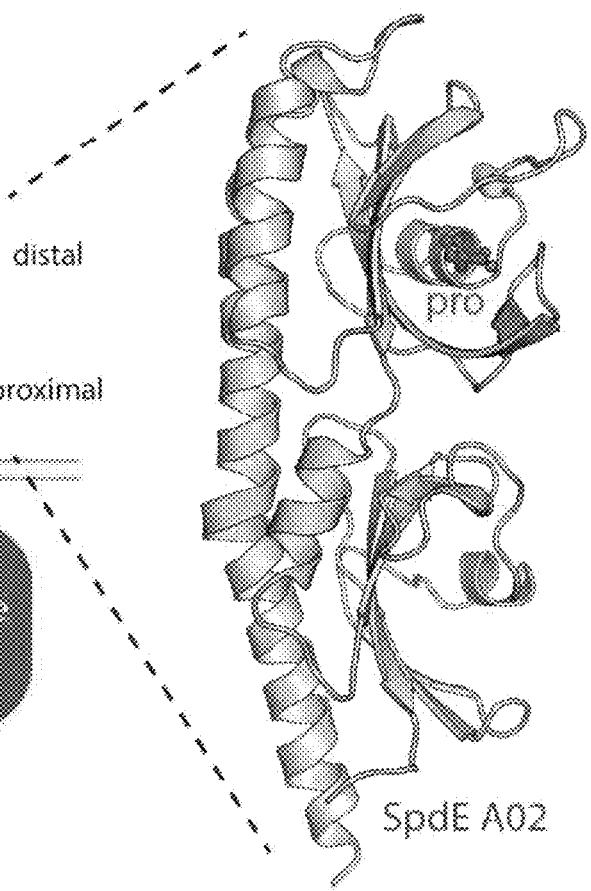
Figure 11C:
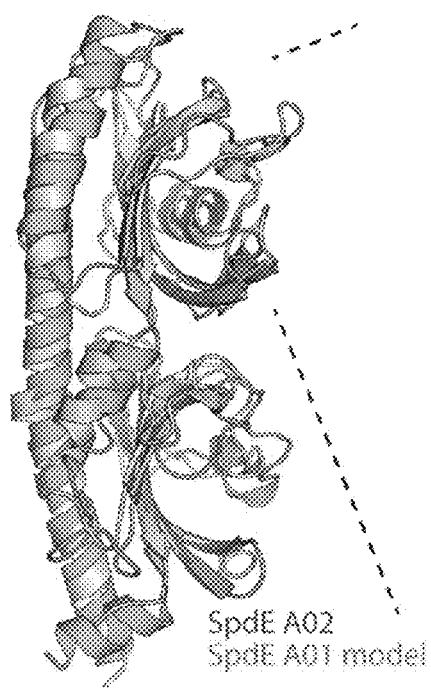
Figure 11D:
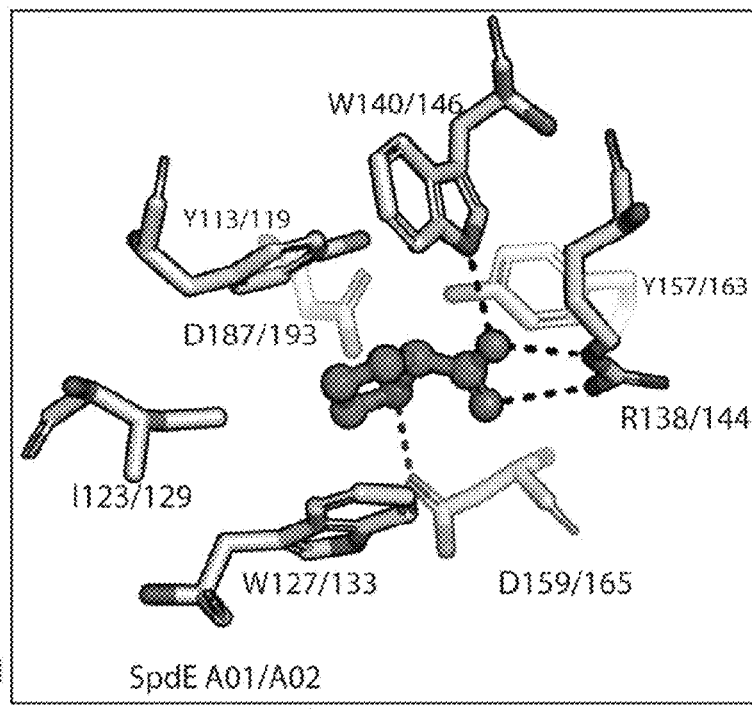

To further confirm ligand binding location and specific residues involved, both Aer01 and Aer02 SpdE PAS/Cache proteins were crystallized to determine the structures. However, only Aer02 SpdE crystals resulted in diffraction patterns of high enough quality to solve. Using Rosetta software to produce a molecular replacement search model, the structure of Aer02 SpdE was solved to 1.8 Å resolution (FIGS. 11A and 11B). A molecule of proline is bound where the previous biochemical analysis had predicted, in the distal PAS/Cache domain (FIG. 11B). Using the Aer02 structure and I-TASSER software, a model of the Aer01 SpdE periplasmic domain was obtained, which is predicted to fold very similarly to Aer02 SpdE (FIG. 11C, teal). Closer inspection of the binding site confirmed that several hydrogen bonds and a hydrophobic patch in the back of the pocket hold proline in place (FIG. 11D). The Aer01 SpdE binding site residues are 100% conserved with Aer02 SpdE and predicted to be in similar locations, providing additional evidence that proline is an Aer01 SpdE ligand and likely capable of regulating diguanylate cyclase activity.

Example 6

Figure 12A:
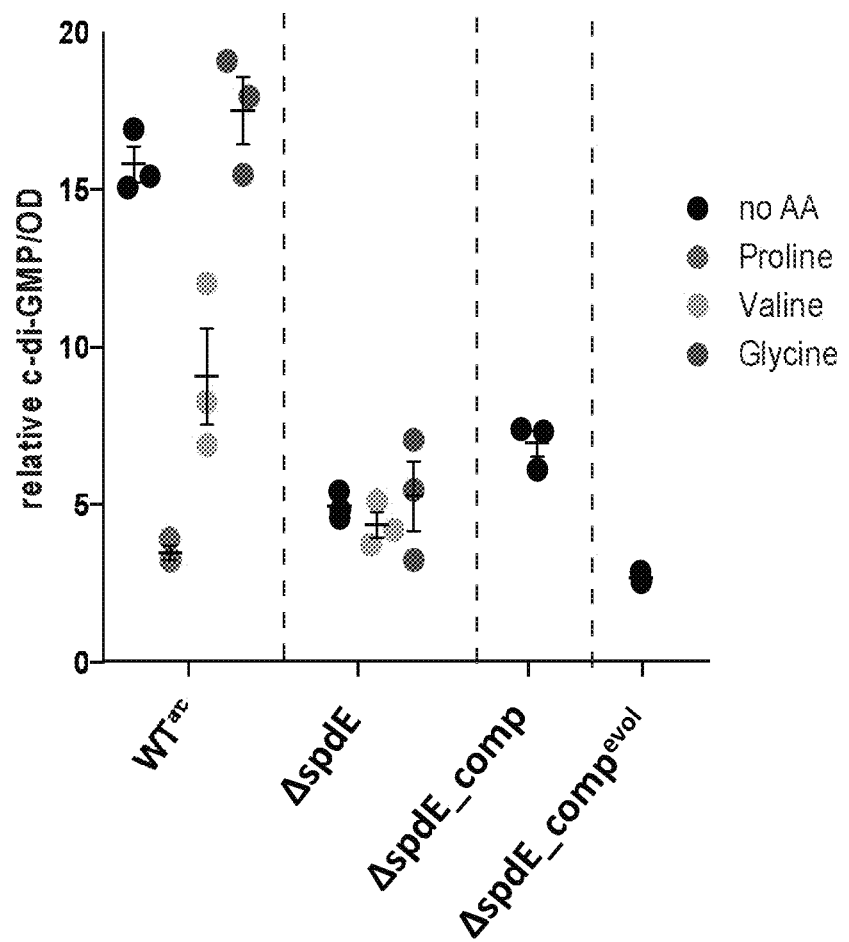

SpdE Regulates Motility and Biofilm Formation Via Modulation of Intracellular c-di-GMP PAS/Cache domains regulate the activity of their cognate functional domains such that ligand binding either activates or deactivates enzymatic activity. In the case of SpdE, ligand binding to the PAS/Cache was hypothesized to regulate SpdE diguanylate cyclase activity, thereby altering intracellular levels of c-di-GMP. To test this, WT and ΔspdE Aer01 were incubated in the presence or absence of amino acid ligands for ~4 hrs, then pelleted and lysed the cells to extract and quantify intracellular c-di-GMP. In the absence of ligand, WT Aer01 intracellular c-di-GMP levels were relatively high, but in the presence of ligand (here, proline and valine) c-di-GMP was significantly lower (FIG. 12A). As a control, no change was observed with the addition of the non-ligand amino acid, glycine. Interestingly, c-di-GMP was lower in the presence of proline compared to valine, which matched the trend in the thermal shift assay data (FIG. 8C). In comparison, c-di-GMP levels in ΔspdE were low, similar to the levels seen for the WT in the presence of proline, irrespective of the presence of ligand (FIG. 12A). Complementation of the ΔspdE with a wild-type copy of spdE rescued some of the c-di-GMP levels (p=0.015), while complementation with a loss-of-function (1 bp deletion) evolved allele did not rescue c-di-GMP (FIG. 12A). These data suggest that in the absence of ligand SpdE's diguanylate cyclase is enzymatically active, and that ligand binding decreases diguanylate cyclase activity.

Figure 12B:
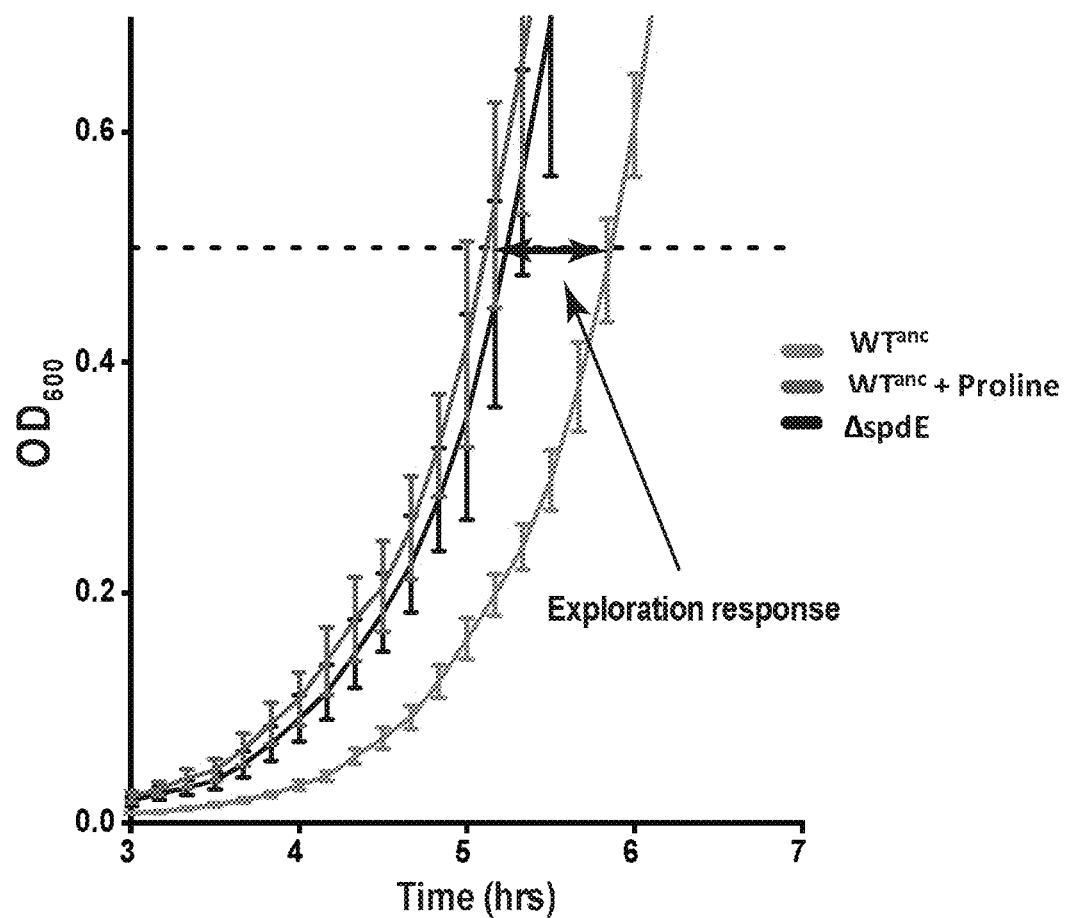
Figure 12C:
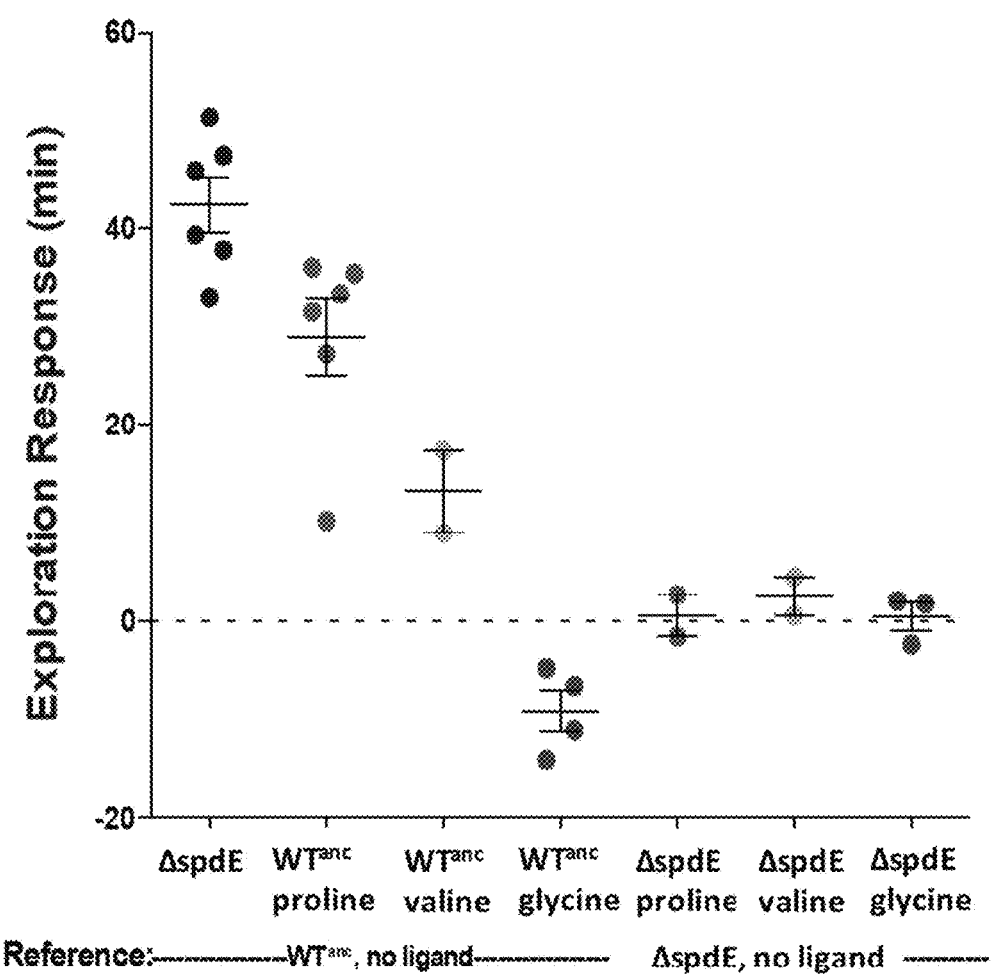
Figure 13:
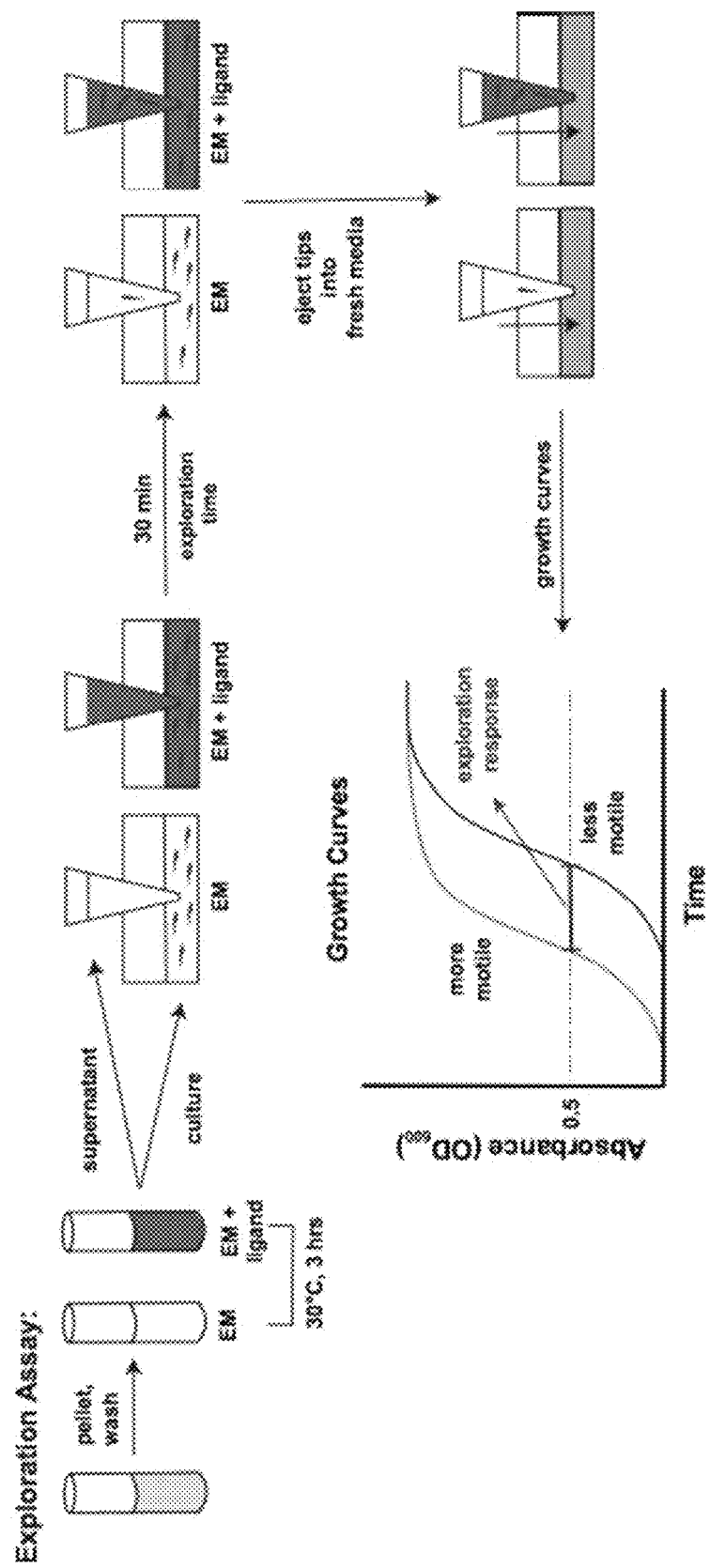
FIG. 13 is a schematic diagram showing the exploration assay.
Figure 14A:
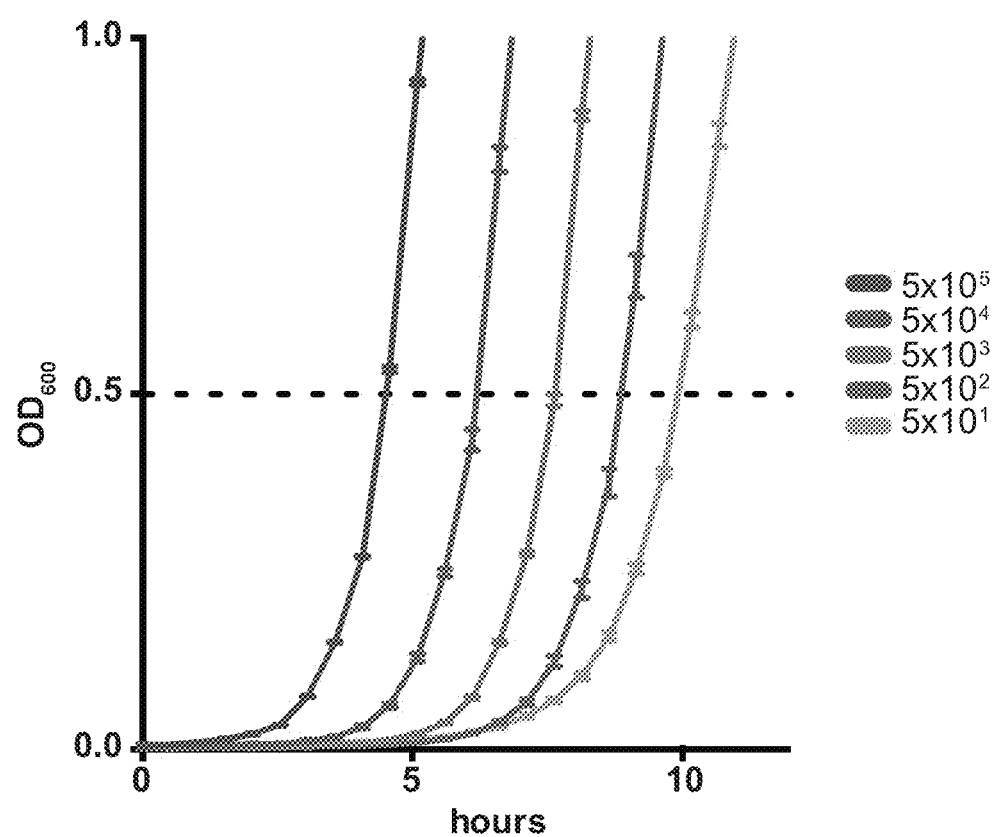
FIGS. 14A and 14B show exploration assay controls.
Figure 14B:
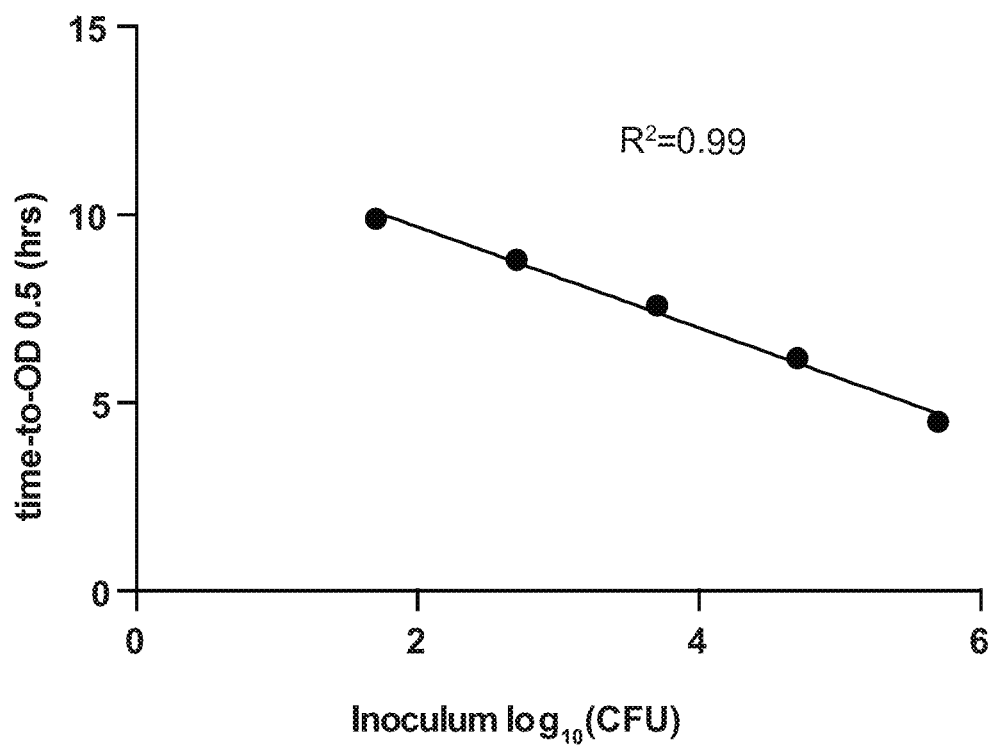
Figure 15:
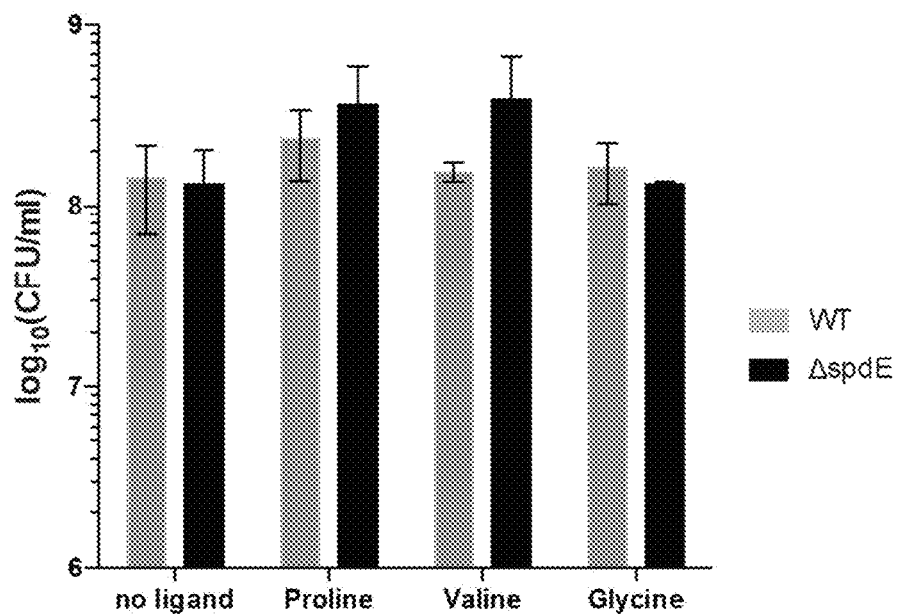
FIG. 15 is a graph of CDU data for exploration assay.
Figure 16:
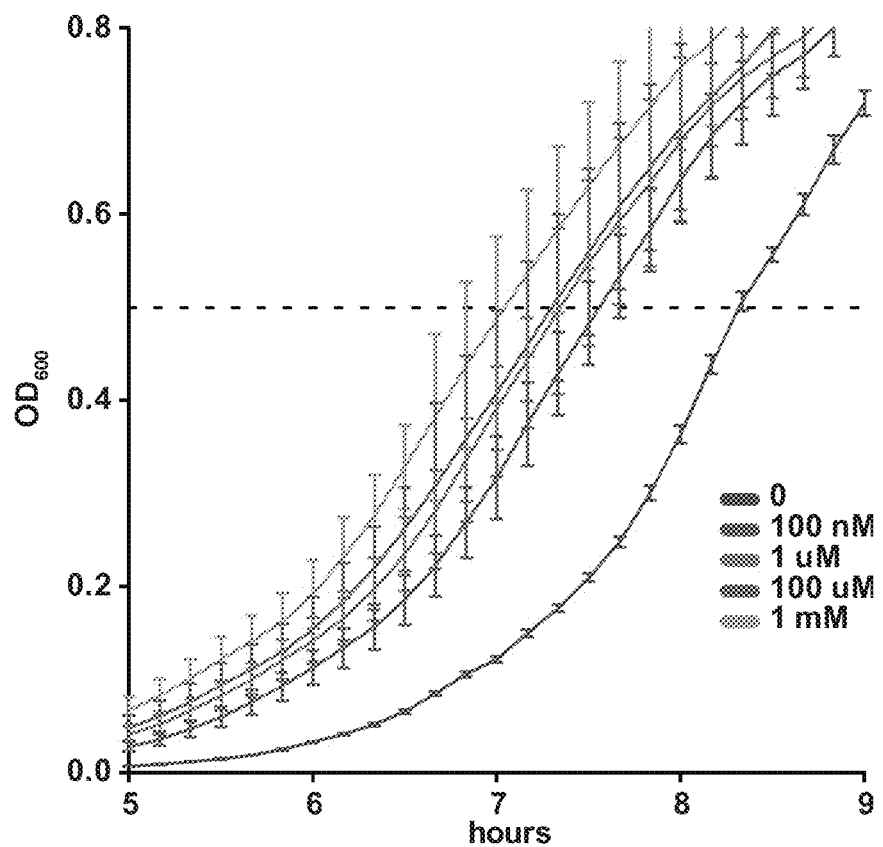
FIG. 16 is a graph of exploration assay data showing response across a range of proline concentrations.

To further characterize how SpdE impacts Aer01 motility, assays to measure motility at both the whole population and cellular levels were carried out. An "exploration assay" was used to measure population-level motility. For this assay Aer01 was incubated in the presence/absence of amino acid ligand (1 mM) for ~4 hrs, then the culture was added to the wells of a 96-well plate and pipette tips filled with the cell-free supernatant of the same cultures was lowered into the wells (FIG. 13). During a 30 min incubation period the Aer01 cells in the wells swam up into the pipette tips. This movement was designated "exploration," as there are no chemical gradients between the wells and tips and so it is not dependent on chemotaxis but rather a general capacity for motility; this could be envisaged as motility-facilitated cellular diffusion. To quantify the number of cells in the pipette tips after the 30 min exploration time, the contents of the pipette tips were ejected into the wells of a 96-well plate containing rich media and growth curves were monitored. The more cells in the tips, the higher the inoculum for the growth curve, and the earlier the growth curve will cross an arbitrary OD, here, 0.5 (FIG. 13). Time-to-OD 0.5 correlated with starting inoculum concentration, as determined by measuring growth curves across a 5-log dilution series of the inoculum (FIGS. 14A and 14B, $R^2$=0.99). This exploration assay was then conducted to measure motility of the WT and ΔspdE in response to SpdE ligands. Example exploration assay growth curves are presented in FIG. 12B. Compared to WT Aer01 in the absence of ligand, addition of proline increased motility resulting in the growth curve reaching OD 0.5 earlier, comparable to ΔspdE (FIG. 12B). This time difference between conditions, "exploration response," was calculated to compare across many strains and conditions (FIG. 12C). Exploration responses greater than 0 mean the Aer01 strain was more motile in that condition compared to the reference strain/condition. Upon addition of ligand, WT demonstrated increased motility and showed a stronger response to proline (mean=28.9 min) compared to valine (mean=13.2 min), consistent with the thermofluor data and intracellular c-di-GMP quantification. In contrast, ΔspdE did not have a motility response to ligand (FIG. 12C; right-most three groups) and was faster than WT regardless of the presence of ligand (FIG. 12C; far left group, mean=42.4 min). Importantly, these results are not explained by differences in CFU in the cultures (FIG. 15). Additionally, Aer01's motility is very sensitive to ligand, as a response was measured with addition of just 100 nM proline (10,000× lower), and that there is a dose-dependent response trend across concentrations between 100 nM and 1 mM proline (FIG. 16).

Figure 12D:
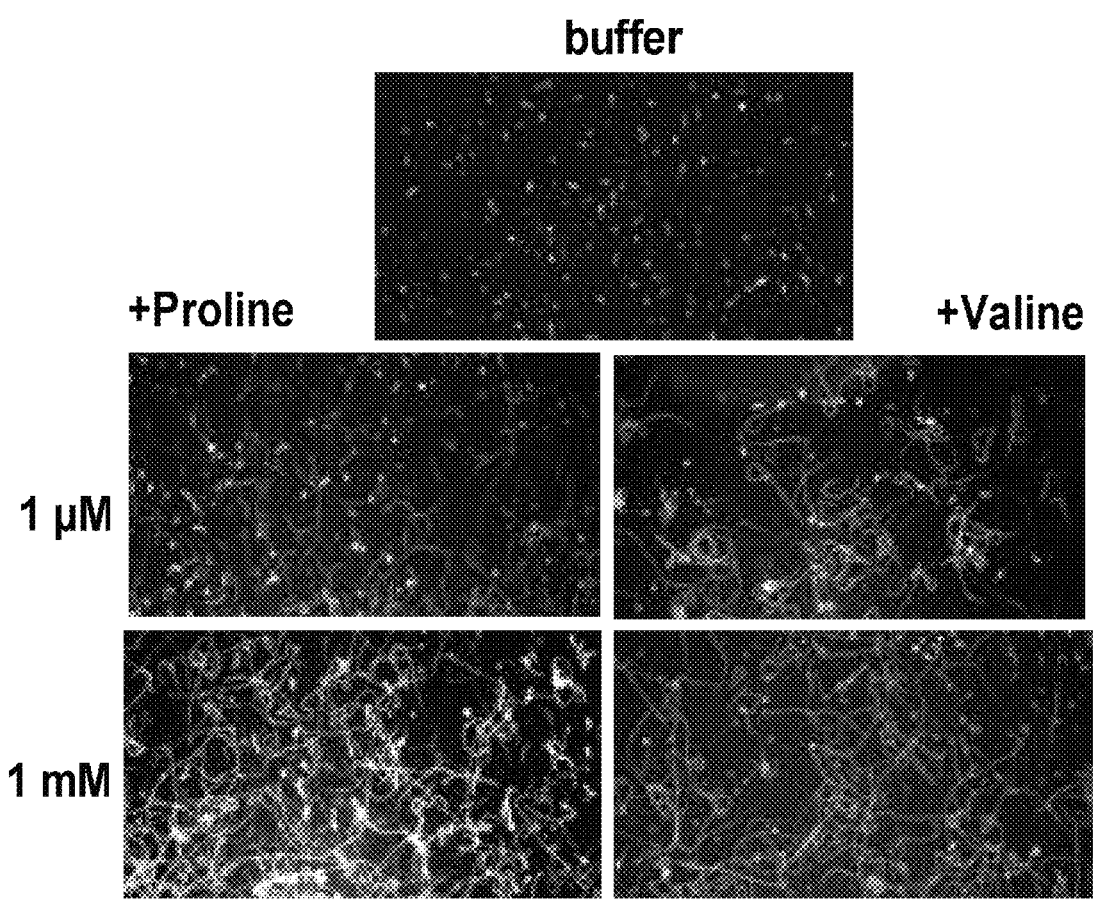
Figure 17A:
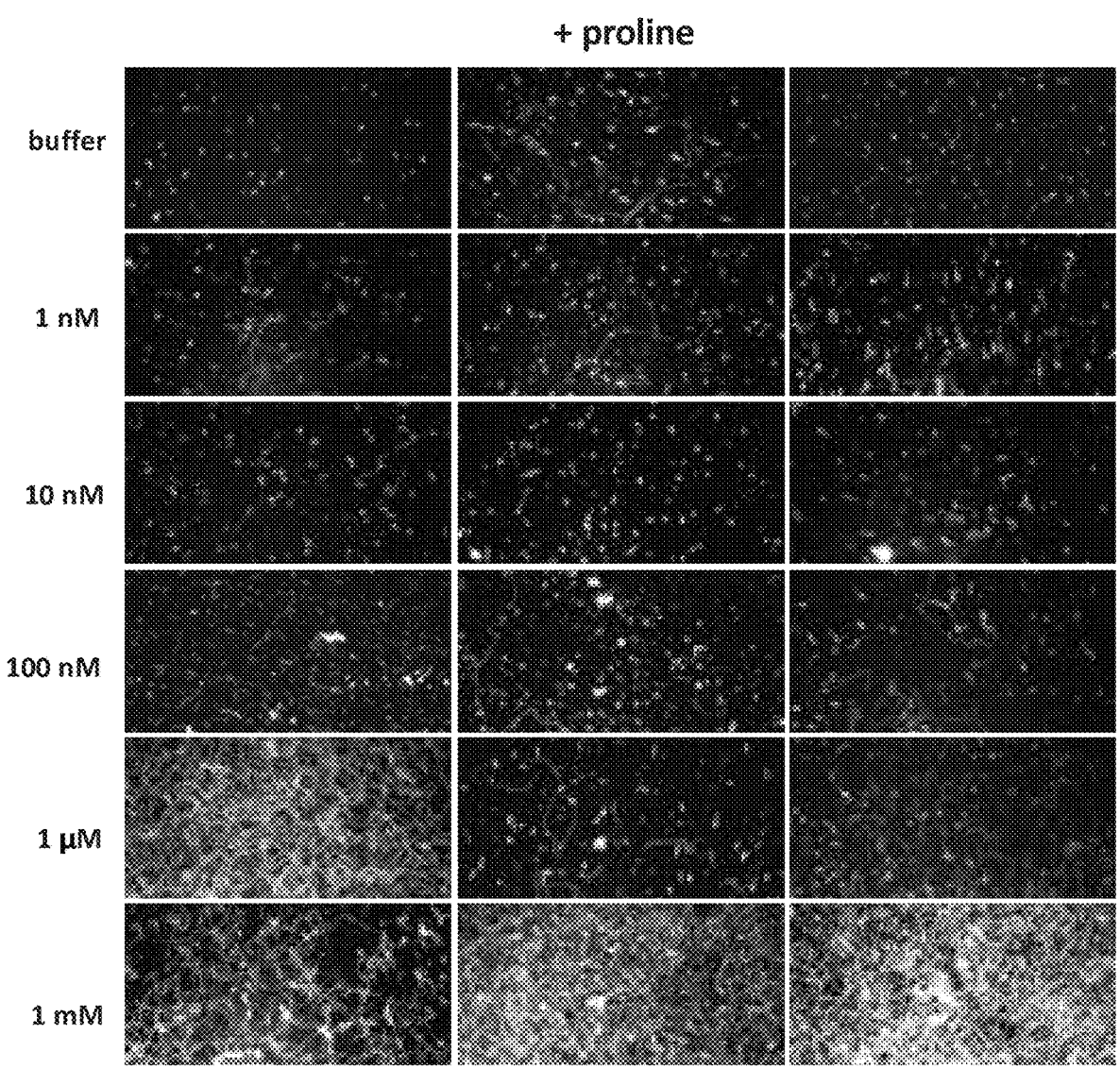
FIGS. 17A and 17B show all mass projections from tracking using proline (FIG. 17A) or valine (FIG. 17B).
Figure 17B:
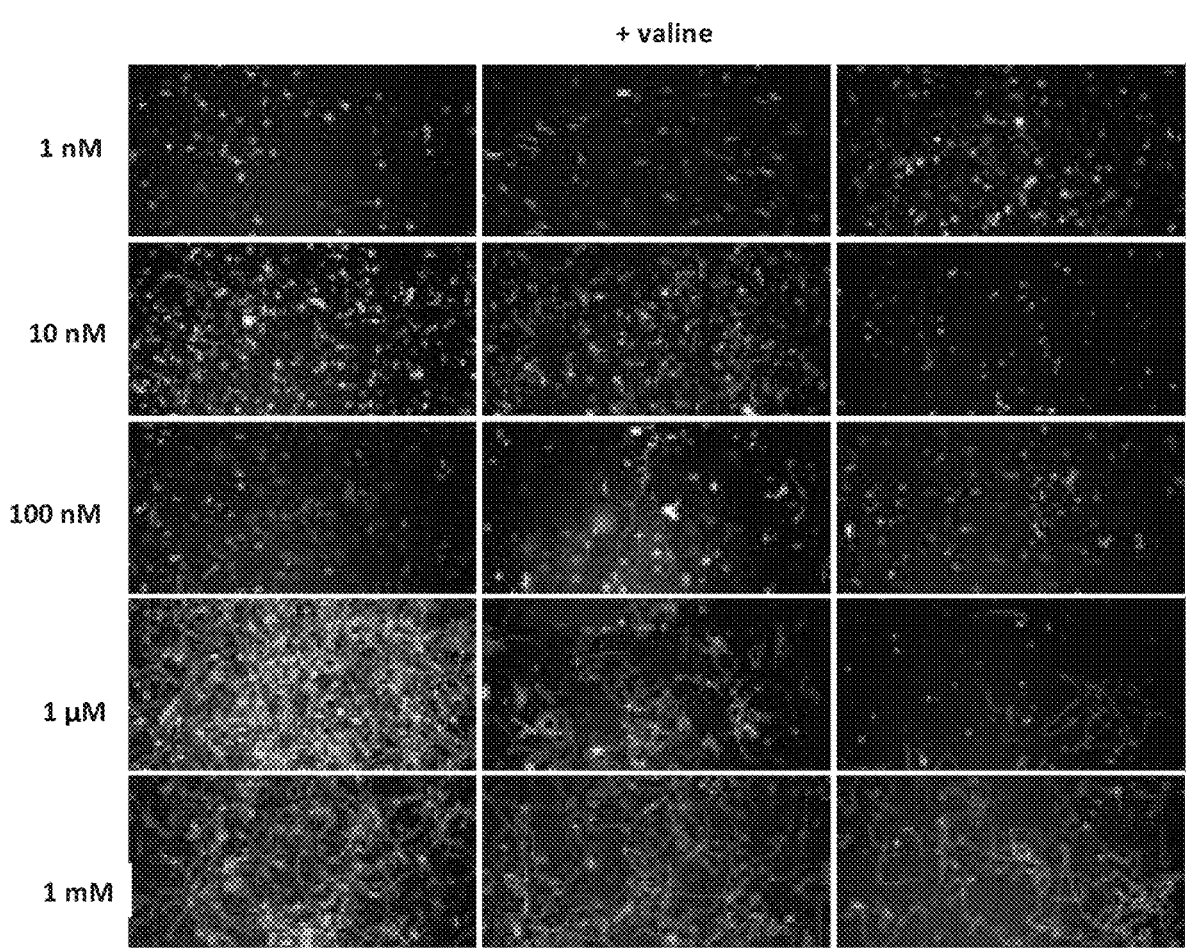

To get a visual confirmation of the impact of SpdE ligands on Aer01 motility, WT motility across a range of ligand concentrations was observed using microscopy. To do this, Aer01 was incubated in medium±ligand (ranging between 0 and 1 mM) then wet-mounted and imaged on an inverted microscope. Mass projection of the video recordings shows motility of individual cells as white tracks (representative plots, FIG. 12D; all plots, FIGS. 17A and 17B). In the absence of ligand (buffer) cells were primarily non-motile, with many clumped in small aggregates. Under these conditions little increase in motility was observed below 1 µM ligand; however, at 1 µM and 1 mM ligand (both proline and valine), there was a striking increase in the number of motile cells within the populations, with the largest motile response for 1 mM proline (FIG. 12E).

Figure 12F:
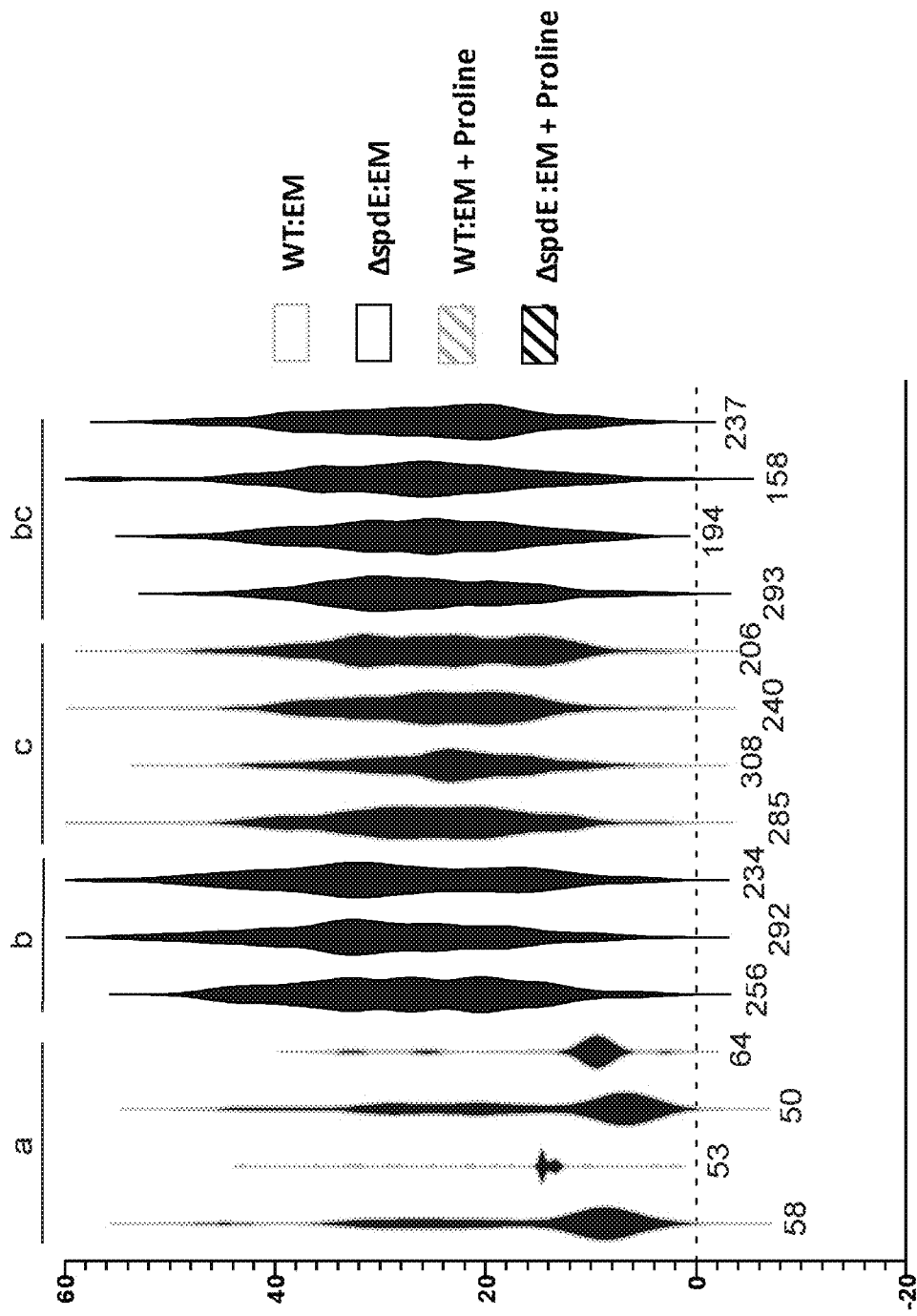

The video imaging allowed direct visualization of the motile response of WT Aer01 across a range of SpdE ligands; however, these conditions were not ideal for measuring individual cellular velocities since the imaged plane of the slide mounts was close to the glass surface to which cells could stick and not freely swim. Therefore, the cells were next imaged in a cuvette on a light sheet microscope where they would be recorded within a three-dimensional space and not impeded by surfaces. Both the WT and ΔspdE were imaged in medium without ligand (EM) and in the presence of 1 mM proline. Custom tracking software was used to measure the velocity of motile cells within replicate movies for each strain/condition. The cellular velocities of all tracks are plotted in FIG. 12F, where the distribution of all tracks within each video can be seen as presented in the violin plots (numbers under the plots represent the number of tracks included in the analysis). In the absence of ligand, the average of the WT median values was 12.6 µm/sec, which doubles to 24.5 µm/sec in the presence of proline. The ΔspdE was faster than WT in the absence of ligand (mean=28.9 µm/sec, comparable to WT+proline), and did not increase with the addition of proline (FIG. 12F).

Figure 12G:
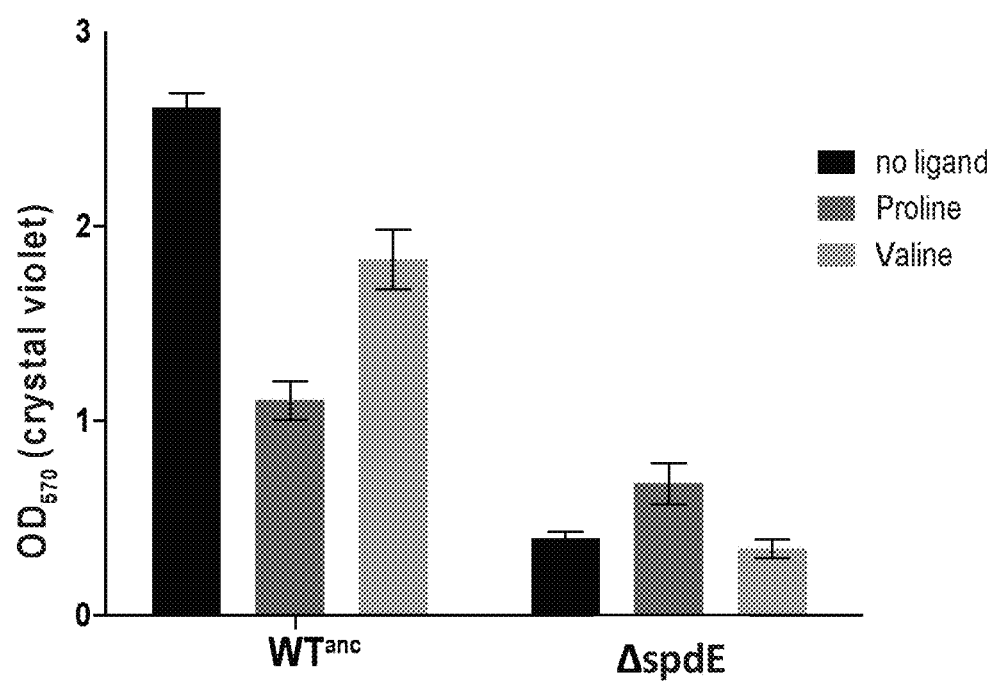

Increased bacterial motility generally correlates with a decrease in biofilm formation. Therefore, to assay if SpdE ligands also decrease Aer01's propensity to form biofilms, strains were incubated in 96-well plates in medium±ligand for 48 hrs, then a crystal violet assay was used to quantify biofilm formation. As expected, the WT formed more robust biofilms in the absence of ligand than when proline or valine were present (FIG. 12G). Again, there was a more dramatic response to proline than to valine, and ΔspdE had less biofilm than WT, regardless of the presence of ligand. Combined, these results show that SpdE functions to regulate Aer01 motility and concomitantly, biofilm formation.

Example 7

Aer01 Host Colonization is Modulated by SpdE

Figure 18A:
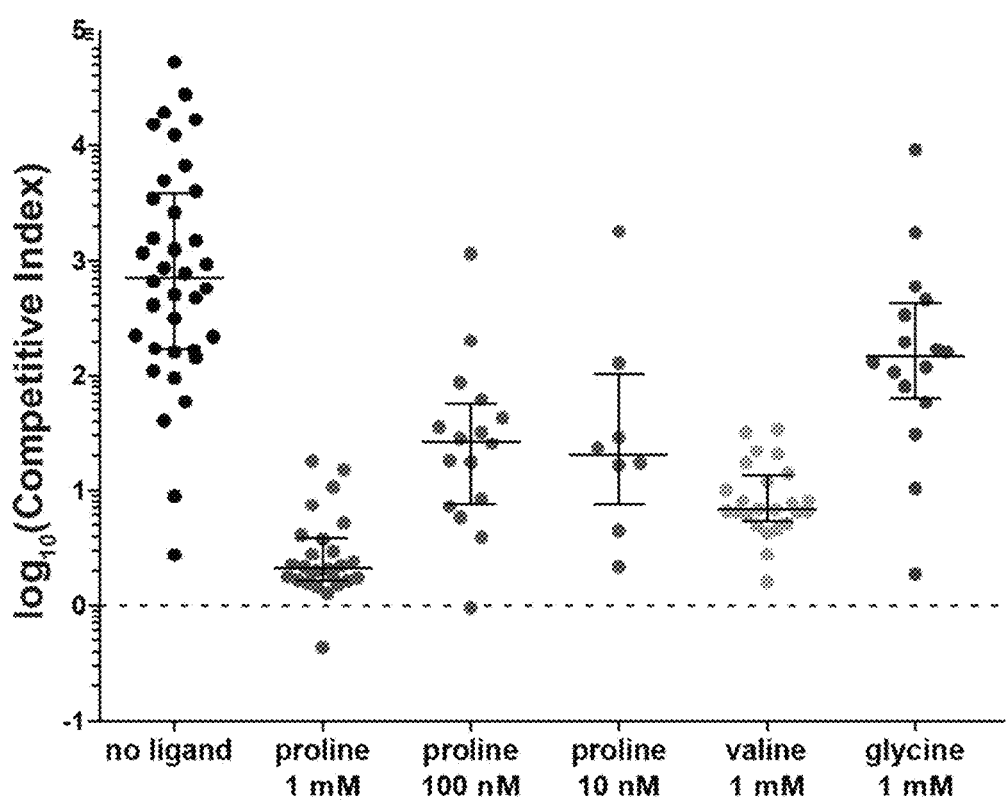
FIGS. 18A-18E illustrate that Aer01 host colonization is modulated by SpdE and mediated by the microbiota.
Figure 18B:
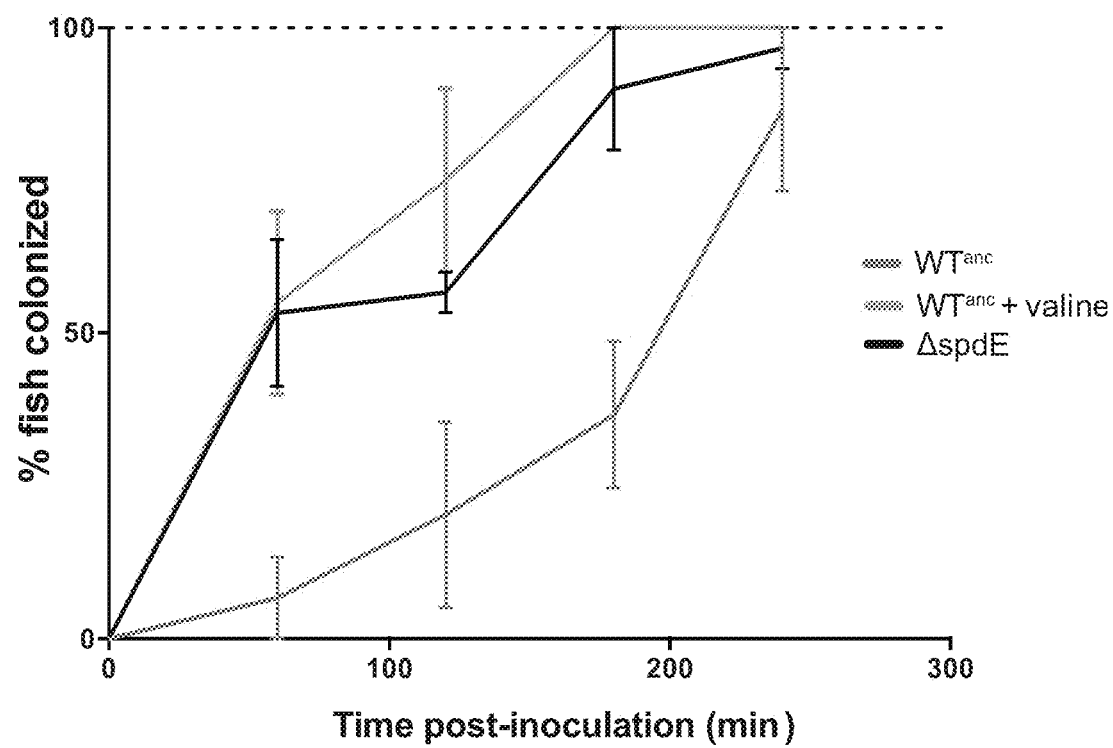

The initial observation was that loss-of-function mutations in spdE confer a colonization advantage to Aer01 by facilitating immigration into the fish and enabling these mutants to outcompete the ancestor. In vitro studies showed that this advantage could be attributed to the fact that SpdE functions to modulate Aer01 motility such that spdE mutants are more highly motile than the WT in the absence of SpdE ligands. However, the relative difference in motility between the WT and ΔspdE can be abated by the addition of SpdE ligand, which increases WT motility to levels similar to ΔspdE. To test whether WT motility, and therefore immigration into the host, could be increased with addition of ligands, competitions were performed as previously described, this time supplementing the inoculum and flask medium with SpdE ligand. Indeed, the addition of SpdE ligands reduced the competitive index of ΔspdE (FIG. 18A). With no ligand addition, ΔspdE overwhelmingly outcompeted WT (median CI=723), but when 1 mM proline was supplemented into the system ΔspdE nearly tied with WT (median CI=2). Once again, proline had a more dramatic effect than valine (median CI=7), as was observed in previous assays. It was confirmed that ligand-mediated competitive outcome was due to modulation of immigration of the WT in the presence of SpdE ligand (FIG. 18B). Furthermore, two much lower proline concentrations (100 nM, 10 nM) were tested, and these reduced CI but to a much lesser extent than the highest proline concentration (1 mM) (FIG. 18A). This validates the exploration assay results showing the sensitivity of Aer01 motility to spdE ligands to the nM range (FIG. 16), and demonstrates that very low concentrations of ligand can have important implications for host colonization.

Example 8

Microbiota Mediates spdE-Dependent Aer01 Motility

Figure 18E:
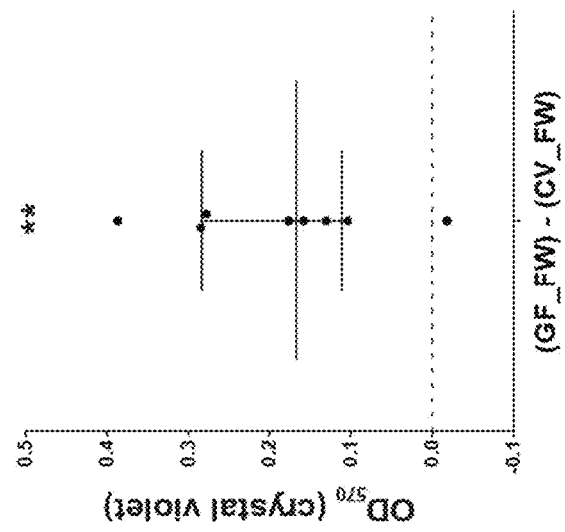
Figure 18D:
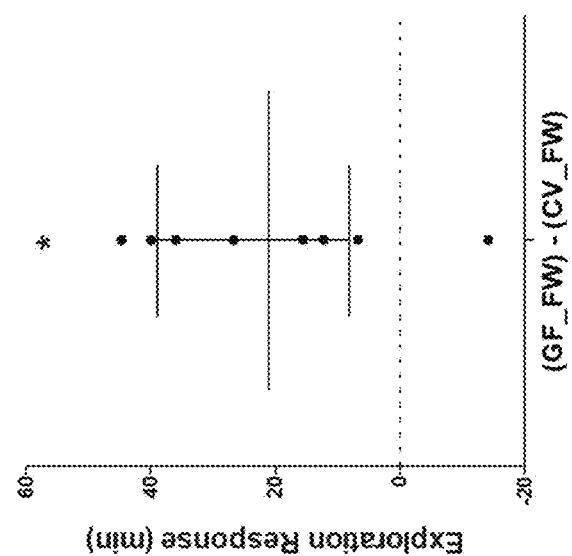
Figure 18C:
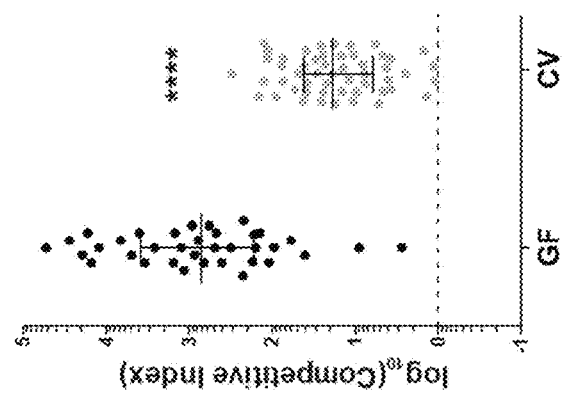

The emergence of loss-of-function spdE mutants in evolution experiments suggested that in this experimental evolution model system (germ-free zebrafish) the concentration of SpdE ligands was relatively low. If ligand concentrations were high, the relative competitive fitness between WT$^{anc}$ and spontaneous spdE mutants would have been significantly lower, reducing the selective advantage of those mutants and the likelihood that they would have risen to high enough numbers to be randomly selected from each evolved line. Moreover, the fact that WT$^{anc}$ Aer01 maintains a functional SpdE in spite of its overwhelming competitive advantage upon mutation in this system leaves open the question of SpdE's role in the natural system. To begin to investigate the relevance of spdE in a more natural context, competitions were conducted in conventionally-reared (CV) zebrafish (in the presence of a naturally-occurring complex microbiota). ΔspdE CI's were significantly lower in CV zebrafish, with a median CI of 19 in CV fish, compared to 723 in GF fish (FIG. 18C). These results recapitulate what was observed when SpdE ligands were supplemented into the system, and suggests that the presence of the CV microbiota augments pools of SpdE ligands.

To investigate differences in concentrations of amino acid SpdE ligands between GF and CV zebrafish conditions, the flask medium of 4-6 dpf GF and CV zebrafish were collected and filter-sterilized. Attempts to quantify amino acids via analytical techniques (e.g., mass spectrometry, enzymatic methods) were overall inconclusive due to the analytes being too close to, or below the limit of detection for those methods. As an alternative, we asked if we could detect differences based on Aer01's phenotypic response, since motility and competition assays had shown it to be sensitive to ligand concentrations in the nM range—more sensitive than the analytical methods. An "exploration assay" was used to measure differences in WT Aer01 motility in GF fish-conditioned water (GF_FW) compared to CV fish-conditioned water (CV_FW). A variable yet consistent trend of increased motility of WT Aer01 in CV_FW was observed, with a media exploration response of 21 minutes (FIG. 18D;

p=0.02). Next, biofilm formation was compared in these two conditions and, as expected, concomitant with increased motility, WT Aer01 biofilm formation was reduced in CV_FW FIG. 18E, p=0.004). Variability was prevalent in these assays; however, it is reasonable to assume that the composition of the CV microbiota varies across experiments, and that pools of free amino acids would also vary depending on the functional capacities of different taxa within the communities (FIGS. 19A and 19B). When looking at ΔspdE CI's across independent CV competitions experiments (CV fish generated on different weeks), median CI varied across experiments, suggestive of different SpdE ligand availability (FIG. 19C). Combined, these results suggest that the CV microbiota augments pools of SpdE ligands, thereby modulating Aer01 motility and facilitating host colonization.

Example 9

A Model for SpdE-Dependent Modulation of Aer01 Motility and Host Colonization

Without being bound by theory, based on the biochemical and phenotypic analyses, a model for how SpdE regulates Aer01 motility and enhances host colonization in response to ligand is proposed. SpdE, a transmembrane protein which spans the inner cell membrane, contains a sensing domain which binds ligands in the periplasmic space and regulates the diguanylate cyclase domain on the cytoplasmic side of the membrane (FIG. 20A). In the absence of ligands, SpdE's diguanylate cyclase is a default "ON" state, leading to high intracellular levels of c-di-GMP which inhibits motility and promotes biofilm formation. In the absence of the CV microbiota (e.g., germ-free hosts), ligand concentrations are relatively low, meaning that WT Aer01 is generally non-motile, prone to be aggregated or surface-attached (FIG. 20B). This means that for strains lacking a functional SpdE, they have low intracellular c-di-GMP, are more-highly motile and have a host colonization advantage. In the presence of SpdE ligands, as is the case for the CV host-microbe system where a complex microbiota is present, ligand-bound SpdE switches off diguanylate cyclase activity (FIG. 20C). This results in lower concentrations of c-di-GMP, reduced surface attachment and aggregation, and increased motility, which facilitates host colonization (FIG. 20D).

Example 10

Chimeric Amino Acid Sensors

Figure 21A:
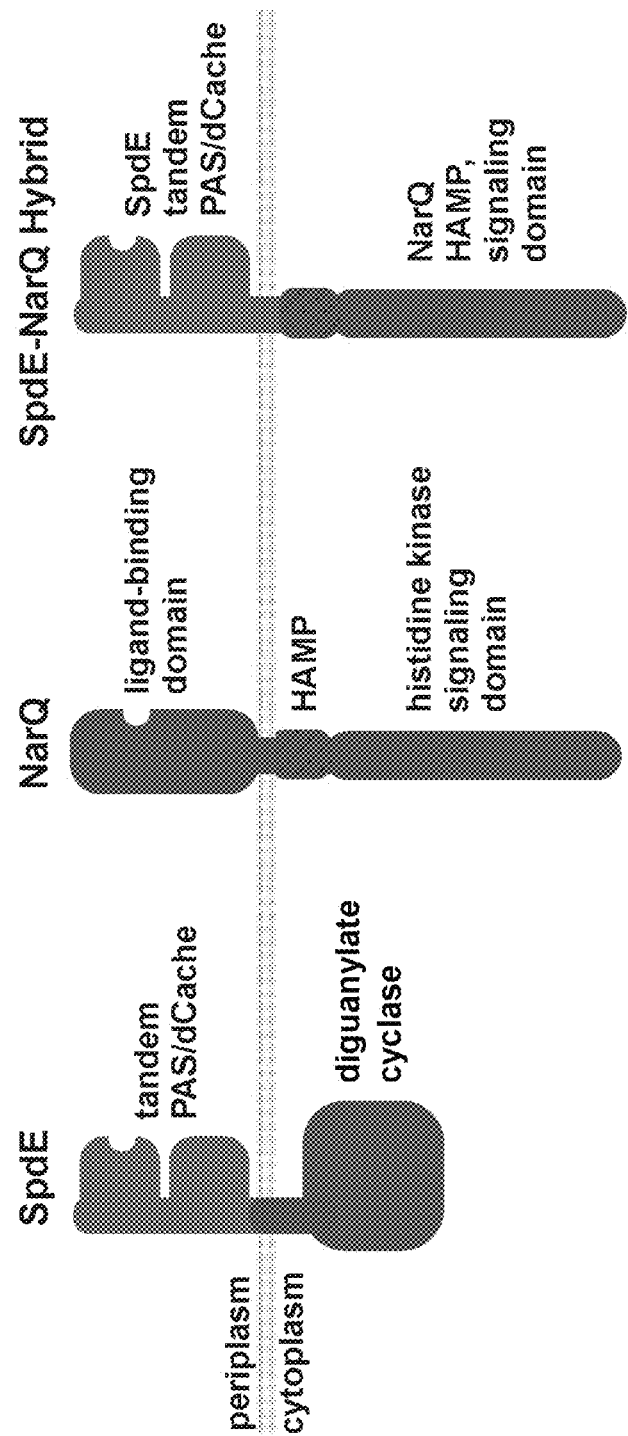
FIGS. 21A and 21B illustrate an exemplary fusion protein including SpdE tandem PAS/dCache domain and NarQ HAMP and histidine kinase signaling domains (FIG. 21A) and an exemplary method of detecting amino acids utilizing the fusion protein (FIG. 21B).
Figure 21B:
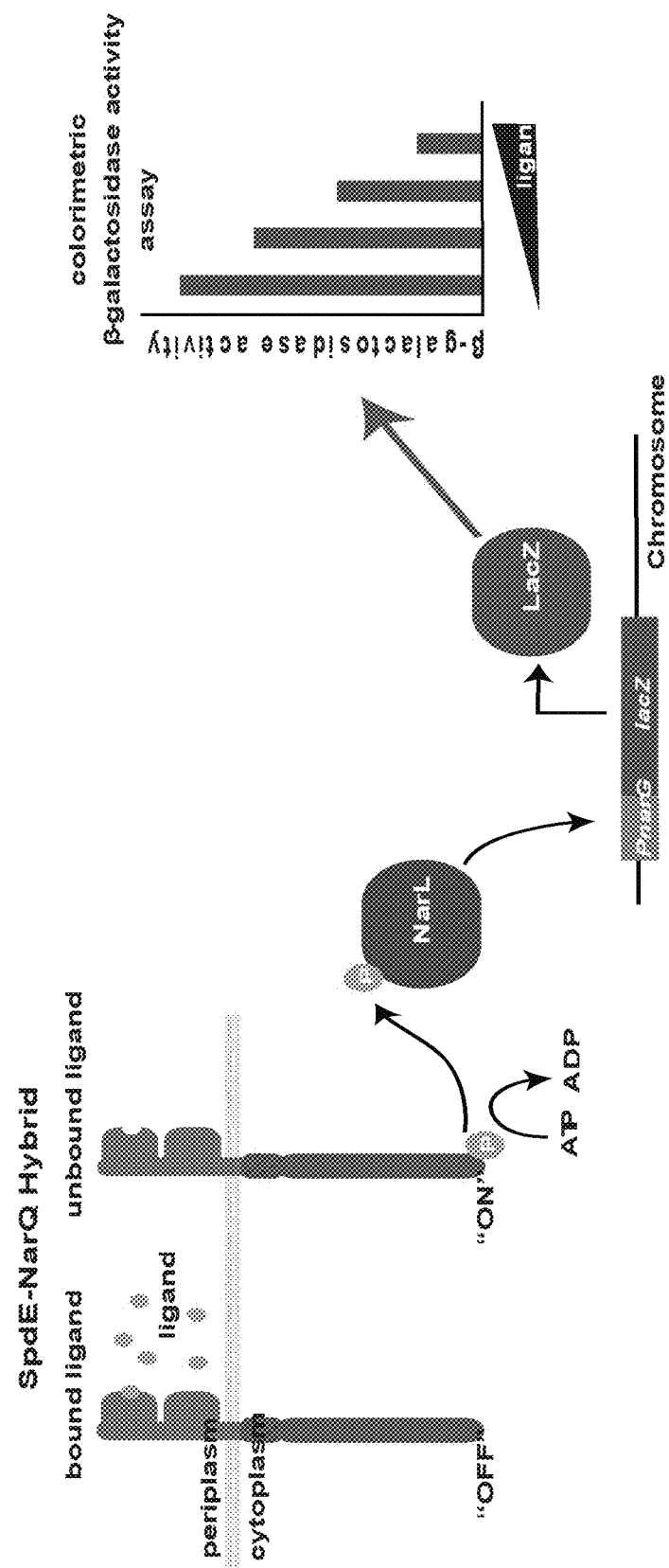

SpdE tandem PAS/dCache is a sensitive and specific sensor of particular amino acids. This domain is utilized for the design of novel biosensors of amino acid ligands by engineering chimeric reporter proteins fusing them to the signaling domain of an *Escherichia coli* protein, NarQ. NarQ is a nitrate/nitrite sensor which contains a C-terminal histidine kinase signaling domain. Here, the SpdE-NarQ hybrid protein includes the tandem PAS/dCache sensing domain (proximal and distal PAS/Cache domains) and both transmembrane domains of SpdE, and the HAMP and histidine kinase signaling domain of NarQ (FIG. 21A). When activated, the NarQ signaling domain auto-phosphorylates, then transfers the phosphoryl group to NarL, a transcriptional activator that binds nitrate-responsive promotors such as narG. In this system LacZ, a β-galactosidase, is under the control of the narG promoter, therefore activation of NarL results in expression of LacZ and increased β-galactosidase activity. The β-galactosidase activity is quantified via a colorimetric assay. Based on the sensitivity of SpdE-dependent responses in the assays disclosed herein, this hybrid protein is expected to detect ligand concentrations of 10 μM or less. This fusion protein will be in an active state in the absence of ligand (as seen for the native SpdE). Therefore, β-galactosidase activity will decrease with increasing ligand concentrations (e.g., FIG. 21B).

In some examples, the disclosed fusion protein (e.g., SEQ ID NO: 7) is used to measure amino acids levels in samples, for example as readouts of cellular physiology or for diagnostic purposes in clinical samples. For example, the fusion proteins may be used in methods for detecting amino acids in blood samples of Crohn's disease patients where it has been reported that there is a negative correlation between Crohn's Disease severity and plasma free amino acid concentrations, including the SpdE ligands valine and isoleucine (Chiba et al., *Clin. Med. Insights Gastroenterol.* 11: 1179552218791173, 2018).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of detecting presence or amount of one or more amino acids in a sample, comprising:
   contacting the sample with a sensing proline diguanylate cyclase enzyme (SpdE) protein;
   measuring diguanylate cyclase activity of the SpdE protein; and
   comparing the diguanylate cyclase activity of the SpdE protein to a control, wherein a decrease in diguanylate cyclase activity compared to the control indicates the presence or amount of one or more amino acids in the sample.

2. The method of claim 1, wherein the one or more amino acids are one or more of proline, valine, isoleucine, leucine, alanine, methionine, or threonine.

3. The method of claim 1, wherein measuring the diguanylate cyclase activity of the SpdE protein comprises measuring an amount of cyclic-di-GMP or pyrophosphate.

4. The method of claim 1, wherein contacting the sample with the SpdE protein comprises contacting the sample with a cell expressing the SpdE protein.

5. The method of claim 4, wherein measuring the diguanylate cyclase activity of the SpdE protein comprises measuring the motility of the cell expressing the SpdE protein and wherein an increase in the motility of the cell compared to the control indicates presence or amount of one or more amino acids in the sample.

6. The method of claim 1, wherein the SpdE protein comprises the amino acid sequence of SEQ ID NO: 1 or SEQ ID NO: 5.

7. The method of claim 6, wherein the SpdE protein is encoded by a nucleic acid comprising the nucleotide sequence of SEQ ID NO: 2 or SEQ ID NO: 6.

8. The method of claim 1, wherein the sample is from a subject, an environmental sample, or a laboratory sample.

9. The method of claim 8, wherein the sample is from a subject and comprises blood, serum, plasma, urine, or tissue or wherein the sample is an environmental sample and comprises soil, food, or water.

10. The method of claim 8, wherein the subject has or is suspected to have insulin resistance, prediabetes, diabetes, obesity, maple syrup disease, hyperprolinemia, or Crohn's disease.

11. The method of claim 10, further comprising:
   identifying the subject as having insulin resistance, prediabetes, diabetes, obesity, maple syrup disease, hyperprolinemia, or Crohn's disease if an increase in the amount of one or more amino acids is detected; and
   administering to the subject one or more treatments for insulin resistance, prediabetes, diabetes, obesity, maple syrup disease, hyperprolinemia, or Crohn's disease.

12. A method of detecting presence or amount of one or more amino acids in a sample, comprising:
   contacting the sample with a fusion protein comprising a sensing proline diguanylate cyclase enzyme (SpdE) polypeptide tandem Per-Arnt-Sim/double Cache (PAS/dCache) domain linked to a signaling domain of a bacterial two-component system;
   measuring an activity of the signaling domain; and
   comparing the activity of the signaling domain to a control, wherein a decrease in activity compared to the control indicates the presence or amount of one or more amino acids in the sample.

13. The method of claim 12, wherein activity of the signaling domain results in β-galactosidase activity or fluorescence of a fluorescent protein.

14. The method of claim 12, wherein the PAS/dCache domain comprises amino acids 38-286 of SEQ ID NO: 1 or amino acids 43-290 of SEQ ID NO: 5.

15. The method of claim 12, wherein the fusion protein comprises the amino acid sequence of SEQ ID NO: 7.

* * * * *